United States Patent
Dugar et al.

(10) Patent No.: US 7,223,766 B2
(45) Date of Patent: May 29, 2007

(54) BI-CYCLIC PYRIMIDINE INHIBITORS OF TGFβ

(75) Inventors: Sundeep Dugar, San Jose, CA (US); Sarvajit Chakravarty, Mountain View, CA (US); Aurelia Conte, Loerrach (DE); Jonathan Axon, Milpitas, CA (US); Glenn McEnroe, San Mateo, CA (US); Alison Murphy, Milpitas, CA (US)

(73) Assignee: Scios, Inc., Fremont, CA (US)

( * ) Notice: Subject to any disclaimer, the term of this patent is extended or adjusted under 35 U.S.C. 154(b) by 271 days.

(21) Appl. No.: 10/811,428

(22) Filed: Mar. 26, 2004

(65) Prior Publication Data

US 2005/0004143 A1    Jan. 6, 2005

Related U.S. Application Data

(60) Provisional application No. 60/458,982, filed on Mar. 28, 2003.

(51) Int. Cl.
*A61K 31/517* (2006.01)
*C07D 239/70* (2006.01)

(52) U.S. Cl. .................... 514/258.1; 544/253
(58) Field of Classification Search ............. 544/253; 514/258.1
See application file for complete search history.

(56) References Cited

U.S. PATENT DOCUMENTS

| 3,720,674 A | 3/1973 | Breuer et al. |
| 6,339,072 B2 | 1/2002 | Martin et al. |

FOREIGN PATENT DOCUMENTS

| DE | 248 593 | 8/1987 |
| WO | WO-97/16452 | 5/1997 |
| WO | WO 00/12497 | 3/2000 |
| WO | WO 01/47921 | 7/2001 | ........... 417/12 |
| WO | WO 02/22601 A1 * | 3/2002 | |
| WO | WO 02/076976 | 10/2002 | ........... 403/4 |
| WO | WO 02/079197 | 10/2002 | ........... 405/4 |
| WO | WO-03/078423 | 9/2003 | |
| WO | WO-03/078426 | 9/2003 | |
| WO | WO-03/078427 | 9/2003 | |

OTHER PUBLICATIONS

Roberts and Sporn, Handbook of Experimental Pharmacology (1990) 95: 419-458.
International Search Report for PCT/US04/09300, mailed on Jan. 4, 2005, 2 pages.
Birnbaumer et al., Cell 1992 vol. 71 pp. 1069-1072.
Cooper et al., J Chem Soc Perkin Trans 1984 vol. 1 pp. 799-809.
Crawford et al., Cell 1998 vol. 93 pp. 1159-1170.
Dowd et al., Tetrahedron 1991 vol. 47 pp. 4847-4860.
Greco et al., Tetrahedron Lett 1992 vol. 33(35) pp. 5009-5012.
Lawrence et al Eur J. Cytokine Network 1996 vol. 7 pp. 363-374.
Lin et al., Cell 1992 vol. 68 pp. 775-785.
Lopez-Casillas et al., Cell 1991 vol. 67 pp. 785-795.
Lyons et al., Eur J. Biochem 1990 vol. 187 p. 467.
Massague et al., Cell 1992 vol. 69 pp. 1067-1070.
Massague et al Ann Cell Biol 1990 6 597-646.
Massague et al Ann Rev Biochem 1998 vol. 67 pp. 753-791.
Moyer et al., J Org Chem 1985 vol. 50 pp. 5223-5230.
Munger et al., Cell 1999 pp. 319-328.
Munger et al., Kidney Intl 1997 vol. 51 pp. 1376-1374 and 1376-1382.
Wahl et al., Immunol Today 1989 vol. 10 pp. 258-261.
Wang et al., Cell 1991 vol. 67 pp. 797-805.
Wang et al., Tetrahedron 1998 vol. 29 pp. 8355-8370.
Wolff et al., J Med Chem 1970 vol. 13(3) pp. 531-534.
Wrana et al Cell 1992 vol. 71 pp. 1003-1014.

* cited by examiner

*Primary Examiner*—Zachary C. Tucker
*Assistant Examiner*—Erich A. Leeser
(74) *Attorney, Agent, or Firm*—Morrison & Foerster LLP

(57) ABSTRACT

Compounds in which a pyrimidine nucleus is bridged at the 5 and 6 position and are further substituted at positions 2 and 4 with substituents comprising aromatic moieties are useful in treating subjects with rheumatoid arthritis ameliorated by inhibition of TGFβ activity.

7 Claims, No Drawings

BI-CYCLIC PYRIMIDINE INHIBITORS OF TGFβ

CROSS-REFERENCE TO RELATED APPLICATION

This application claims benefit of U.S. provisional application 60/458,982 filed Mar. 28, 2003. The contents of this document are incorporated herein by reference.

TECHNICAL FIELD

The invention relates to compounds useful to inhibit TGFβ. Such compounds are useful in treating conditions that are mediated by TGFβ, examples of which include fibrotic, pulmonary, and oncologic disorders.

BACKGROUND ART

Transforming growth factor-beta (TGFβ) denotes a superfamily of proteins that includes, for example, TGFβ1, TGFβ2, and TGFβ3, which are pleiotropic modulators of cell growth and differentiation, embryonic and bone development, extracellular matrix formation, hematopoiesis, immune and inflammatory responses (Roberts and Sporn, *Handbook of Experimental Pharmacology* (1990) 95:419-458; Massague, et al., *Ann. Rev. Cell. Biol.* (1990) 6:597-646). Other members of this superfamily include activin, inhibin, bone morphogenic protein, and Mullerian inhibiting substance. The members of the TGFβ family initiate intracellular signaling pathways leading ultimately to the expression of genes that regulate the cell cycle, control proliferative responses, or relate to extracellular matrix proteins that mediate outside-in cell signaling, cell adhesion, migration and intercellular communication.

Therefore, inhibitors of the TGFβ intracellular signaling pathway are useful treatments for fibroproliferative diseases. Specifically, fibroproliferative diseases include kidney disorders associated with unregulated TGFβ activity and excessive fibrosis including glomerulonephritis (GN), such as mesangial proliferative GN, immune GN, and crescentic GN. Other renal conditions include diabetic nephropathy, renal interstitial fibrosis, renal fibrosis in transplant patients receiving cyclosporin, and HIV-associated nephropathy. Collagen vascular disorders include progressive systemic sclerosis, polymyositis, scleroderma, dermatomyositis, eosinophilic fascitis, morphea, or those associated with the occurrence of Raynaud's syndrome. Lung fibroses resulting from excessive TGFβ activity include adult respiratory distress syndrome, Chronic Obstructive Pulmonary Disease (COPD), idiopathic pulmonary fibrosis, and interstitial pulmonary fibrosis often associated with autoimmune disorders, such as systemic lupus erythematosus and scleroderma, chemical contact, or allergies. Another autoimmune disorder associated with fibroproliferative characteristics is rheumatoid arthritis.

Fibroproliferative conditions can be associated with surgical eye procedures. Such procedures include retinal reattachment surgery accompanying proliferative vitreoretinopathy, cataract extraction with intraocular lens implantation, and post glaucoma drainage surgery.

The compounds of the invention herein are derivatives of pyrimidine or triazine. PCT publication WO01/47921 describes pyrimidine and triazine compounds that are inhibitors of kinase activities associated with various inflammatory conditions, as opposed to the treatment of fibroproliferative disorders described herein. The above mentioned PCT publication describes the use of the compounds disclosed only for treatment of the inflammatory aspects of certain autoimmune diseases. Further, the compounds described differ from those described herein by virtue of the substitutions required on the pyrimidine or triazine nucleus; among other distinctions, the compounds disclosed in this publication do not include phenyl bound directly to the pyrimidine or triazine ring.

In addition, PCT publications WO 00/12497 and WO 02/076976 describe quinazoline derivatives that are inhibitors of TGFβ. However, these compounds are fully aromatic bicyclic structures. PCT publication WO 02/079197 describes pyrimidines which do not contain bridging fused rings and which require aryl amide substitutions in the 2 position.

DISCLOSURE OF THE INVENTION

The compounds of the present invention are pyrimidine derivatives which contain a fused ring bridging positions 5 and 6. The compounds are of the formula

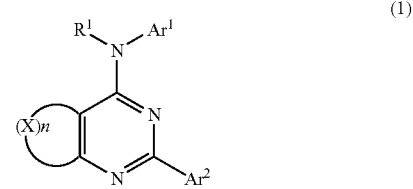

(1)

or a pharmaceutically acceptable salt thereof, wherein the fused ring bridging positions 5 and 6 of the pyrimidine ring is saturated, unsaturated or aromatic. The fused ring is an optionally substituted ring and contains 4-7 members, where each member is independently C, N, O or S. However, if said fused ring contains 6 members, it is not aromatic.

Each of $Ar^1$ and $Ar^2$ is independently an optionally substituted aromatic moiety or optionally substituted heteroaromatic moiety wherein said heteroaromatic moiety contains one or more O, S, and/or N; typically these moieties contain 5-12 members.

$R^1$ is H, or optionally substituted alkyl (1-10C), alkenyl (2-10C), or alkynyl (2-10C).

Thus, in one aspect, the invention is related to the compounds of formula (1). In other aspects, the invention is directed to pharmaceutical compositions of formula (1) and to methods to treat conditions mediated by TGFβ, including fibroproliferative diseases or conditions using these compounds. More generally, the invention is directed to methods to treat conditions which are benefited by inhibition of TGFβ.

MODES OF CARRYING OUT THE INVENTION

The compounds of formula (1) are useful in treating conditions which are characterized by overactivity of TGFβ. Conditions "characterized by enhanced TGFβ activity" include those wherein TGFβ synthesis is stimulated so that TGFβ is present in enhanced amount or wherein TGFβ latent protein is undesirably activated or converted to active TGFβ protein or wherein TGFβ receptors are upregulated or wherein the TGFβ protein shows enhanced binding to cells or extracellular matrix in the location of the disease. Thus, in either case, "enhanced activity" refers to any condition wherein the effectiveness of TGFβ is undesirably high, regardless of the cause.

As used herein, "TGFβ" refers to the superfamily which includes TGFβ1, TGFβ2, and TGFβ3 as well as other members of the family known or which became known in the art such as inhibin, bone morphogenic protein, and the like. One or more of these family members may be elevated in the conditions which the compounds of the invention are designed to ameliorate or prevent.

The Invention Compounds

The compounds useful in the invention are derivatives of pyrimidine containing a bridge at positions 5-6 and mandatory substituents at positions corresponding to the 2- and 4-positions of pyrimidine. Further non-interfering substituents may also be included.

As used herein, a "noninterfering substituent" is a substituent which leaves the ability of the compound of formula (1) to inhibit TGFβ activity qualitatively intact. Thus, the substituent may alter the degree of inhibition, but as long as the compound of formula (1) retains the ability to inhibit TGFβ activity, the substituent will be classified as "noninterfering."

As used herein, the term "alkyl," "alkenyl" and "alkynyl" include straight-chain, branched-chain and cyclic monovalent substituents, containing only C+H when they are unsubstituted. Examples include methyl, ethyl, isobutyl, cyclohexyl, cyclopentylethyl, 2-propenyl, 3-butynyl, and the like. Typically, the alkyl, alkenyl and alkynyl substituents contain 1-10C (alkyl) or 2-10C (alkenyl or alkynyl). Preferably they contain 1-6C (lower alkyl) or 2-6C (lower alkenyl or lower alkynyl).

Heteroalkyl, heteroalkenyl and heteroalkynyl are similarly defined but may contain 1 or more O, S or N heteroatoms or combinations thereof within the backbone residue.

As used herein, "acyl" encompasses the definitions of alkyl, alkenyl, alkynyl, and heteroacyl includes the related heteroforms, each of which are coupled to an additional residue through a carbonyl group.

"Aromatic" moiety or "aryl" moiety refers to a monocyclic or fused bicyclic moiety such as phenyl or naphthyl; "heteroaromatic" also refers to monocyclic or fused bicyclic ring systems containing one or more heteroatoms selected from O, S and N. The inclusion of a heteroatom permits inclusion of 5-membered rings as well as 6-membered rings. Thus, typical aromatic/heteroaromatic systems include pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, imidazolyl and the like. Because tautomers are theoretically possible, phthalimido is also considered aromatic. Any monocyclic or fused ring bicyclic system which has the characteristics of aromaticity in terms of electron distribution throughout the ring system is included in this definition. Typically, the ring systems contain 5-12 ring member atoms.

Similarly, "arylalkyl" and "heteroarylalkyl" refer to aromatic and heteroaromatic systems which are coupled to another residue through a carbon chain, including substituted or unsubstituted, saturated or unsaturated, carbon chains, typically of 1-8C, or the hetero forms thereof. These carbon chains may also include a carbonyl group, thus making them able to provide substituents as an acyl or heteroacyl moiety.

In general, any alkyl, alkenyl, alkynyl, acyl, or aryl group contained in a substituent may itself optionally be substituted by additional substituents. The nature of these substituents is similar to those recited with regard to the primary substituents themselves. Thus, where an embodiment of a substituent is alkyl, this alkyl may optionally be substituted by the remaining substituents listed as substituents where this makes chemical sense, and where this does not undermine the size limit of alkyl per se; e.g., alkyl substituted by alkyl or by alkenyl would simply extend the upper limit of carbon atoms for these embodiments. However, alkyl substituted by aryl, amino, alkoxy, and the like would be included. The features of the invention compounds are defined by formula (1) and the nature of the substituents is less important as long as the substituents do not interfere with the stated biological activity of this basic structure.

Non-interfering substituents on $Ar^1$ or $Ar^2$, include, but are not limited to, alkyl, alkenyl, alkynyl, halo, OR, $NR_2$, SR, —SOR, —$SO_2R$, —OCOR, —NRCOR, —$NRCONR_2$, —NRCOOR, —$OCONR_2$, —RCO, —COOR, $SO_2R$, NRSOR, $NRSO_2R$, —$SO_3R$, —$CONR_2$, $SO_2NR_2$, wherein each R is independently H or alkyl (1-8C), —CN, —$CF_3$, and $NO_2$, and like substituents. $R^3$ and $R^4$ can also be H. Preferred embodiments for $R^3$ and $R^4$ are H, alkyl (1-10C) or a heteroatom-containing form thereof, each optionally substituted, especially (1-4C) alkyl; alkoxy (1-8C), acylamido, aryloxy, arylalkyloxy, especially wherein the aryl group is a phthalimido group, and alkyl or arylalkyl amine.

Preferably $Ar^1$ and $Ar^2$ are optionally substituted phenyl, 2-, 3- or 4-pyridyl, indolyl, 2- or 4-pyrimidyl, pyridazinyl, benzotriazol or benzimidazolyl. More preferably $Ar^1$ and $Ar^2$ are phenyl, pyridyl, or pyrimidyl. Preferably $Ar^1$ is pyridyl or pyrimidyl and $Ar^2$ is phenyl. Each of these embodiments may optionally be substituted with a group such as alkyl, alkenyl, alkynyl, aryl, O-aryl, O-alkylaryl, O-aroyl, NR-aryl, N-alkylaryl, NR-aroyl, halo, OR, $NR_2$, SR, —OOCR, —NROCR, RCO, —COOR, —$CONR_2$, and/or $SO_2NR_2$, wherein each R is independently H or alkyl (1-8C), and/or by —CN, —$CF_3$, and/or $NO_2$. Alkyl, alkenyl, alkynyl and aryl portions of these may be further substituted by similar substituents.

Preferred substituents on $Ar^1$ or $Ar^2$ include alkyl, alkenyl, alkynyl, halo, OR, SR, $NR_2$ wherein R is H or alkyl (1-4C); and/or arylamino, arylalkylamino, including alkylamino which is substituted by more than one aryl. As stated above, any aryl or alkyl group included within a substituent may itself be substituted similarly. These substituents may occupy all available positions of the ring, preferably 1-2 positions, or more preferably only one position.

Any of the aryl moieties, including those depicted in formula (1) especially the phenyl moieties, may also comprise two substituents which, when taken together, form a 5-7 membered carbocyclic or heterocyclic aliphatic ring. The bridge between positions 5 and 6 of the pyrimidine ring forms a fused ring system wherein, if the fused ring contains 6 members, it is not aromatic. However, the bridge may contain pi bonds and may contain one or more heteroatoms which are selected from N, O, and S. Preferred embodiments include those wherein the bridge results in a 5-membered ring optionally containing one or two nitrogens, a nitrogen and an oxygen, an oxygen, an additional double bond, a saturated bridge, or a 6-membered ring formed by a bridge which is saturated. In one embodiment, the 6-membered saturated bridge-generated ring contains one or two nitrogen. The ring formed by the bridge may itself be substituted. The substituents described above for $Ar^1$ and $Ar^2$ may also be present as fused ring systems.

The compounds of formula (1) may be supplied in the form of their pharmaceutically acceptable acid-addition salts including salts of inorganic acids such as hydrochloric, sulfuric, hydrobromic, or phosphoric acid or salts of organic acids such as acetic, tartaric, succinic, benzoic, salicylic, and the like. If a carboxyl moiety is present on the compound of formula (1), the compound may also be supplied as a salt with a pharmaceutically acceptable cation.

The compounds of formula (1) may also be supplied in the form of a "prodrug" which is designed to release the compound of formula (1) when administered to a subject. Prodrug formed designs are well known in the art, and depend on the substituents contained in the compound of formula (1). For example, a substituent containing sulfhydryl could be coupled to a carrier which renders the compound biologically inactive until removed by endogenous enzymes or, for example, by enzymes targeted to a particular receptor or location in the subject In the event that any of the substituents of formula (1) contain chiral centers, as some, indeed, do, the compounds of formula (1) include all stereoisomeric forms thereof, both as isolated stereoisomers and mixtures of these stereoisomeric forms.

Synthesis of the Invention Compounds

A number of synthetic routes may be employed to produce the compounds of the invention. In general, they may be synthesized using reactions known in the art. Any art-known method for synthesis may be employed. However, the following synthetic routes are convenient for preparation of the invention compounds. Typical invention compounds are as shown below:

| Compound # | Structure | IC$_{50}$ (µM) |
| --- | --- | --- |
| 1 | | NA |
| 2 | | 9.4 |
| 3 | | 0.78 |
| 4 | 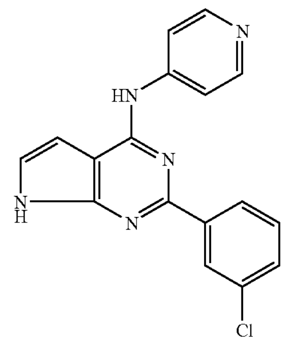 | NA |
| 5 | 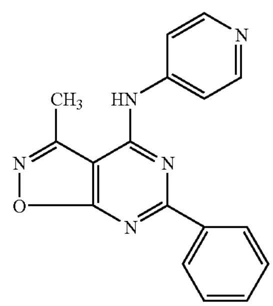 | NA |
| 6 | 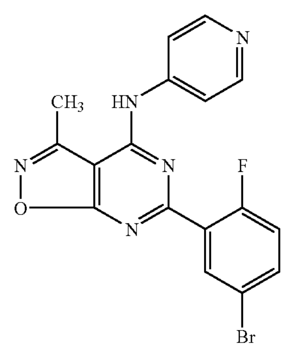 | 0.27 |
| 7 | 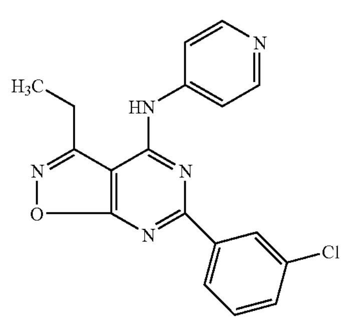 | 5.068 |

-continued

| Compound # | Structure | IC$_{50}$ (μM) |
|---|---|---|
| 8 | 3-methyl-isoxazolo-pyrimidine with 4-pyridylamino and 5-chloro-2-fluorophenyl | 0.267 |
| 9 | 3-phenyl-isoxazolo-pyrimidine with 4-pyridylamino and 3-chlorophenyl | NA |
| 10 | 3-methyl-isoxazolo-pyrimidine with 4-pyridylamino and 3-iodophenyl | 2.44 |
| 11 | 3-ethyl-isoxazolo-pyrimidine with 4-pyridylamino and 5-chloro-2-fluorophenyl | 1.35 |
| 12 | 3-methyl-isoxazolo-pyrimidine with 4-pyridylamino and 2-fluorophenyl | 1.38 |
| 13 | 3-methyl-isoxazolo-pyrimidine with 3-pyridylamino and 2-fluorophenyl | NA |
| 14 | 3-methyl-isoxazolo-pyrimidine with 4-pyridylamino and 2-chlorophenyl | 12.81 |
| 15 | 3-methyl-isoxazolo-pyrimidine with 4-pyridylamino and 3-bromophenyl | 1.02 |
| 16 | 7-methyl-imidazo-pyrimidine with 4-pyridylamino and phenyl | NA |
| 17 | 3-methyl-isoxazolo-pyrimidine with 4-pyridylamino and 4-chlorophenyl | 4.65 |

-continued
| Compound # | Structure | IC$_{50}$ (μM) |
|---|---|---|
| 18 | 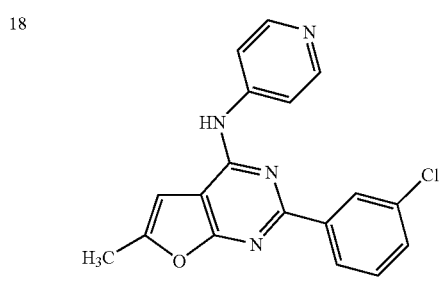 | NA |
| 19 | 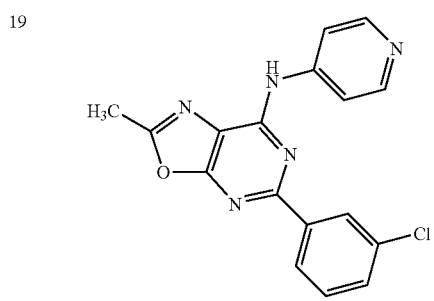 | NA |
| 20 | 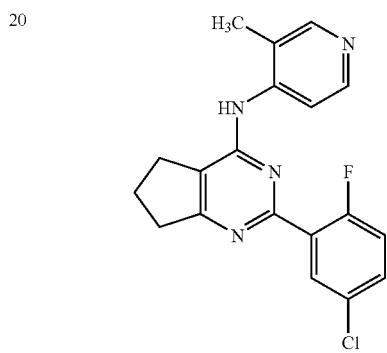 | 0.093 |
| 21 | 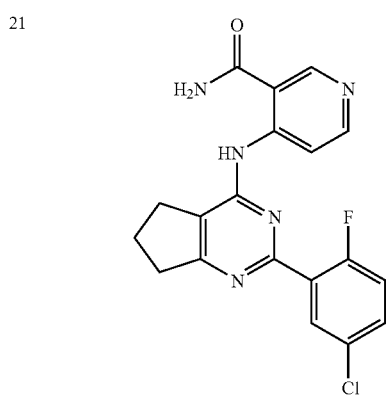 | 0.053 |
-continued
| Compound # | Structure | IC$_{50}$ (μM) |
|---|---|---|
| 22 | 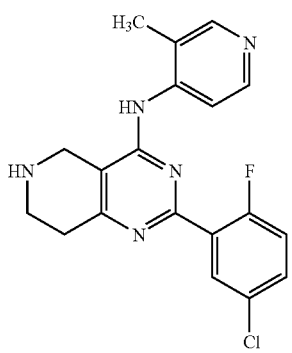 | 6.27 |
| 23 | 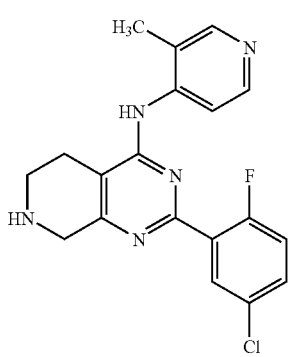 | 1.18 |
| 24 | 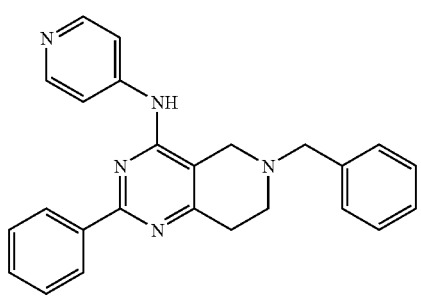 | NA |
| 25 | 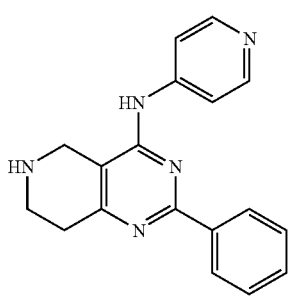 | NA |

-continued
| Compound # | Structure | IC$_{50}$ (μM) |
|---|---|---|
| 26 | 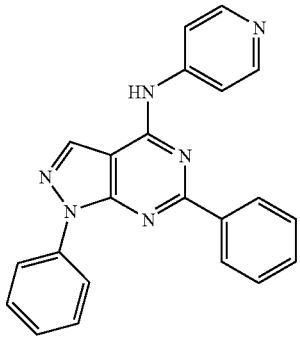 | NA |
| 27 | 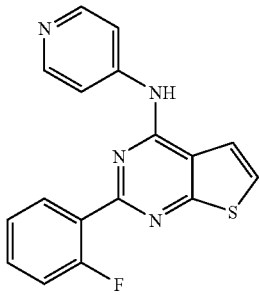 | NA |
| 28 | 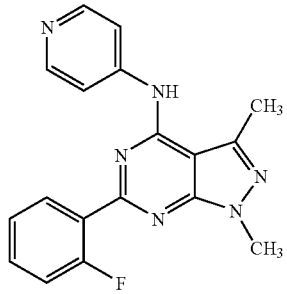 | NA |
| 29 | 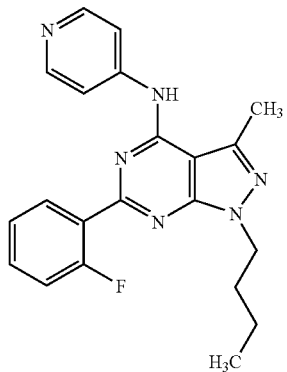 | NA |
-continued
| Compound # | Structure | IC$_{50}$ (μM) |
|---|---|---|
| 30 | 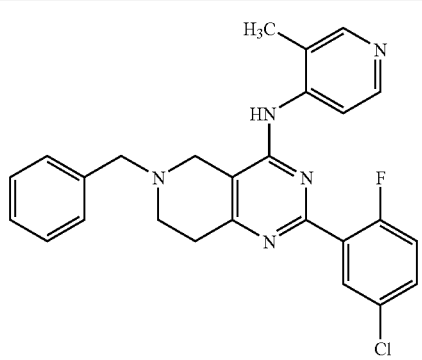 | 16.141 |
| 32 | 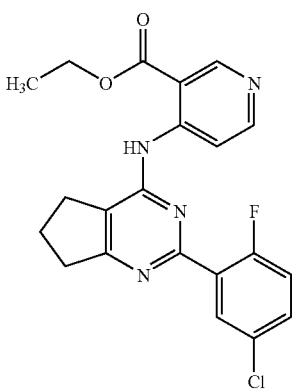 | 6.5 |
| 33 | 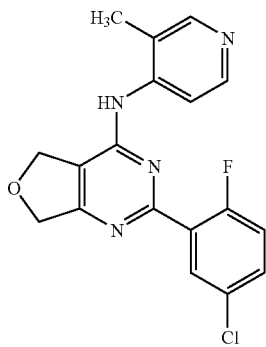 | 3.1 |
| 34 | 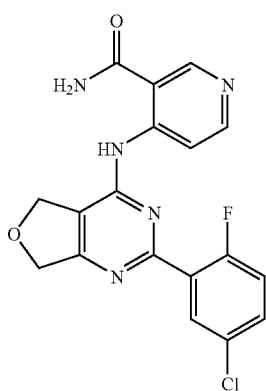 | 2.2468 |

-continued

| Compound # | Structure | IC$_{50}$ (μM) |
|---|---|---|
| 35 | 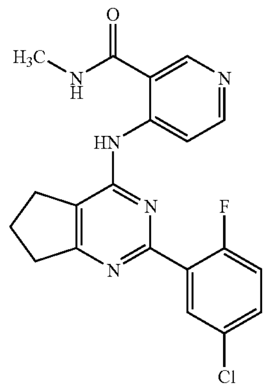 | 0.049 |
| 36 | 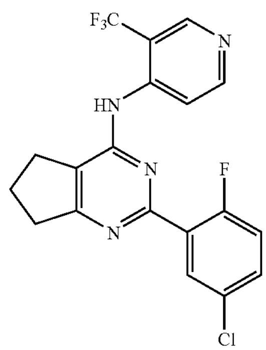 | 0.1696 |
| 37 | 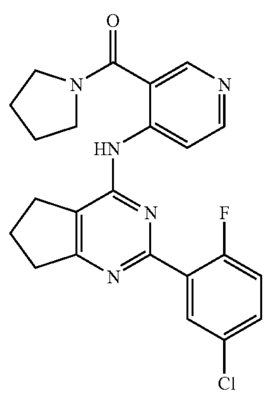 | 2.2364 |
| 38 | 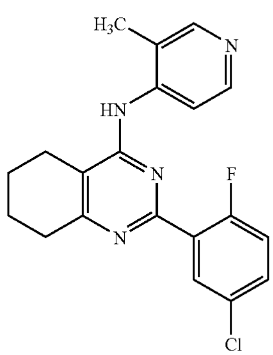 | 0.2518 |

-continued

| Compound # | Structure | IC$_{50}$ (μM) |
|---|---|---|
| 39 | 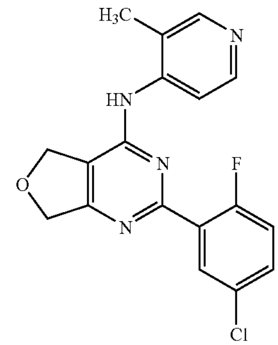 | 0.0923 |
| 40 | 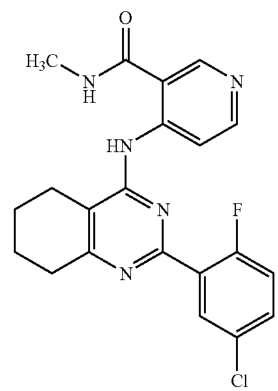 | 0.0501 |
| 41 | 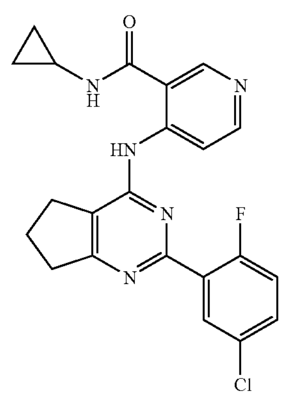 | 1.3517 |
| 42 | 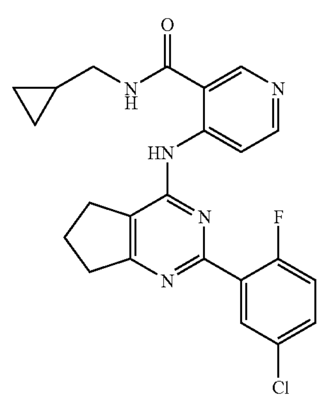 | 1.33 |

-continued
| Compound # | Structure | IC$_{50}$ (μM) |
|---|---|---|
| 43 | 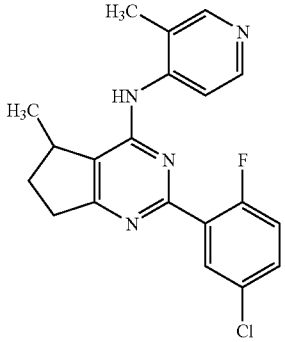 | 0.1043 |
| 44 | 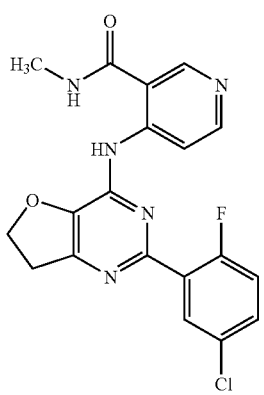 | 0.148 |
| 45 | 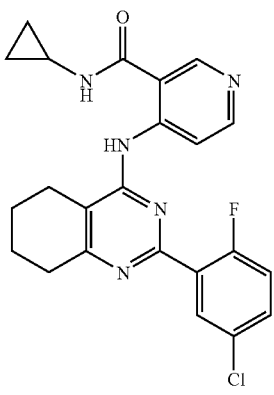 | 0.6827 |
| 46 | 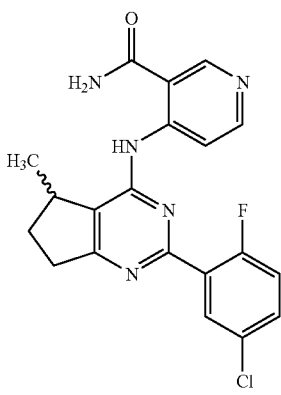 | 0.013 |
-continued
| Compound # | Structure | IC$_{50}$ (μM) |
|---|---|---|
| 47 | 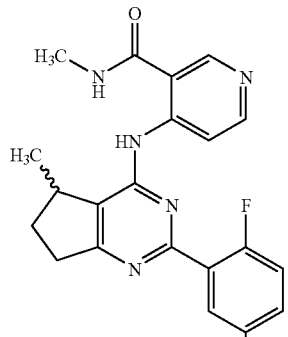 | 0.0145 |
| 48 | 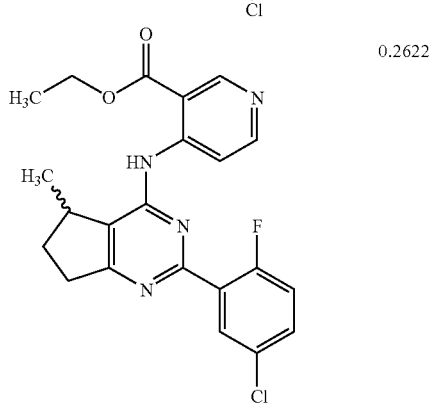 | 0.2622 |
| 49 | 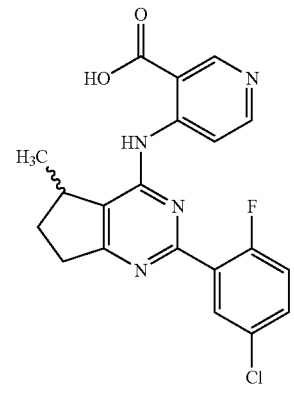 | 0.0853 |
| 50 | 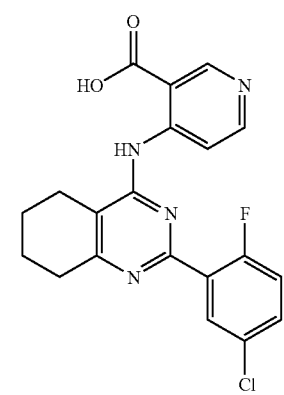 | 4.0849 |

| Compound # | Structure | IC$_{50}$ (μM) |
|---|---|---|
| 51 | 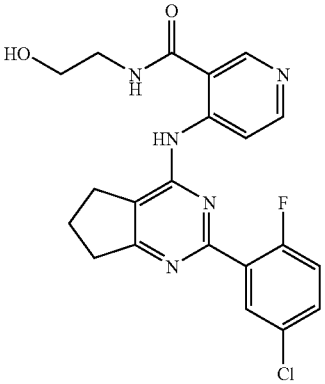 | NA |
| 52 | 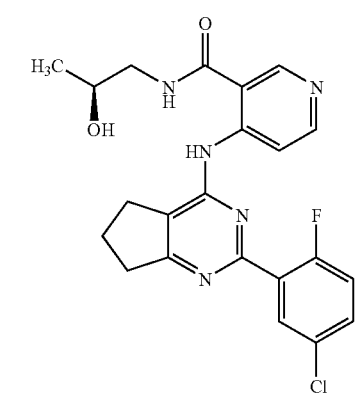 | 0.2384 |
| 53 | 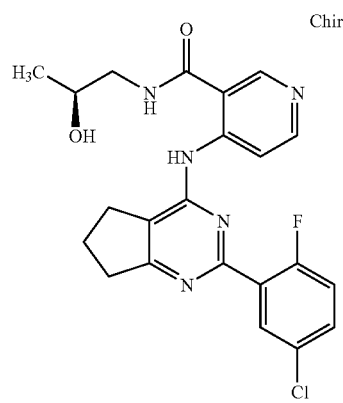 Chiral | 0.4169 |
| 54 | 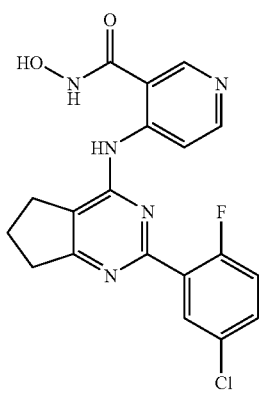 | 0.4856 |
| 55 | 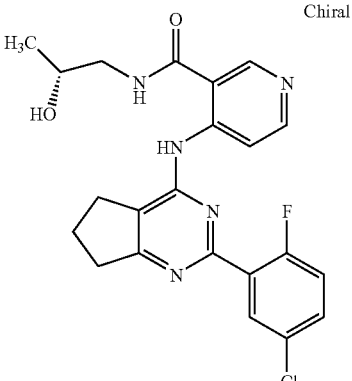 Chiral | 0.6393 |
| 56 | 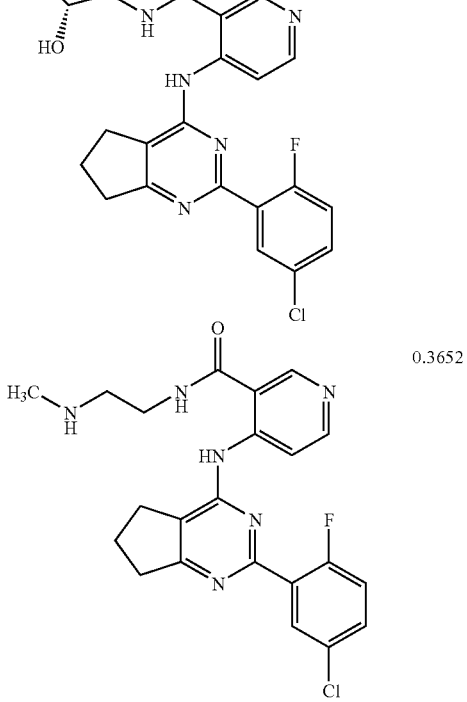 | 0.3652 |
| 57 |  | 0.4357 |
| 58 | 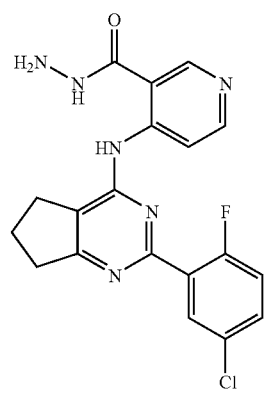 | 0.0626 |

-continued
| Compound # | Structure | IC$_{50}$ (μM) |
|---|---|---|
| 59 | 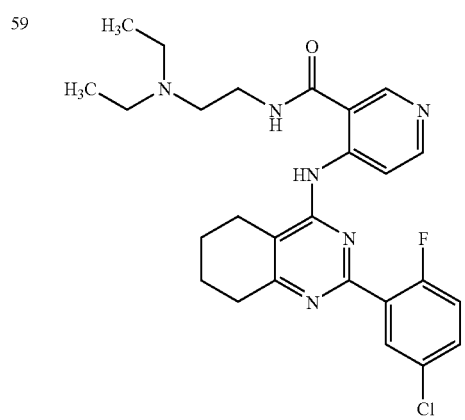 | 0.0779 |
| 60 | 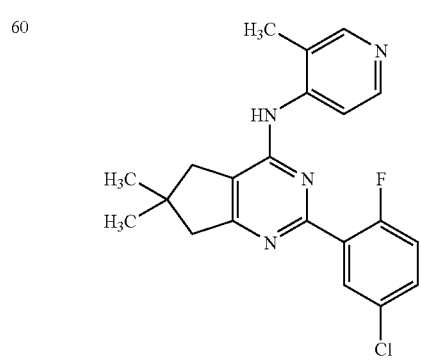 | 2.4211 |
| 61 | 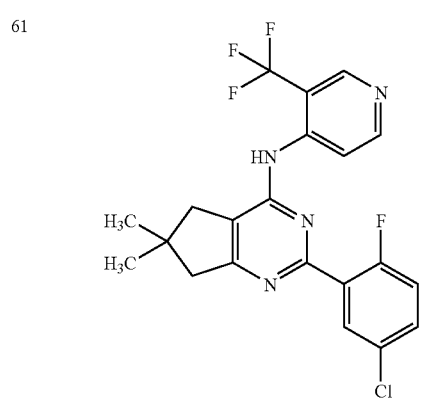 | 6.2546 |
-continued
| Compound # | Structure | IC$_{50}$ (μM) |
|---|---|---|
| 62 | 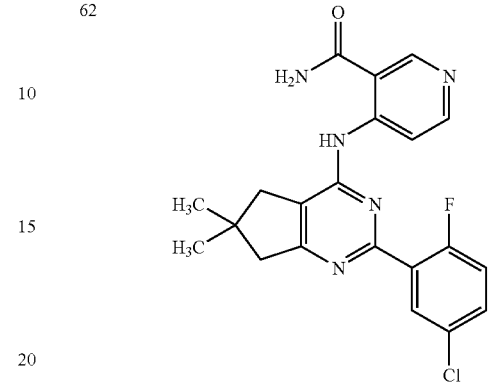 | 0.2053 |
| 63 | 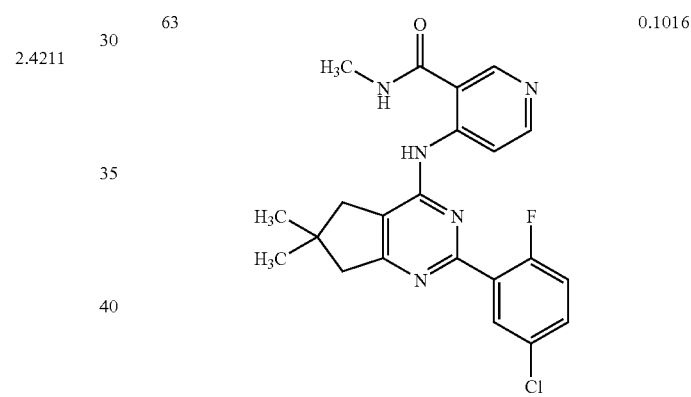 | 0.1016 |
| 64 | 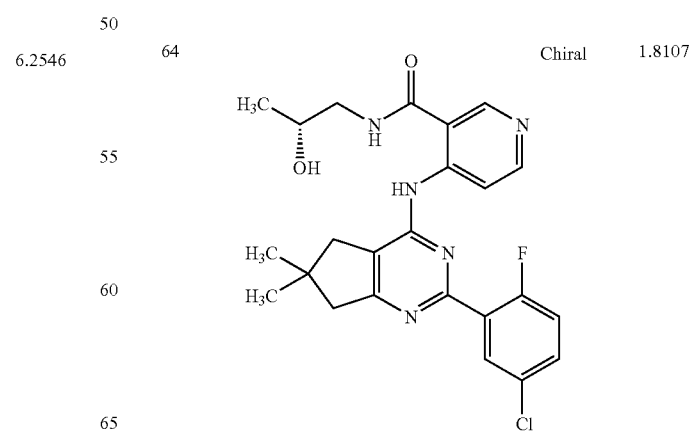 Chiral | 1.8107 |

-continued
| Compound # | Structure | IC$_{50}$ (μM) |
|---|---|---|
| 65 | 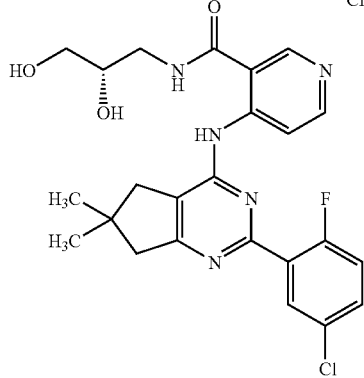 Chiral | 2.7853 |
| 66 | 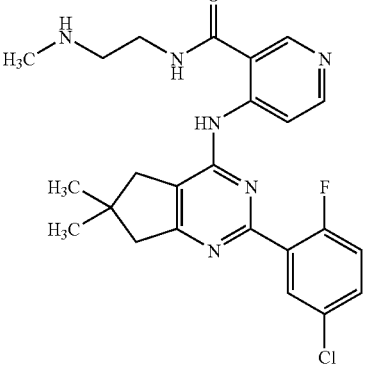 | 1.2469 |
| 67 | 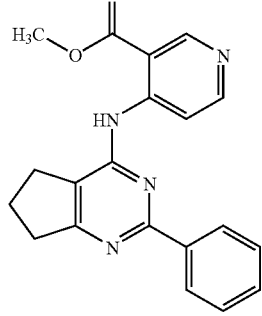 | 8.846 |
| 68 | 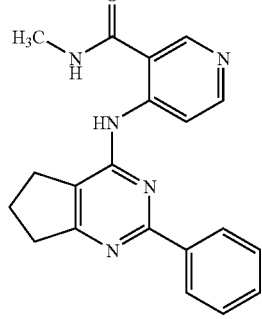 | 0.2887 |
-continued
| Compound # | Structure | IC$_{50}$ (μM) |
|---|---|---|
| 69 | 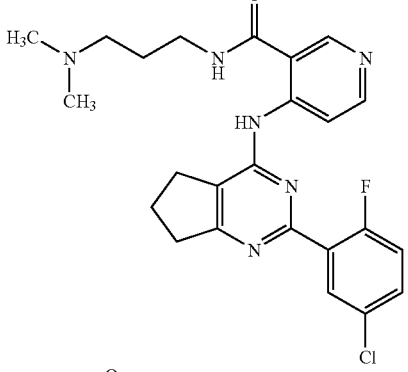 | 0.0902 |
| 70 | 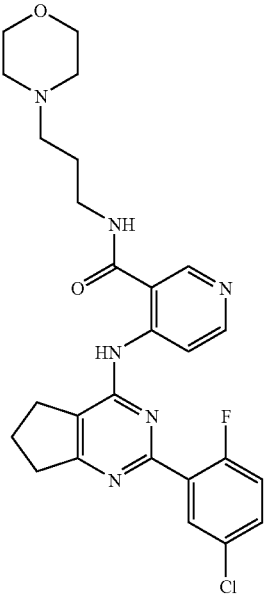 | 0.5288 |
| 71 | 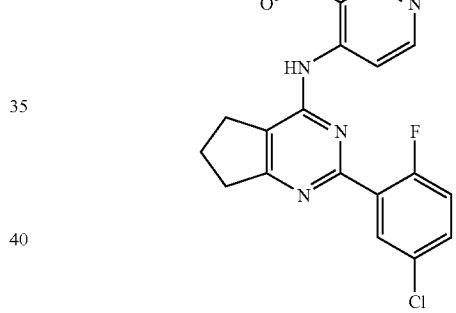 | 0.8438 |

-continued

| Compound # | Structure | IC$_{50}$ (µM) |
|---|---|---|
| 72 | | 6.4568 |
| 73 | | 0.3089 |
| 74 | | 0.1154 |
| 75 | 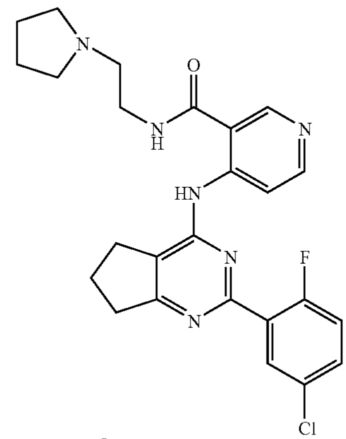 | 0.7124 |
| 76 | 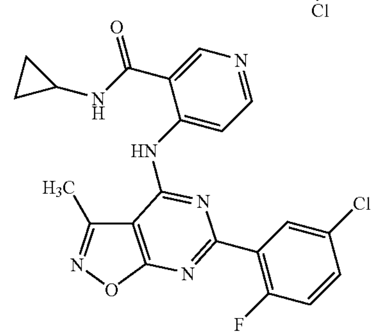 | NA |
| 77 | 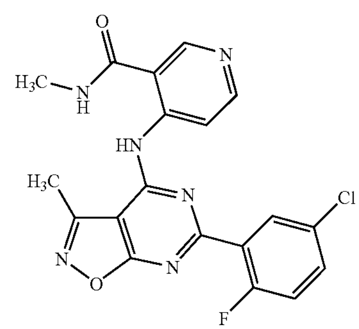 | NA |
| 78 | 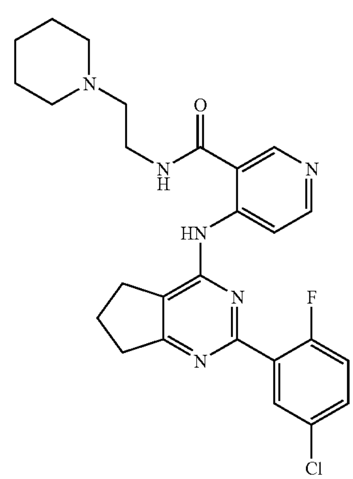 | 2.4636 |

-continued

| Compound # | Structure | IC$_{50}$ (μM) |
|---|---|---|
| 79 | 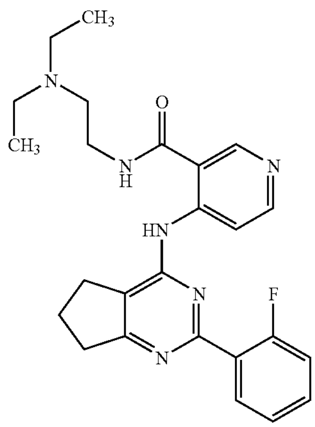 | 5.4852 |
| 80 | 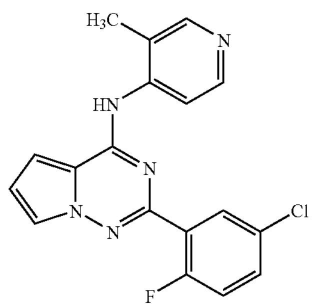 | 0.8491 |
| 81 | 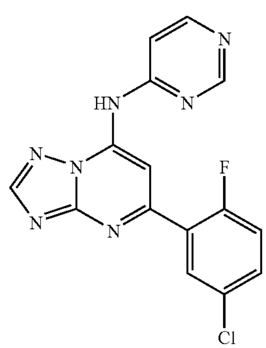 | NA |
| 82 | 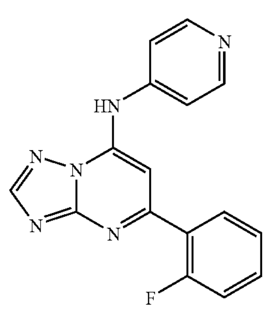 | 8.841 |

-continued

| Compound # | Structure | IC$_{50}$ (μM) |
|---|---|---|
| 83 | 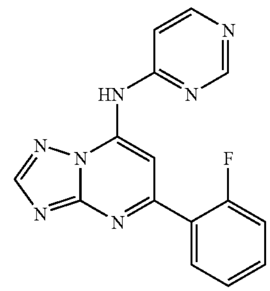 | 16.8519 |

Scheme A (Synthesis of Compounds 1 and 26):
This general scheme was used to prepare compounds 1 and 16.

Preparation of I 2.53 g, 4-amino-5-imidazolecarboxamide was dissolved in 30 mL chloroform and 30 mL dimethylformamide. To this solution was added at 0° C. 3.02 mL, 3-chlorobenzoylchloride, followed by 5.4 mL di-isopropylethylamine. The reaction mixture was allowed to warm to room temperature and maintained at room temperature overnight. The reaction mixture was diluted with chloroform and washed with water, 10% aqueous sodium carbonate solution and brine. The organic layer was dried over anhydrous sodium sulfate and filtered. The crude residue obtained after concentration was taken up in the minimal amount of chloroform and chromatographed on silica gel, using ethyl acetate, 5% methanol to give 4.81 g I.

Note: For the synthesis of compound 16, Methyl-4-amino-5-imidazolecarboxamide, was used.

Preparation of II 2.74 g I, was suspended in 75 mL ethanol, added 5 mL 10 N sodium hydroxide to the reaction mixture and the reaction mixture was refluxed for four hours. After cooling to room temperature the reaction mixture was concentrated to remove ethanol and then diluted with water. The solution was then acidified by the addition of 1 N hydrochloric acid, at 0° C., to pH 6.5. The white precipitate that formed was collected by filtration, washed with water and ether and dried under high vacuum to give 0.84 g II.

Preparation of III 0.84 g II, was suspended in 60 mL chloroform, to this suspension was added 1.1 mL thionyl chloride and 2 mL dimethylformamide. The resulting mixture was refluxed under nitrogen for three hours. The reaction mixture was cooled to room temperature and concentrated to a yellow residue. This residue was taken up in chloroform and ice was added to the reaction mixture. The cold solution was washed with 5% aqueous sodium bicarbonate solution and brine. The organic layer was dried over anhydrous sodium sulfate and filtered. After concentration, the residue that was obtained was treated with cold ethyl acetate. A white solid separates. This solid was filtered and washed with ethyl acetate, to give 0.46 g III.

Preparation of Compound 1

0.46 g III was dissolved in 10 mL dry dimethylformamide, to this was added 0.67 ml di-isopropylethylamine. The reaction mixture was heated to 60° C., and to this was added a solution of 0.21 g 4-aminopyridine. The reaction mixture was heated under reflux for one hour. After cooling to room temperature the reaction mixture was concentrated to a minimal volume and the product purified by preparative reverse phase HPLC, using a C18 Vydac® column, using a gradient of water, acetonitrile (both containing 0.1% trifluoroacetic acid). 15 mg compound 1 was obtained after lyophilization of fractions containing desired product. Analysis: $^1$H NMR dr$_6$ DMSO, LCMS, M$^+$323.

Preparation of Compound 26

Compound 26 was prepared according to the procedures outline in Scheme A, using N-1-phenyl-2-aminoimidazole-3-carboxamide and benzoyl chloride.

Scheme B (Synthesis of Compounds 3, 5–15 and 17):

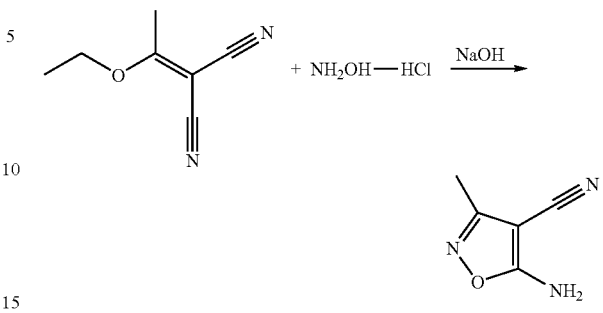

Preparation of 3-amino-4-cyano-5-methyl isoxazole

Hydroxylamine hydrochloride (12.78 g, 0.184 mole) was dissolved in 40 ml water, treated with sodium hydroxide (7.36 g, 0.184 mole). Added 60 ml ethanol (anhydrous) and while stirring (1-ethoxyethylidene)malonitrile (25 g, 0.184 mole) was added carefully. Heated the reaction mixture to 50° C. for 30 min, then stirred overnight at room temperature. Removed ethanol under vacuum, filtered solid product, washed with water, dried under vacuum to obtain 21.93 g (96.8% yield)

Note: For the synthesis of 7 and 11, the corresponding ethyl hydroxylarnine was used and for the synthesis of 9, the corresponding phenyl hydroxylamine was used.

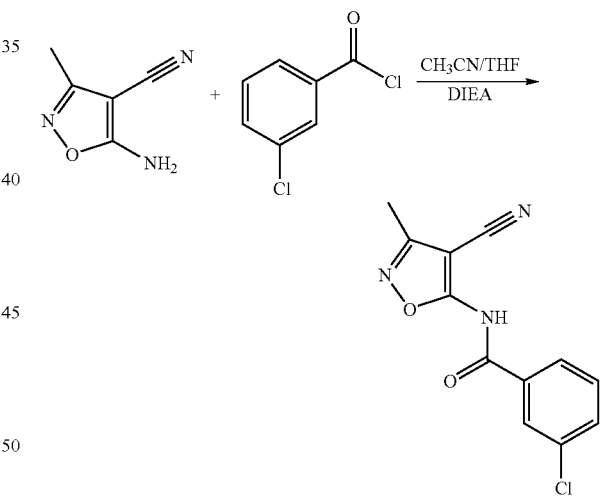

Preparation of
N-(3-chlorobenzoyl)-4-cyano-3-methyl-5-carboxamide 3-amino-4-cyano-5-methyl isoxazole (6.0 g, 0.0487 mole) was suspended in acetonitrile/tetrahydrofuran (30 ml/10 ml). Diisopropylethylamine (8.26 ml, 0.0487 mole) was added followed by dropwise addition of 3-chlorobenzoyl chloride. The mixture was stirred at room temperature overnight. The precipitated product was isolated by filtration, washed with chloroform. Obtained 1.31 g product (11% yield)

Note: For the synthesis of compounds 3,5,6,8,10,12,13,14,15 and 17, the corresponding acid chlorides were used.

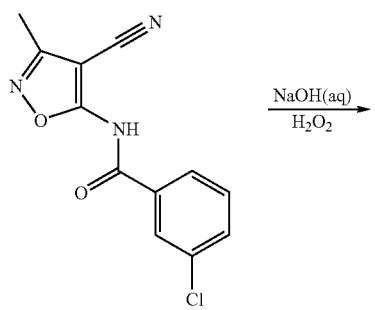

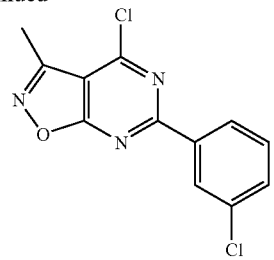

Preparation of 3-methyl-4-chloro-6-(3-chlorophenyl)isoxazole[5,4d]pyrimidine 3-methyl-6-(3-chlorophenyl)isoxazole[5,4d]pyrimidone (535 mg, 2.04 mmole) was suspended in phosphorus oxychloride (6 ml) and heated to reflux for 4 hours. Removed excess phosphorus oxychloride, added ice, chloroform (10 ml) basified with saturated sodium bicarbonate, extracted product into chloroform and dried extracts over sodium sulfate (anh). Purified product by silica gel chromatography eluting with chloroform. Obtain 200 mg product.

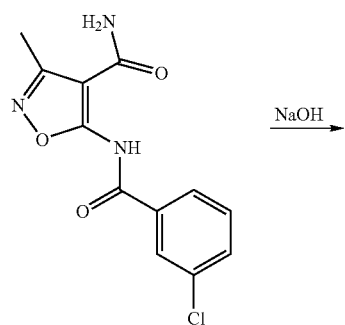

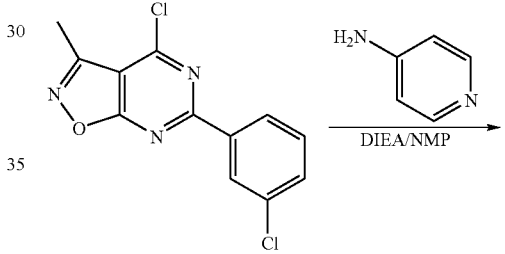

Preparation of 3-methyl-6-(3-chlorophenyl)isoxazole[5,4d]pyrimidone

N-(3-chlorobenzoyl)-4-cyano-3-methyl-5-carboxamide (1.0 g, 15 mmole) was suspended in 20 ml 1 M sodium hydroxide and treated with 8 ml 30% hydrogen peroxide. The mixture was refluxed overnight. The cooled reaction mixture was placed on an ice batch and treated with 1 M hydrochloric acid to pH 6. Filtered the product as a white precipitate and dried under vacuum to give 537 mg. (53% yield).

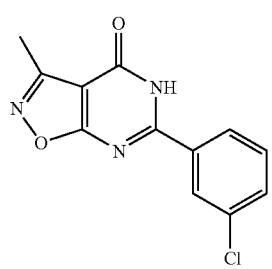

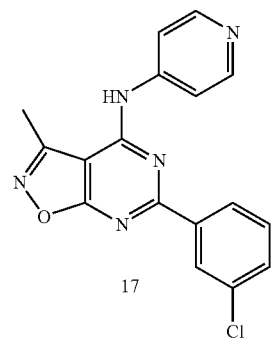

17

Preparation of 3-methyl-4-(4-aminopyridyl)-6-(3-chlorophenyl)isoxazole[5,4d]pyrimidine(17)

4-aminopyridine (80.6 mg, 0.859 mmole) was dissolved in N-methylpyrrolidone, diisopropylethylamine (149 microliters) was added followed by 3-methyl-4-chloro-6-(3-chlorophenyl)isoxazole[5,4d]pyrimidine (120 mg, 0.428 mmole). The mixture was heated to 50° C. with stirring for 1 hour. Product was purified by preparative HPLC on C18 column.

Scheme C (Synthesis of Compounds 2 and 4):

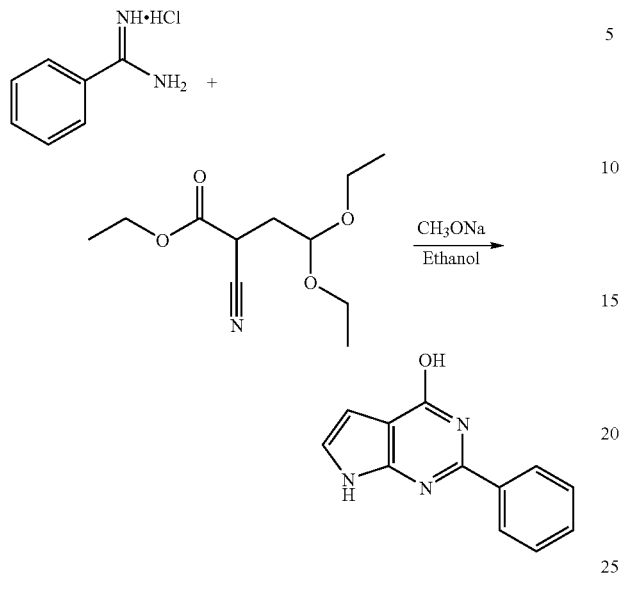

Preparation of 2-phenyl-pyrollo[2,3d]pyrimidone

Benzamidine hydrochloride (4.0 g, 0.25 mol) was dissolved in 64 ml of ethanol. To this 8.0 ml of a 25 wt % solution of sodium methoxide was added. Reaction was then stirred at room temperature for 0.5 hrs, and filtered. Filtrate was then added to ethyl-2-cyano-4,4-diethoxybutyrate (4.80 g, 0.21 mol). This solution was refluxed for 5 hrs. Half of solvent was removed under reduced pressure then 80 ml of ice water was added, and the pH was adjusted to 7 with acetic acid. Material was then chilled for 6 hrs and product was isolated by vacuum filtration.

Note: For the synthesis of compound 4,3-chlorobenzamidine was used.

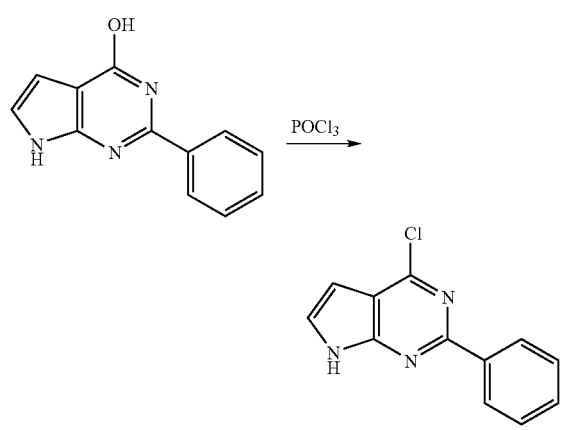

Preparation of 4-chloro-2-phenyl pyrollo[2,3d]pyrimidine 2-phenyl pyrollo[2,3d]pyrimidone (1.0 g 4.73 mmol) was treated with phosphorous oxychloride (7 ml, 27.7 mmol) and refluxed for 5 hrs. Excess phosphorous oxychloride was removed under reduced pressure and the extracted with chloroform, washed with sodium bicarbonate. Organic layer was dried over sodium sulfate(anh), then concentrated to dryness to give the product.

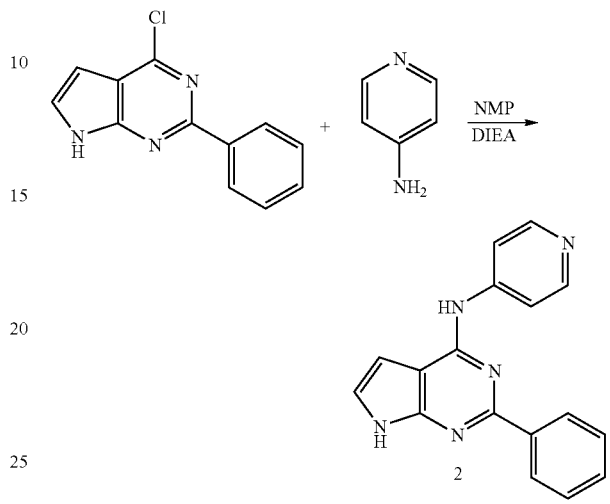

Preparation of 4-(4-aminopyridyl)-2-phenyl pyrollo[2,3d]pyrimidine(2)

4-chloro-2-phenyl pyrollo[2,3d]pyrimidine (0.12 g, 1.27 mmol) was dissolved in 4 ml of NMP. N,N'-Diisopropylethylamine (0.229 ml) was added followed by 4-aminopyridine (0.15 g, 0.635 mmol). Reaction mixture was heated to reflux for 2 hours, cooled and purified by preparative HPLC.

Scheme D (Synthesis of Compound 18):

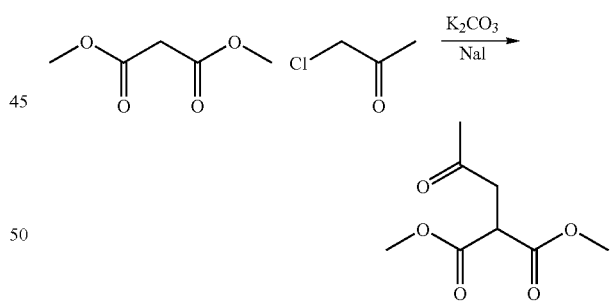

Preparation of Acetylmethyl-dimethylmalonate

Dimethyl malonate (5 g, 0.189 mole) was treated with potassium carbonate (34.78 g, 0.25 mole), sodium iodide (1.00 g, 0.0067 mole) and then warmed while chloroacteone (23.1 g, 0.25 mole) was added rapidly batchwise. The reaction mixture was heated to 1000° C. for 20 min. Cooled reaction mixture added 50 ml ethanol, filtered solid material washing with ethanol. Removed ethanol from filtrate under vacuum. Isolated product by vacuum distillation. Obtained product 11.26 g (32% yield).

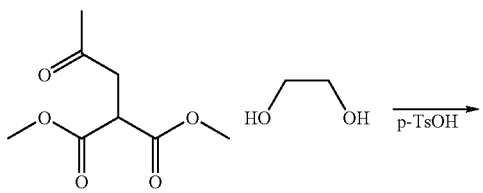

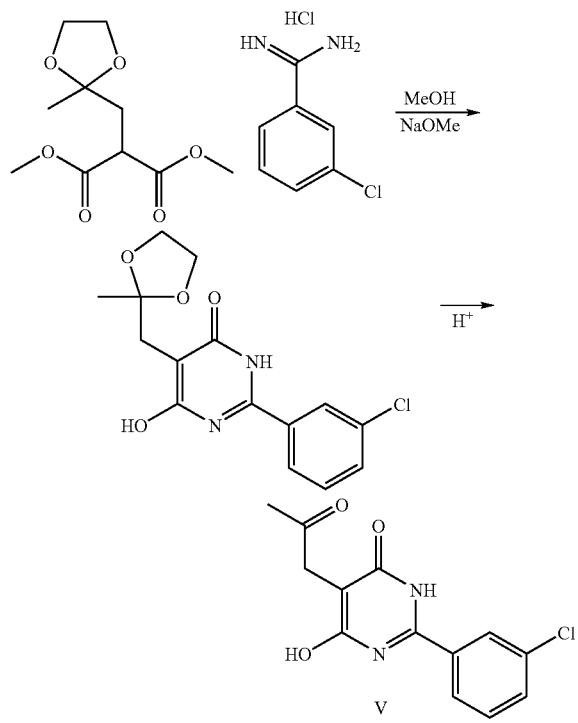

IV

Preparation of IV

Ethylene glycol (3.90 g, 0.0628 mole), the acetylmethyldimethylmalonate (11.26 g, 0.06 mole), p-toluene sulfonic acid (0.21 g, 0.0011 mole) were combined in 25 ml benzene. The reaction mixture was heated to reflux collecting water in a Dean Stark trap overnight. Washed reaction mixture with sodium 10% sodium bicarbonate (2×10 ml) dried benzene over sodium sulfate. Removed solvent to obtain product as an oil, 14.1 g.

V

Preparation of V

Protected dimethyl malonate derivative (5.0 g, 0.0215 mole) was dissolved in methanol (20 ml), added 3-chlorobenzamidine hydrochloride, followed by 25% sodium methoxide (16 ml, 0.0646 mole). The reaction mixture was stirred at room temperature for 3 days. Diluted mixture with water (50 ml) added 60 ml 1 M HCl stirred for 1 hour room temp, then added 4 ml concentrated HCl and stirred overnight, to give final product. Methanol was removed under vacuum, and product was obtained by filtration and vacuum drying. Obtained 5 g product.

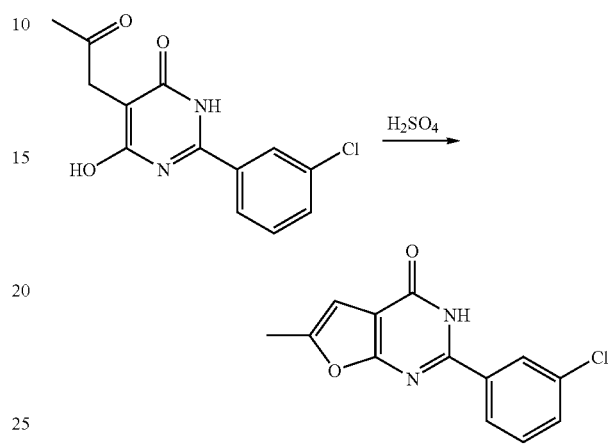

Preparation of 6-methyl-2-chlorophenyl-furano[3,2d]pyrimidone 6-hydroxy-5-acetylmethyl-2-(3-chlorophenyl)pyrimidone (5.0 g) was treated with concentrated sulfuric acid (80 ml). The reaction mixture was stirred at room temperature for 4 hours, then neutralized with sodium carbonate and extracted with chloroform, chloroform extract washed with water, dried over sodium sulfate (anh) and solvent removed to give product (1.10 g).

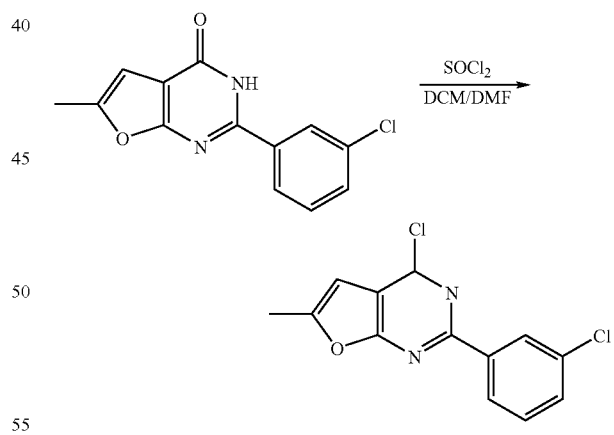

Preparation of 6-methyl4-chloro-2-chlorophenyl-furano[3,2d]pyrimidine 6-methyl-2-chlorophenyl-furano[3,2-d]pyrimidone (480 mg, 1.84 mmole) was suspended in dichloromethane (4 ml). Added thionyl chloride (1.6 ml, 22.5 mmole) and dimethylformamide (0.5 ml) and heated to reflux for 3 hours. Removed excess solvent, residue treated with ice, extracted into chloroform, washed with 10% sodium bicarbonate, water, dried sodium sulfate (anh) and solvent removed to give 480 mlg product.

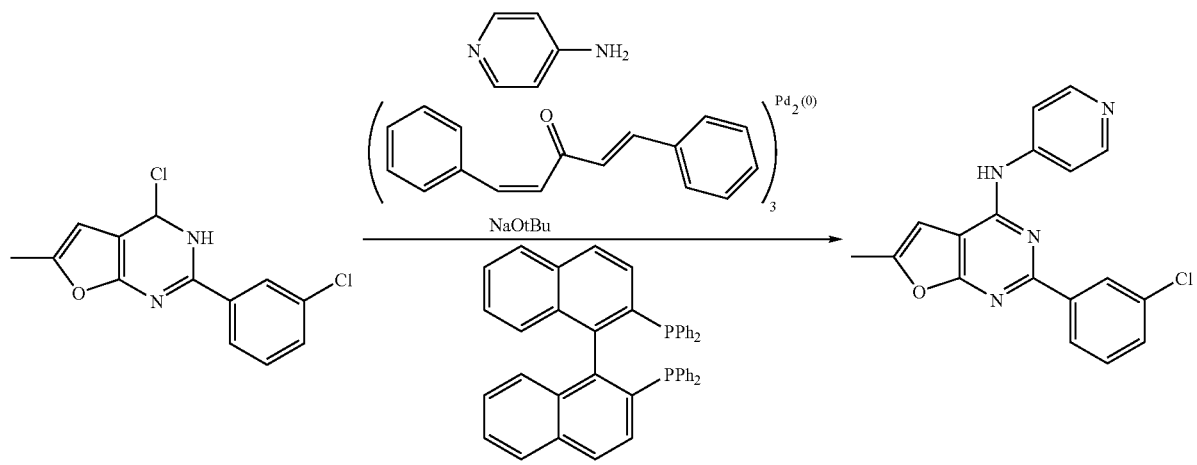

Preparation of 6-methyl4-(4-aminopyridyl)-2-chlorophenyl-furano[3,2d]pyrimidine (18)

6-methyl4-chloro-2-chlorophenyl-furano[3,2d]pyrimidine (480 mg, 1.72 mmole, 1 eq), BINAP (8 mg, 0.013 mmole, 0.0075 eq), Pd₂(dba)₃ (3.9 mg, 0.0043 mmole, 0.0025 eq), sodium t-butoxide (231 mg, 2.4 mmole, 1.4 eq), 4-aminopyridine (194 mg, 2.06 mmole, 1.2 eq) were combined in 5 ml dioxane and heated to 50° C. for 5 hours. Product was isolated by preparative HPLC on C18 column.

Scheme E. (Synthesis of compound 19)

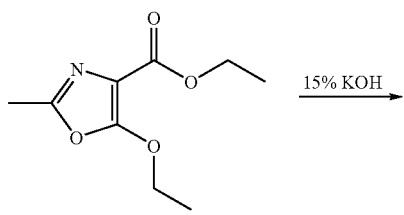

Preparation of Ethyl-2-methyl-5-ethoxy-4-oxazole-4-carboxylate

Diethyl Acetamidomalonate (15.0 g, 69.1 mmol) was dissolved in 60 ml of chloroform then treated with 60 g of phosphorous pentoxide. Reaction mixture was refluxed for 6 hours then cooled to room temperature. This solution was treated with Sodium hydroxide (1 M) to neutralize the reaction mixture. The organic layer was washed with water and dried over sodium sulfate(anh). Crude product was vacuum distilled to isolate product. 8.26 g 60% yield.

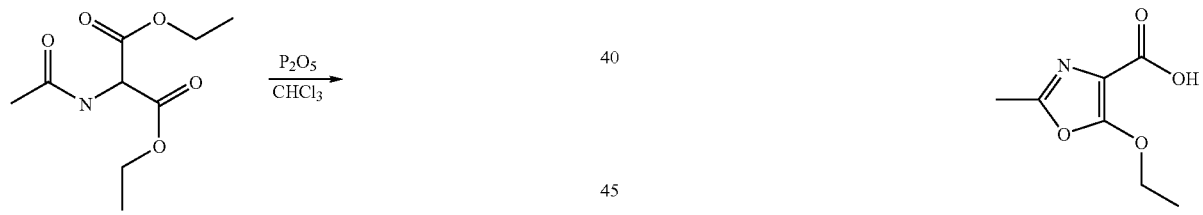

Preparation of 2-methyl-5-ethoxy-4-oxazole-4-carboxylic acid

Ethyl -2-methyl-5-ethoxy-4-oxazole-4-carboxylate (8.26 g, 41.5 mmol) was treated with 74 ml of a 15% solution of KOH. This was refluxed for 15 minutes then cooled and acidified using a 10% HCl solution. Product was collected by vacuum filtration.

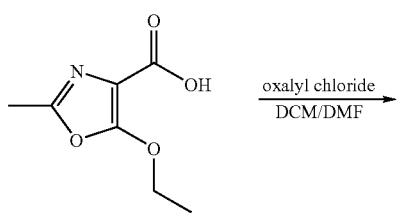

-continued

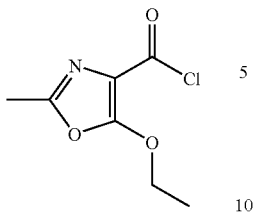

Preparation of
2-methyl-5-ethoxy-4-oxazole-4-carbonyl chloride 2-methyl-5-ethoxy-4-oxazole-4-carboxylic acid (2.56 g, 14.9 mmol) was dissolved in dichloromethane. Two drops of dimethylformamide was added and the reaction was cooled in an ice bath. Oxalyl chloride (12 ml, 22.3 mmol) was added dropwise. The ice bath was removed and the reaction was stirred at room temperature for 2 hours. Solvent was removed by reduced pressure.

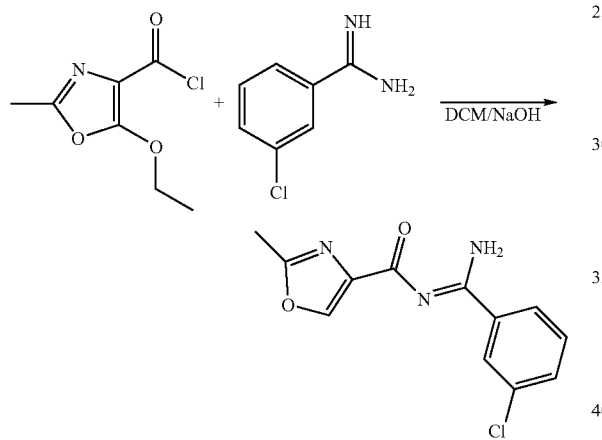

Preparation of 4-(3-chlorobenzamidinamide)-2-methyl-5-ethoxy-4-oxazole-4-carbonyl chloride 3-chlorobenzamidine (2.29 g, 14.8 mmol) was dissolved in 40 ml of DCM and brought to 0° C. A 15 ml 2.0 M solution of sodium hydroxide was then added. 2-methyl-5-ethoxy-4-oxazole-4-carbonyl chloride (2.8 g, 14.8 mmol), dissolved in 30 ml of DCM was added dropwise to the reaction mixture and stirred at room temperature for 3 hours. Organic solvent was then washed with water followed by sodium bicarbonate, then dried with sodium sulfate and concentrated.

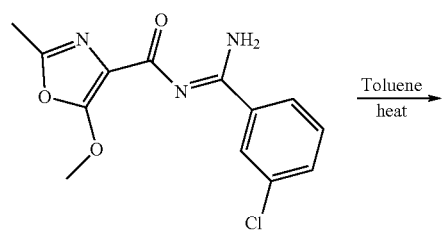

-continued

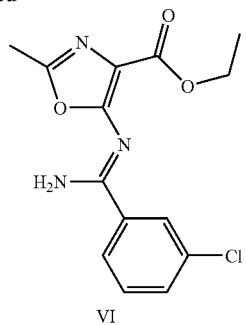

Preparation of VI 4-(3-chlorobenzamidinamide)-2-methyl-5-ethoxy-4-oxazole-4-carbonyl chloride (2.0 g, 6.5 mmol) was dissolved in 30 ml of toluene and refluxed for 1.5 hours. The solvent was then removed by reduced pressure.

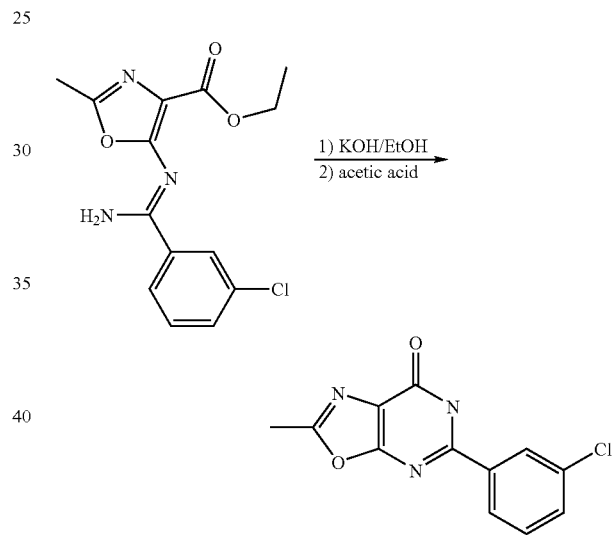

Preparation of 7-methyl-2-(3-chlorophenyl)-oxazolo[2,3d]pyrimidone 1.86 g, 5.93 mmol, of the oxazole ester was treated with 0.86 g, 15.4 mmol of KOH in 20 l of ethanol. This was stirred at room temperature overnight. The organic solvent was evaporated under reduced pressure and the compound was dissolved in water and acidified using a 15% solution of HCl. Solid product was collected by vacuum filtration.

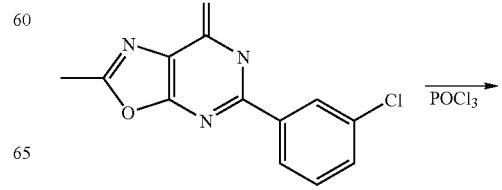

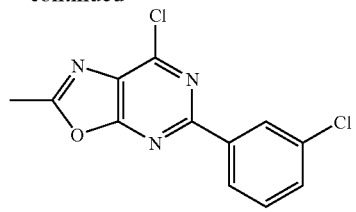

Preparation of 7-methyl-4-chloro-2-(3-chlorphenyl)-oxazolo[2,3d]pyrimidine 7-methyl-2-(3-chlorophenyl)-oxazolo[2,3d]pyrimidone (1.32 g, 5.06 mmol) was treated with phosphorus oxychloride (13.2 ml, 141.7 mmol and refluxed for three hours. Reaction was cooled, solvent was removed by reduced pressure and residue was taken up in chloroform. Ice was added to the organic solvent then organic solvent was washed with sodium bicarbonate, dried over sodium sulfate then concentrated. Crude product was purified by flash column chromatography.

Preparation of 7-methyl-4-(4-aminopyridyl)-2-(3-chlorophenyl)-oxazolo[2,3d]pyrimidine (19)

7-methyl-4-chloro-2-(3-chlorophenyl)-oxazolo[2,3d]pyrimidine (0.100 g, 0.358 mmol), 4-aminopyridine (0.040 g, 0.430 mmol), sodium t-butoxide (0.048 g, 0.501 mmol), Bis(diphenylphosphino)-1,1'-binaphthyl (0.0009 g, 0.0014 mmol), and Pd$_2$(dba)$_3$ (0.0004 g, 0.0043 mmol) were combined and dissolved in 2 ml of dry dioxane and refluxed for 3.5 hours. Reaction was cooled then filtered through celite, then purified by HPLC.

Scheme F

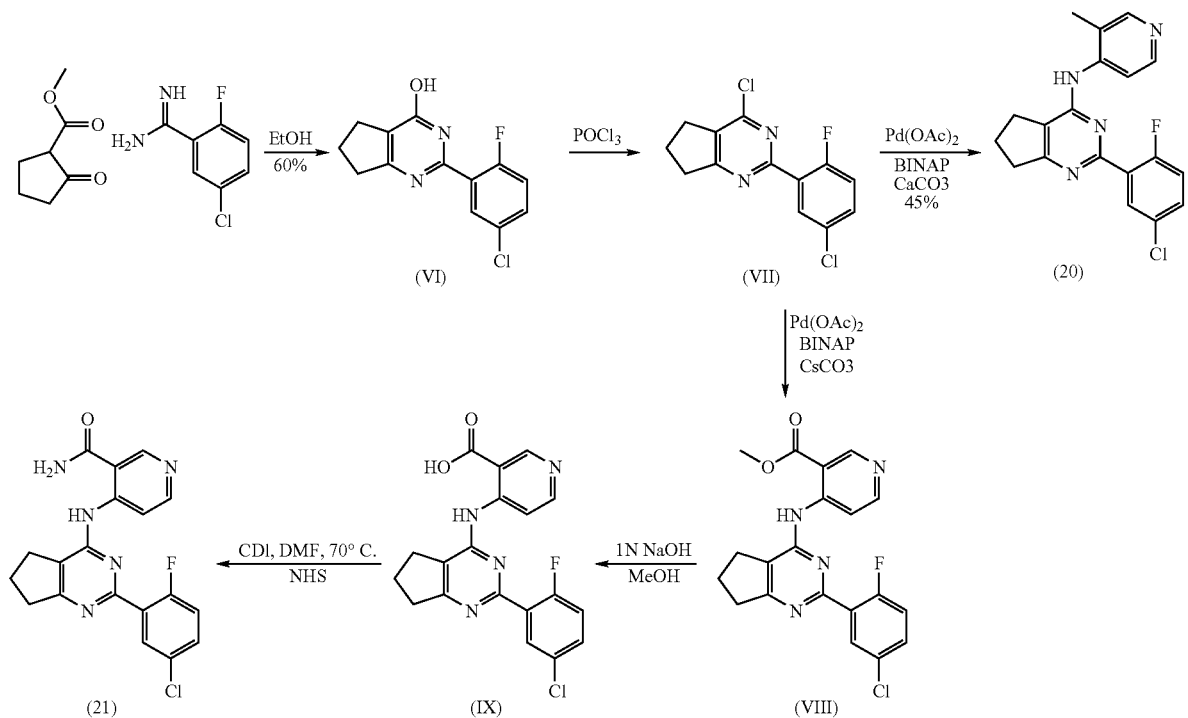

Preparation of VI

To a solution of methyl-2-oxocyclopentane carboxylate (4.10 g, 28.9 mmol, 1 eq), in dry ethanol (20 ml) was added a solution of 2-fluoro-5-chlorobenzamidine (5.0 g, 28.9 mmol, 1 eq) in ethanol (20 ml) and the reaction mixture was heated to 80° C overnight. The reaction mixture was cooled to r.t. and the white precipitate was filtered and washed with cold ethyl actetate (2×20 ml). The crude residue was partitioned between chloroform and water. The aqueous layer was acidified to pH 4 and the product was extracted with chloroform (3×50 ml). The organic layers were combined, washed with brine, dried over $MgSO_4$, filtered and concentrated in vacuo to give a crude white solid (VI) (4.5 g, 60%) which was not further purified.

Preparation of VII

A suspension of VI (200 mg, 0.757 mmol) in $POCl_3$ (5 ml) was stirred under reflux for 1 h. The solution was then cooled to room temperature and concentrated under reduced pressure to give a white solid which was dissolved in dry methylene chloride. The solution was cooled to 0° C. and ice was added followed by sat. $NaHCO_3$. The organic layer was separated, washed with brine, dried ($MgSO_4$), filtered and evaporated in vacuo to provide a crude white solid which was not further purified.

Preparation of 20: (General Buchwald Reaction Procedure)

The crude imino chloride VII (210 mg, 0.76 mmol, 1 eq) was dissolved in dioxane (5 ml) and to this was added $Pd(OAc)_2$ (9 mg, 0.04 mmol, 0.05 eq) followed by BINAP (35 mg, 0.056 mmol, 0.075 eq), 4-amino-3-picoline (82 mg, 0.760 mmol, 1 eq) and $Cs_2CO_3$ (370 mg, 1.13 mmol, 1.5 eq). The reaction mixture was heated to 80° C. for 15 h. The reaction mixture was cooled to r.t. and filtered through Celite® and the crude material was purified by flash column chromatography (3:2/ethyl acetate:hexane) to give 20 (110 mg, 41%).

Preparation of IX

To a suspension of VIII (100 mg, 0.25 mmol, 1 eq) in MeOH (5 ml) was added a 1 N $NaOH_{(aq)}$ solution (500 µl, 0.50 mmol, 2 eq) and the reaction mixture was refluxed for 2 h. The mixture was cooled to r.t. and concentrated in vacuo. Water (10 ml) was added to the crude material and the aqueous layer was acidified to pH 4. The solid was filtered, washed with water (2×5 ml) and dried overnight to give IX (50 mg, 52%) as a cream colored solid.

Preparation of 21

To a suspension of IX (50 mg, 0.13 mmol, 1 eq) in dry DMF (2 ml) was added 1-1'-carbonyldiimidazole (42 mg, 0.26 mmol, 2 eq) and the reaction mixture was warmed to 70° C. for 2h. The mixture was cooled to r.t. and $NH_{3(g)}$ was bubbled through for 10 min. The reaction mixture was stirred at r.t. for a further 1 h. The reaction was concentrated in vacuo. Water (10 ml) was added to the crude material and solid was filtered, washed with water (2×5 ml) and dried overnight to give 21 (30 mg, 60%) as a cream colored solid.

Additional Compounds prepared according to Scheme F

Compound 32 was prepared according o the procedure outlined in scheme F, for the preparation of compound (VIII), using 4-aminopyridine-3-carboxylic acid ethyl ester. Compound 36 was prepared by the method described for the synthesis of compound 20 employing 4-amino-3-trifluoromethyl-picoline in place of 4-amino-3-picoline. Compound 35 was prepared by the method described for the synthesis of compound 21 employing methyl amine in place of ammonia. Compound 37 was prepared by the method described for the synthesis of compound 21 employing pyrrolidine in place of ammonia. Compound 41 was prepared by the method described for the synthesis of compound 21 employing cyclopropylamine in place of ammonia. Compound 42 was prepared by the method described for the synthesis of compound 21 employing cyclopropylmethylamine in place of ammonia. Compound 51 was prepared by the method described for the synthesis of compound 21 employing 2-amino-ethanol in place of ammonia. Compound 52 was prepared by the method described for the synthesis of compound 21 employing 1-amino-propan-2-(S)-ol in place of ammonia. Compound 53 was prepared by the method described for the synthesis of compound 21 employing 3-amino-propane 1,2(S)-diol in place of ammonia. Compound 54 was prepared by the method described for the synthesis of compound 21 employing HO—$NH_2$ in place of ammonia. Compound 55 was prepared by the method described for the synthesis of compound 21 employing 1-amino-propan-2-(R)-ol in place of ammonia. Compound 56 was prepared by the method described for the synthesis of compound 21 employing N-methylethylenediamine in place of ammonia. Compound 58 was prepared by the method described for the synthesis of compound 21 employing hydrazine in place of ammonia. Compound 67 was prepared by the method described for the synthesis of compound 21 employing benzamidine. Compound 68 was prepared by the method described for the synthesis of compound 21 employing methylamine in place of ammonia and benzamidine in place of 2-F, 3-Cl-benzamidine. Compound 69 was prepared by the method described for the synthesis of compound 21 employing N,N'-dimethyl-1,3-propanediamine in place of ammonia. Compound 70 was prepared by the method described for the synthesis of compound 21 employing 4-(3-aminopropyl)morpholine in place of ammonia. Compound 71 was prepared by the method described for the synthesis of compound 21 employing 1-(3-aminopropyl)imidazole in place of ammonia. Compound 72 was prepared by the method described for the synthesis of compound 21 employing 1-(3-aminopropyl)-2-pyrrolidinone in place of ammonia. Compound 73 was prepared by the method described for the synthesis of compound 21 employing 2-(2-aminoethyl)-1-methylpyrrolidine in place of ammonia. Compound 74 was prepared by the method described for the synthesis of compound 21 employing 1-(3-aminopropyl)-2-pipecoline in place of ammonia. Compound 75 was prepared by the method described for the synthesis of compound 21 employing 1-(2-aminoethyl)pyrrolidine in place of ammonia. Compound 78 was prepared by the method described for the synthesis of compound 21 employing 1-(2-aminoethyl)piperdine in place of ammonia. Compound 79 was prepared by the method described for the synthesis of compound 21 employing N,N-diethylethenediamine in place of ammonia.

Scheme G (Synthesis of Compounds 22, 24, 25, and 30)

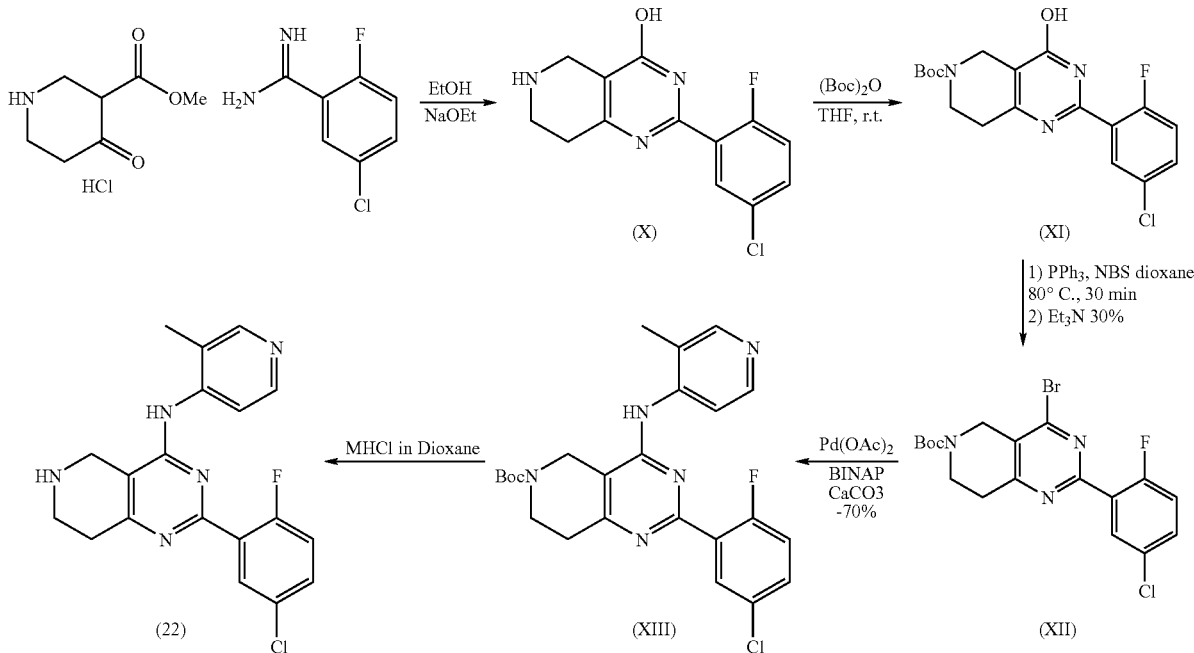

Preparation of X

To a solution of 2-fluoro-5-chlorobenzamidine (1.79 g, 10.4 mmol, 1 eq) in EtOH (10 ml) was added solid NaOEt (705 mg, 10.4 mmol, 1 eq) followed by methyl-4-oxo-3-piperidine carboxylate.HCl (2.0 g, 10.4 mmol, 1 eq). The reaction mixture was heated to 70° C. for 2 h then cooled to r.t. The precipitate was filtered and washed with ethyl acetate (2×20 ml) to give a white solid which (2.2 g, 76%) was not further purified.

Preparation of XI

To a suspension of X (300 mg, 1.08 mmol, 1 eq) in dry THF (10 ml) was added a solution of $Boc_2O$ (258 mg, 1.18 mmol, 1.1 eq) in dry THF (10 ml) at r.t. The reaction mixture was stirred at r.t. for 2 h and then the solution was concentrated in vacuo to give a crude residue which was purified by flash column chromatography to give XI (320 mg, 79%) as a white solid.

Preparation of XII

To a solution of $PPh_3$ (813 mg, 3.03 mmol, 5 eq) in dry dioxane (20 ml) was added NBS (540 mg, 3.03 mmol, 5 eq) at once and the suspension was stirred at r.t. for 30 min. A solution of XI (230 mg, 0.61 mmol, 1 eq) in dry dioxane (5 ml) was added and the reaction mixture was heated to 80° C. for 45 min. The reaction mixture was cooled to r.t. and $Et_3N$ (160 µl, 1.21 mmol, 2 eq). The mixture was concentrated in vacuo and the crude residue was purified by flash column chromatography 1:9 ethyl acetate:hexane to give XII (72 mg, 30%).

Preparation of XIII

To a solution of XII (72 mg, 0.16 mmol, 1 eq) in dry dioxane (2 ml) was added $Pd(OAc)_2$ (2 mg, 0.008 mmol, 0.05 eq) followed by BINAP (8 mg, 0.001 mmol, 0.075 eq), 4-amino-3-picoline (18 mg, 0.16 mmol, 1 eq) and $Cs_2CO_3$ (80 mg, 0.24 mmol, 1.5 eq). The reaction mixture was heated to 80° C. for 15 h. The reaction mixture was cooled to r.t. and filtered through Celite® and the crude material was purified by flash column chromatography (7:3/ethyl acetate:hexane) to give XIII (65 mg, 85%).

Preparation of 22

To a solution of XIII (65 mg, 0.14 mmol, 1 eq) in dry dioxane (2 ml) was added a 4 M HCl solution in dioxane (1 ml). The resultant suspension was stirred at r.t. for 2 h. The precipitate was filtered and washed with chloroform (1×5 ml), ethyl acetate (1×5 ml) and cold methanol (1×2 ml) to give 22 (35 mg, 68%) as a white solid.

Preparation of 24

Compound 24 was prepared according to the procedure outlined in scheme G, using ethyl 1-benzyl-4-oxopiperidine-3-carboxylate and benzamidine.

Preparation of 25

Compound 25 was prepared according to the procedure outlined in scheme G, using benzamidine.

Preparation of 30

Compound 30 was prepared according to the procedure outlined in scheme G, using ethyl 1-benzyl-4-oxopiperidine-3-carboxylate.

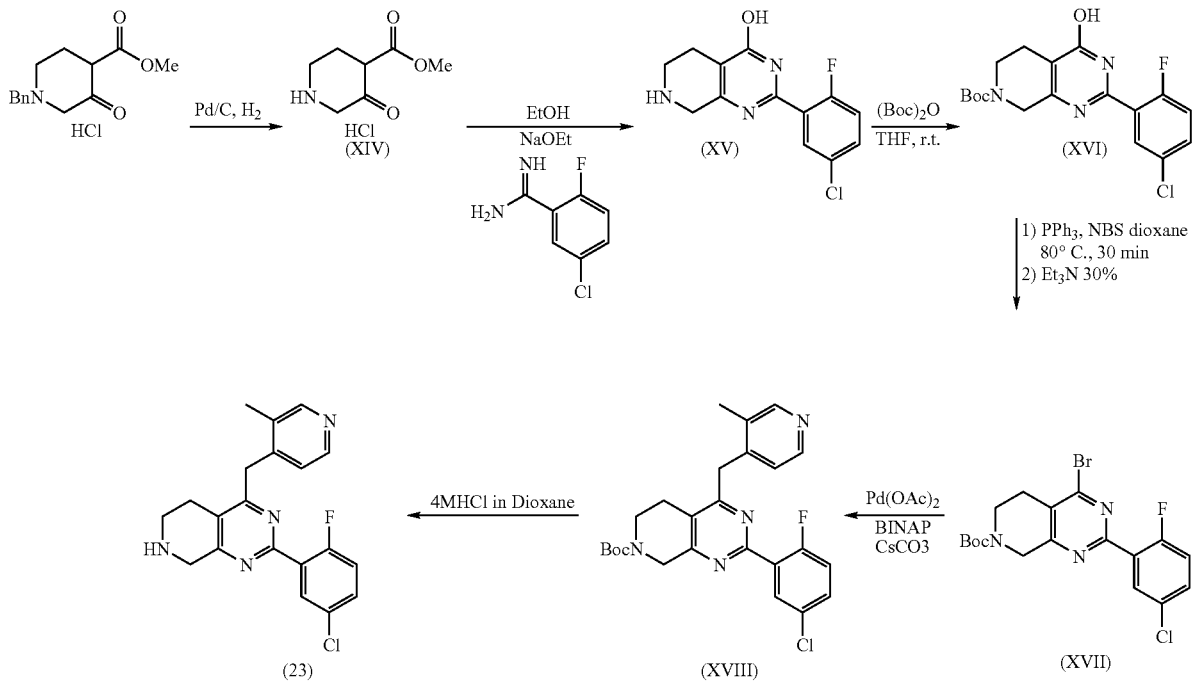

Scheme H (Synthesis of Compound 23)

Preparation of XIV

To a solution of ethyl-N-benzyl-3-oxo-4-piperdine carboxylate.HCl (2 g, 6.73 mmol, 1 eq) in ethanol (60 ml) was added 10% Pd/C. The air was evacuated and replaced with hydrogen via a balloon. The reaction mixture was left to stir at r.t. for 4 h. The reaction mixture was filtered through a short pad of Celite® to give XIV which was not further purified.

Preparation of XV

To a solution of 2-fluoro-5-chlorobenzamidine (1.16 g, 6.71 mmol, 1 eq) in EtOH (10 ml) was added solid NaOEt (457 mg, 6.71 mmol, 1 eq) followed by XIV (1.39 g, 6.71 mmol, 1 eq). The reaction mixture was heated to 70° C. for 2 h and then cooled to r.t. The precipitate was filtered and washed with ethyl acetate (2×20 ml) to give XV (1.12 g, 60%) as a white solid which was not further purified.

Preparation of XVI

To a suspension of crude XV (1.12 mg, 4.01 mmol, 1 eq)in dry THF (10 ml) was added a solution of Boc$_2$O (960 mg, 4.42 mmol, 1.1 eq) in dry THF (10 ml) at r.t. The reaction mixture was stirred at r.t. for 2 h and then the solution was concentrated in vacuo to give a crude residue which was purified by flash column chromatography to give XVI (750 mg, 50%) as a white solid.

Preparation of XVII

To a solution of PPh$_3$ (2.28 g, 8.70 mmol, 5 eq) in dry dioxane (20 ml) was added NBS (1.55 mg, 8.71 mmol, 5 eq) at once and the suspension was stirred at r.t. for 30 min. A solution of XVI (660 mg, 1.74 mmol, 1 eq) in dry dioxane (5 ml) was added and the reaction mixture was heated to 80° C. for 45 min. The reaction mixture was cooled to r.t. and 2 eq of Et$_3$N were added. The mixture was concentrated in vacuo and the crude residue was purified by flash column chromatography 1:9 ethyl acetate:hexane to give XVII (230 mg, 30%).

Preparation of XVIII

To a solution of XVII (230 mg, 0.52 mmol, 1 eq) in dry dioxane (5 ml) was added Pd(OAc)$_2$ (6 mg, 0.03 mmol, 0.05 eq) followed by BINAP (8 mg, 0.004 mmol, 0.075 eq), 4-amino-3-picoline (67 mg, 0.62 mmol, 1.2 eq) and Cs$_2$CO$_3$ (271 mg, 0.83 mmol, 1.5 eq). The reaction mixture was heated to 80° C. for 15 h. The reaction mixture was cooled to r.t. and filtered through Celite® and the crude material was purified by flash column chromatography (9:1/ethyl acetate:hexane) to give XVIII (38 mg, 16%).

Preparation of 23

To a solution of XVIII (38 mg, 0.08 mmol, 1 eq) in dry dioxane (2 ml) was added a 4 M HCl solution in dioxane (1 ml). The resultant suspension was stirred at r.t. for 2 h. The precipitate was filtered and washed with chloroform (1×3 ml), ethyl acetate (1×3 ml) and cold methanol (1×1 ml) to give 23 (32 mg, 95%) as a white solid.

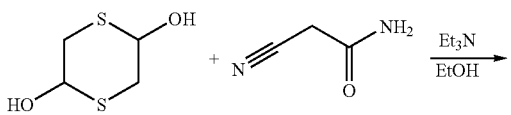

Scheme I (Synthesis of Compound 27)

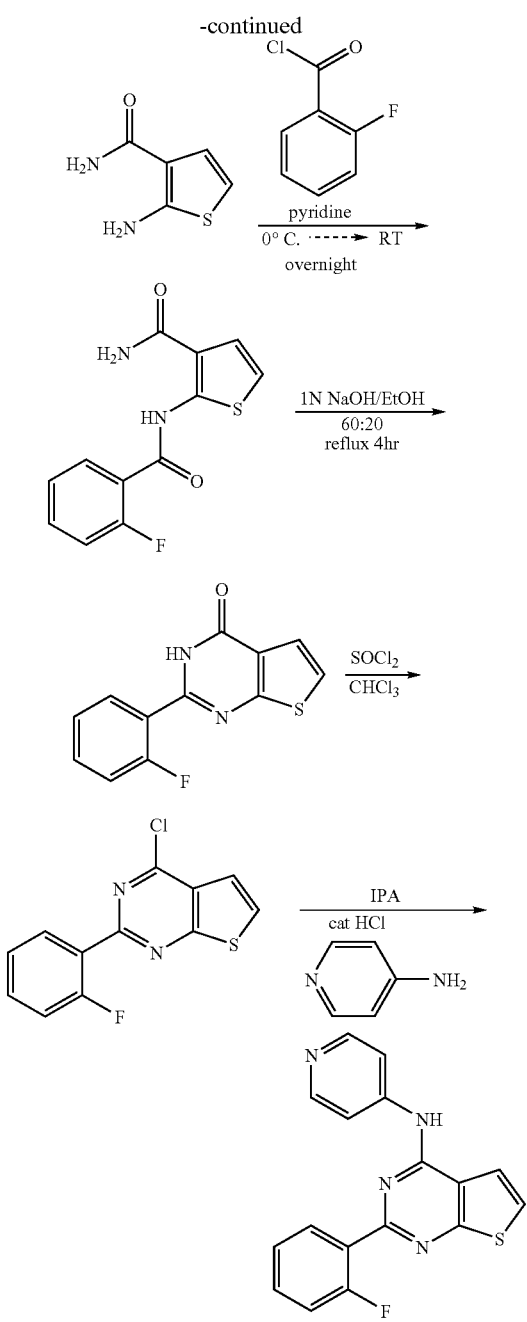

and 2-fluorobenzoyl chloride was added dropwise over 20 min, then reaction was allowed to warm to room temperature with stirring overnight. The pyridine was removed under vacuum, added dichloromethane and water. Product precipitated as a grey solid and was washed with dilute hydrochloric acid, water and air dried. The dichloromethane layer was separated, washed with dilute hydrochloric acid, and water, dried over sodium sulfate (anh.) and solvent removed to give a total of 12.45 g product (77% yield).

2-(2-Fluoro-phenyl)-3H-thieno[2,3-d]pyrimidin-4-one 2-(2-Fluoro-benzoylamino)-thiophene-3-carboxylic acid amide (8.56 g, 32.4 mmole) was dissolved in a mixture of 20 ml 1M sodium hydroxide and 60 ml ethanol. The mixture was brought to reflux for 4 hours. Cooled reaction mixture and poured onto ice. Acidified solution with dilute hydrochloric acid and isolated the product by filtration. Upon vacuum drying obtained 5.42 g product (Yield: 68%).

4-Chloro-2-(2-fluoro-phenyl)-thieno[2,3-d]pyrimidine 2-(2-Fluoro-phenyl)-3H-thieno[2,3-d]pyrimidin-4-one (900 mg, 3.65 mmole) was dissolved in chloroform and thionyl chloride (0.532 ml, 7.30 mmole) was added to the mixture followed by 1 ml dimethylformamide. Heated the reaction mixture to reflux for 2.5 hours, the cooled mixture was washed with 10% sodium carbonate, dried the chloroform solution over sodium sulfate (anh) and removed solvent. The crude product was chromatographed on silica gel, eluting with chloroform. Upon removal of solvent obtained 438 mg product (yield: 45%).

[2-(2-Fluoro-phenyl)-thieno[2,3-d]pyrimidin-4-yl]-pyridin-4-yl-amine

4-Chloro-2-(2-fluoro-phenyl)-thieno[2,3-d]pyrimidine (110 mg, 0.41 mmole) and 4-aminopyridine (78 mg, 0.830 mmole) were combined in isopropanol (3 ml), added 4 drops 4M HCl/dioxane and heated the reaction mixture to 80° C. for 7 hours. The reaction mixture was cooled and product isolated by filtration, washed with minimum cold methanol and dried under vacuum to give 116 mg product (yield: 86%).

2-Amino-thiophene-3-carboxylic acid amide 1,4-dithian-2,5-diol (4.56 g, 30 mmole) and 2-cyanoacetamide (2.52 g, 30 mmole) were combined in ethanol (50 ml). Added triethylamine (6 ml) and heated to 70° C. for 1 hour. Reduced the volume of solvent under vacuum, and isolated product by filtration. Product was recrystallized from ethanol to give 2.71 g product. (yield 64%).

2-(2-Fluoro-benzoylamino)-thiophene-3-carboxylic acid amide

2-Amino-thiophene-3-carboxylic acid amide (8.73 g, 61.4 mmole) was dissolved in pyridine (100 ml) cooled to 0° C.

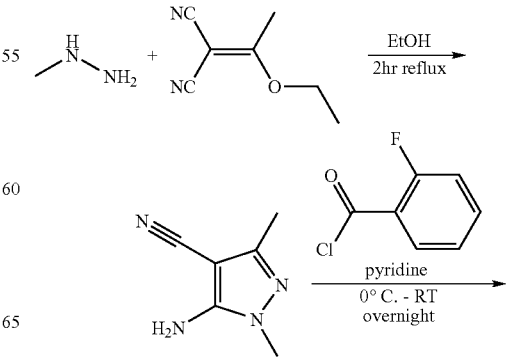

Scheme J (Synthesis of Compound 28)

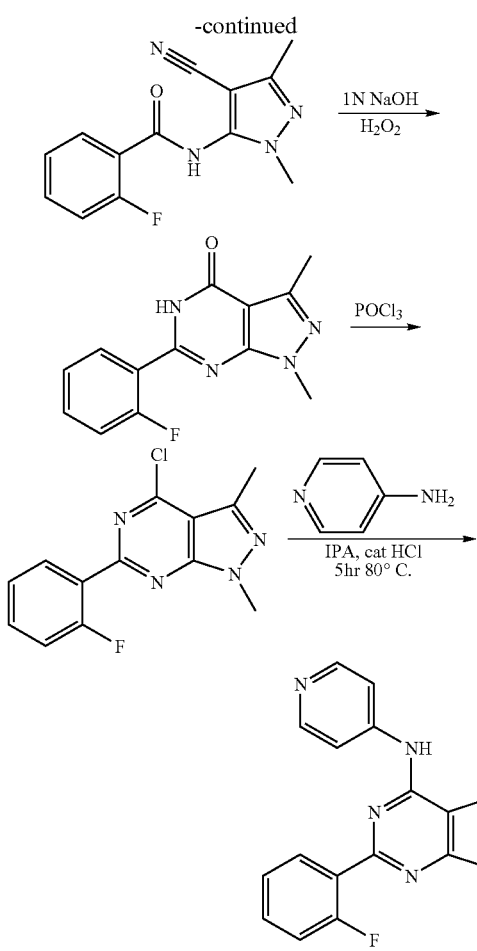

5-Amino-1,3-dimethyl-1H-pyrazole-4-carbonitrile

Methylhydrazine (5 g, 108.5 mmole) was added dropwise to a solution of (1-Ethoxyethylidene)-malonitrile (14.7 g, 108.5 mmole) in 250 ml ethanol. The mixture was then heated to reflux for 2.5 hours. The reaction mixture was allowed to cool, volume reduced to about 70 ml and product isolated by filtration, washed with cold ethanol and dried to obtain 13.5 g product (yield: 91%).

N-(4-Cyano-2,5-dimethyl-2H-pyrazole-3-yl)-2-fluoro-benzamide

5-Amino-1,3-dimethyl-1H-pyrazole-4-carbonitrile (10 g, 73.4 mmole) was suspended in pyridine (90 ml) and 2-fluorobenzoyl chloride was added dropwise while cooling reaction mixture on an ice bath. Stirred reaction mixture overnight at room temperature. Removed most of the pyridine and added 100 ml cold water to precipitate the product. Isolated product by filtration, washed with cold water, small amount of cold ethanol and dried under vacuum to obtain 9.15 g product (yield: 50%).

6-(2-Fluoro-phenyl)-1,3-dimethyl-1,5-dihydro-pyrazolo[3,4-d]pyrimidin-4-one

N-(4-Cyano-2,5-dimethyl-2H-pyrazol-3-yl)-2-fluoro-benzamide (5.0 g, 19.36 mmole) was suspended in 38 ml 1M sodium hydroxide and heated to 90° C. for 3 hours followed by addition of 30% hydrogen peroxide (10 ml) and further heating overnight. Cooled reaction mixture to room temperature and acidified with dilute hydrochloric acid. Product was isolated by filtration, washed with water, and dried overnight under vacuum to obtain 3.39 g product. (Yield 67%).

4-Chloro-6-(2-fluoro-phenyl)-1,3-dimethyl-1H-pyrazolo[3,4-d]pyrimidine 6-(2-Fluoro-phenyl)-1,3-dimethyl-1,5-dihydro-pyrazolo[3,4-d]pyrimidin-4-one (2.0 g, 7.74 mmole) was treated with 40 ml phosphorous oxychloride and heated to reflux overnight. Removed excess phosphorous oxychloride under vacuum and added ice water to the residue. Extracted product with ethyl acetate, washed with 10% sodium carbonate, water, dried over sodium sulfate (anh) and removed solvent to give crude product. Crude product was chromatographed on silica gel column eluting with chloroform to give 1.10 g pure product (yield: 51%).

[6-(2-Fluoro-phenyl)-1,3-dimethyl-1H-pyrazolo[3,4-d]pyrimidin-4-yl]-pyridin-4-yl-amine 4-Chloro-6-(2-fluoro-phenyl)-1,3-dimethyl-1H-pyrazolo[3,4-d]pyrimidine (84 mg, 0.304 mmole) and 4-aminopyridine (57 mg, 0.608 mmole) were combined in 4 ml isopropanol, added 3 drops 4M HCl/dioxane and heated reaction mixture to 80° C. for 5 hours. Cooled reaction mixture and filtered product to obtain 83 mg after vacuum drying (yield: 81%).

Scheme K (Synthesis of Compound 29)

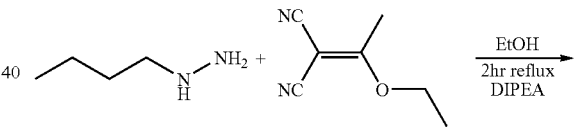

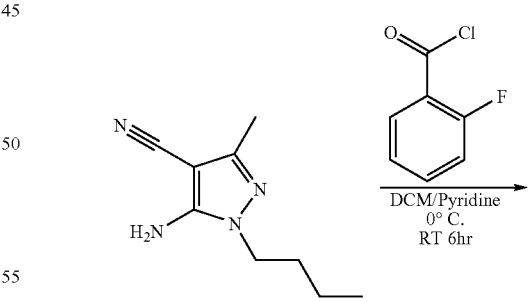

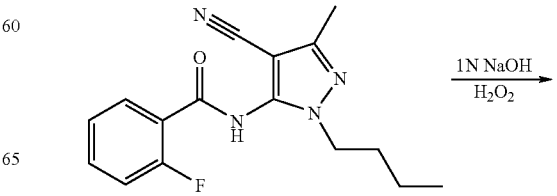

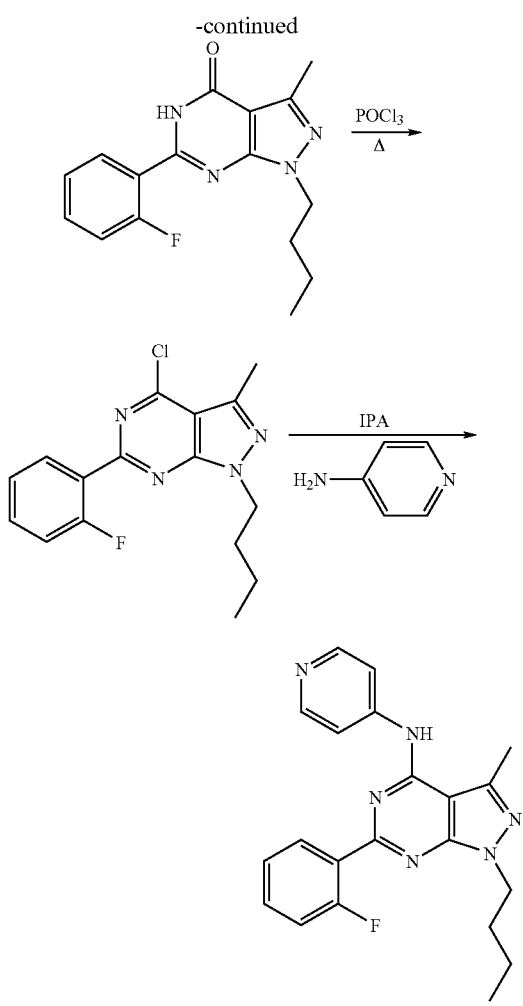

5-Amino-1-butyl-3-methyl-1H-pyrazole-4-carbonitrile

Butylhydrazine oxalate (14.25 g, 80 mmole) and (1-Ethoxyethylidine)-malonitrile (10.82 g, 80 mmole) were combined in ethanol (200 ml) the mixture treated with diisopropylethylamine (10.39 g, 80 mmole). The mixture was refluxed for 2 hours, then stirred at room temperature overnight. Removed most of the solvent under vacuum and triturated with chloroform, filtered some solid, kept chloroform filtrate. Washed chloroform filtrate with water, dried over sodium sulfate (anh) and removed solvent to give the product as a solid, 13.13 g (yield: 74%).

N-(2-Butyl-4-cyano-5-methyl-2H-pyrazol-3-yl)-2-fluoro-benzamide

5-Amino-1-butyl-3-methyl-1H-pyrazole-4-carbonitrile (10.0 g, 56 mmole) was dissolved in a mixture of dichloromethane/pyridine (45 ml/15 ml) and cooled to 0° C. 2-fluorobenzoyl chloride (8.87 g, 56 mmole) was added dropwise and reaction mixture stirred for 1 hour at 0° C., the at room temperature overnight. Removed solvent under vacuum. Residue was taken up in ethyl acetate, washed with dilute hydrochloric acid, 0.1M sodium hydroxide, water and dried over sodium sulfate (anh). Removed solvent and triturated solid in 30% ethyl acetate/hexanes. Filtered product to obtain 4.16 g product (yield: 24%).

1-Butyl-6-(2-fluoro-phenyl)-3-methyl-1,5-dihydro-pyrazolo[3,4-d]pyrimidin-4-one

N-(2-Butyl-4-cyano-5-methyl-2H-pyrazol-3-yl)-2-fluoro-benzamide (4.0 g, 13.3 mmole) was suspended in 26 ml 1M sodium hydroxide, added 30% hydrogen peroxide (10 ml) and ethanol (5 ml). Heated the reaction mixture to reflux for 4 hours, then added more 30% hydrogen peroxide (10 ml) and heated to reflux overnight. Cooled reaction mixture and acidified with dilute hydrochloric acid to pH 6.0. Collected product by filtration and dried under vacuum to obtain 1.29 g product (yield: 32%).

1-Butyl-4-chloro-6-(2-fluoro-phenyl)-3-methyl-1H-pyrazolo[3,4-d]pyrimidine

1-Butyl-6-(2-fluoro-phenyl)-3-methyl-1,5-dihydro-pyrazolo[3,4-d]pyrimidin-4-one (1.23 g, 4.1 mmole) was dissolved in phosphorous oxychloride (15 ml) and heated to reflux overnight. Removed excess phosphorous oxychloride under vacuum, treated residue with ice water, extracted product into ethyl acetate, washed with water, sat'd sodium chloride, dried over sodium sulfate (anh.) and removed solvent to give crude product. Chromatographed product on silica gel eluting with chloroform to give 723 mg purified product (yield: 55%).

[1-Butyl-6-(2-fluoro-phenyl)-3-methyl-1H-pyrazolo[3,4-d]pyrimidin-4-yl]-pyridin-4-yl-amine 1-Butyl-4-chloro-6-(2-fluoro-phenyl)-3-methyl-1H-pyrazolo[3,4-d]pyrimidine (100 mg, 0.31 mmole) and 4-aminopyridine (58 mg, 0.626 mmole) were combined in ethyleneglycol dimethoxy ether and heated to reflux for 4 hours. Cooled reaction mixture and isolated product by filtration, washed with minimum cold solvent and dried to give 132 mg product. 50 mg of this material was subjected to HPLC purification on reversed phase C18 column, eluting with gradient of water/acetonitrile/0.1% trifluoroacetic acid).

Scheme L (Synthesis of Compound 9)

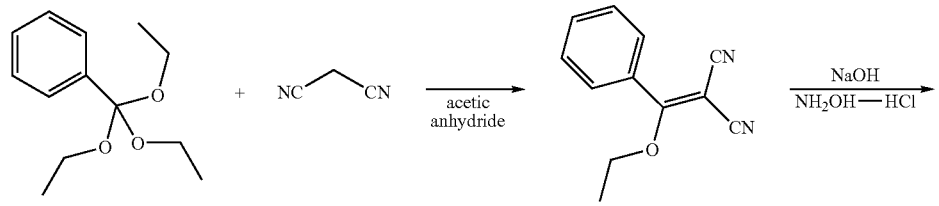

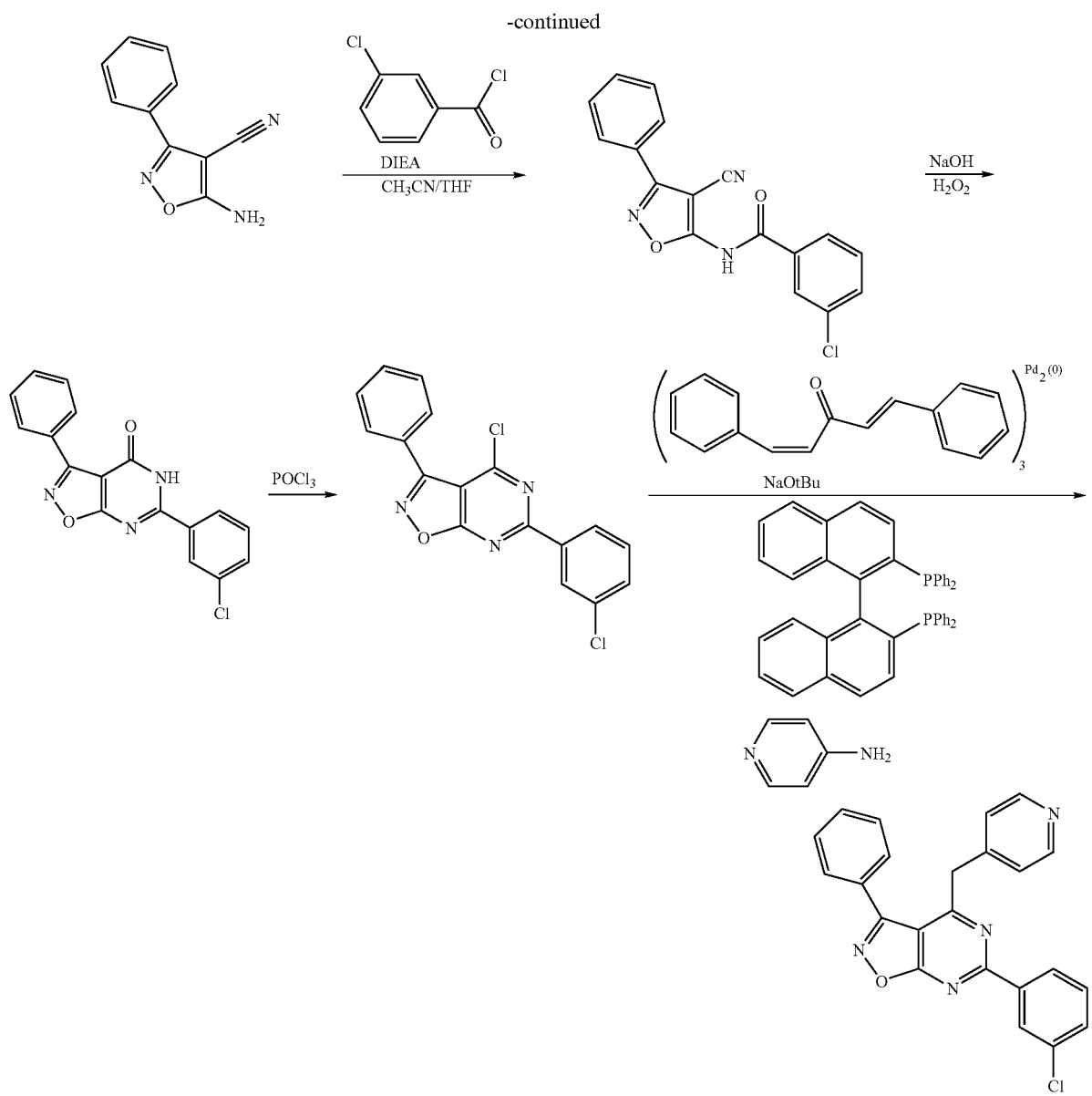

2-(Ethoxy-phenyl-methylene)-malononitrile

Triethylorthobenzoate (25 g, 0.112 mole), malonitrile (9.07 g, 0.137 mole and acetic anhydride (50 ml) were brought to reflux overnight. Removed excess acetic anhydride under vacuum and chromatographed product over silica gel eluting with 30% ethylacetate/hexanes to give 21.7 g product (yield: 97%).

5-Amino-3-phenyl-isoxazole-4-carbonitrile

Hydroxylamine hydrochloride was suspended in water (30 ml) and added sodium hydroxide (4.4 g, 0.11 mole), then ethanol (40 ml) followed by batchwise addition of 2-(Ethoxy-phenyl-methylene)-malononitrile(21.7 g, 0.11 mole). Heated reaction mixture to 50° C. for 2 hours. Removed ethanol under vacuum and filtered precipitate. Redissolved precipitate in 50% ethyl acetate/hexanes and chromatographed on silica gel to give 8.2 g product after removal of solvent (yield: 40%).

Rest of sequence made by analogy to the methyl replacement of phenyl analog.

Scheme M (Synthesis of Compound 80)

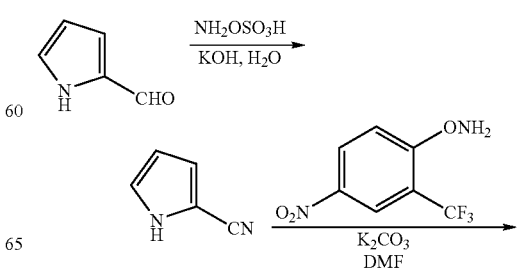

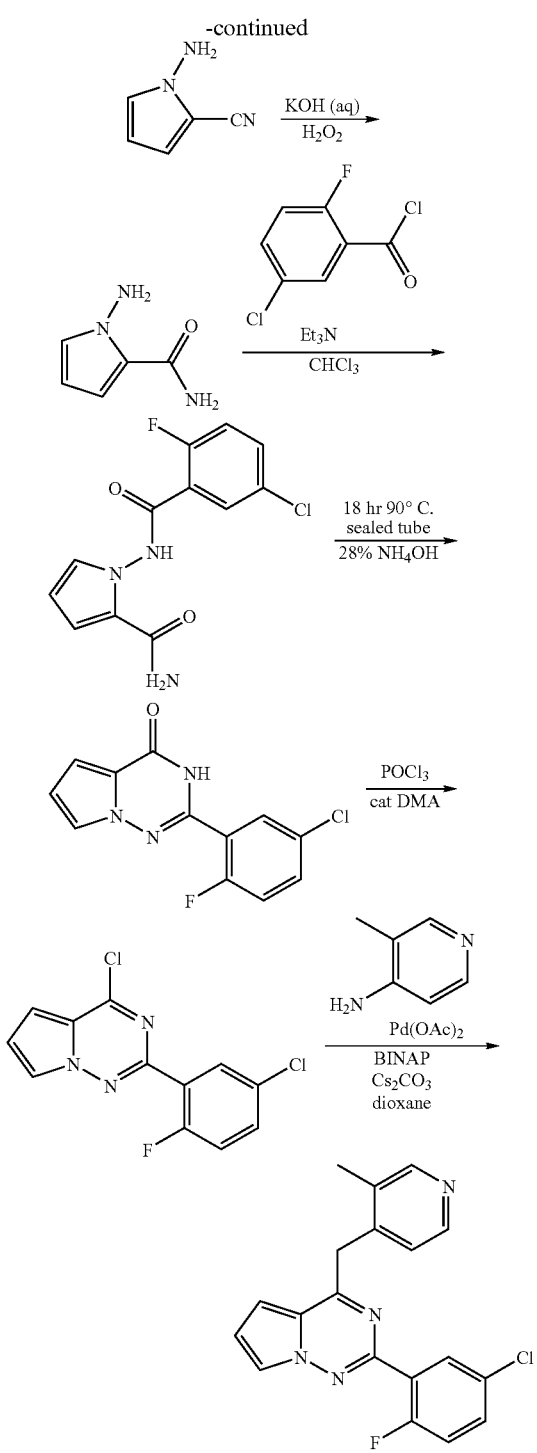

1H-Pyrrole-2-carbonitrile

Pyrrole-2-carboxaldehyde (3.00 g, 0.0316 mole) was combined with hydroxylamine-O-sulfonic acid (12.5 g, 0.11 mole) in 100 ml water and stirred at room temperature overnight. Cooled reaction mixture to 0° C. and added solution of potassium hydroxide (12.06 g, 0.603 mole) in 80 ml water dropwise over 1 hour time period. Stirred at room temperature for 3 hours. Extracted reaction mixture with dichloromethane (3×100 ml), dried extract over sodium sulfate (anh.). Removed solvent to give 3.36 g product as a liquid (yield: 100%).

1-Amino-1H-pyrrole-2-carbonitrile

1H-Pyrrole-2-carbonitrile (3.36 g, 36.5 mmole) was dissolved in 100 ml dimethylformamide to which was added potassium carbonate (7.51 g, 54.75 mmole) followed by O-(4-Nitro-2-trifluoromethyl-phenyl)-hydroxylamine (12.15 g, 54.73 mmole). The mixture was stirred at room temperature overnight. Added 80 ml water and filtered precipitate. Filtrate pH was adjusted to 10, extracted with ethyl acetate (3×100 ml). Washed extract with water, sat'd sodium chloride and dried over sodium sulfate. Removed solvent under vaccum to give 6.31 g product containing residual dimethyl formamide. Yield estimated by NMR at 64%.

1-Amino-1H-pyrrole-2-carboxylic acid amide

1-Amino-1H-pyrrole-2-carbonitrile (2.52 g, 23.5 mmole) was suspended in 75 ml water, treated with potassium hydroxide (32 g, 0.57 mole), 30% hydrogen peroxide (2 ml) and stirred overnight at room temperature. Cooled reaction mixture to 0° C. for 30 min and isolated product by filtration, washed with cold water and dried under vacuum to give 2.55 g product (yield: 87%)

1-(5-Chloro-2-fluoro-benzoylamino)-1H-pyrrolo-2-carboxylic acid amide

1-Amino-1H-pyrrole-2-carboxylic acid amide (1.25 g, 10 mmole) was partially dissolved in 45 ml acetonitrile, added triethylamine (1.39 ml, 10 mmole) followed by dropwise addition of 5-chloro-2-fluorobenzoyl chloride (1.93 g, 10 mmole) in 3 ml chloroform. Stirred reaction mixture at room temperature overnight, removed solvent under vacuum and residue taken up in chloroform, washed with 10% sodium bicarbonate, water, dried over sodium sulfate (anh.). Upon standing solid crystallized from solution. Additional product was obtained by chromatographing filtrate on silica gel eluting with 3% methanol/chloroform. Obtained 600 mg product (yield: 21%).

2-(5-Chloro-2-fluoro-phenyl)-3H-pyrrolo[2,1-f][1,2,4]triazin-4-one 1-(5-Chloro-2-fluoro-benzoylamino)-1H-pyrrole-2-carboxylic acid amide (200 mg, 0.71 mmole) was dissolved in 5 ml 28% ammonium hydroxide in a sealed tube and heated to 80° C. overnight. Purged solution with nitrogen to remove excess ammonia and acidified with 1M hydrochloric acid to pH 2. Product was isolated by filtration, washed with water and vacuum dried to give 90 mg product (yield: 48%)

4-Chloro-2-(5-chloro-2-fluoro-phenyl)-pyrrolo[2,1-f][1,2,4]triazine 2-(5-Chloro-2-fluoro-phenyl)-3H-pyrrolo[2,1-f][1,2,4]triazin-4-one (60 mg, 0.228 mmole) was added to phosphorous oxychloride (1 ml). Added 57 microliters N,N-dimethylaniline (catalyst) and heated to 110° C. overnight. Removed excess phosphorous oxychloride under vacuum, residue treated with ice, and product extracted with chloroform. Dried chloroform extract over sodium sulfate (anh.) and removed solvent to give crude product. Product was purified by silica gel chromatography eluted with chloroform to give 36 mg product (yield: 56%).

[2-(5-Chloro-2-fluoro-phenyl)-pyrrolo[2,1-f][1,2,4triazin-4-yl]-(3-methyl-pyridin-4-yl)-amine 4-Chloro-2-(5-chloro-2-fluoro-phenyl)-pyrrolo[2,1-f][1,2,4]triazine (30 mg, 0.1 06 mmole), cesium carbonate (48.5 mg, 0.149 mmole), palladium(II)acetate (1.19 mg, 0.0053 mmole), BINAP (4.96 mg, 0.0080 mmole), 4-amino-picoline (13.8 mg, 0.128 mmole) were combined in 4 ml dioxane (anh.) and heated to 90° C. with stirring overnight. Filtered reaction mixture to remove solid material, filtrate evaporated to dryness, residue dissolved in chloroform (8 ml), washed with 0.5M sodium hydroxide (1 ml), dried over sodium sulfate (anh.), evaporated to dryness, residue redissolved in dimethylformamide and purified by reversed phase HPLC. Product isolated.

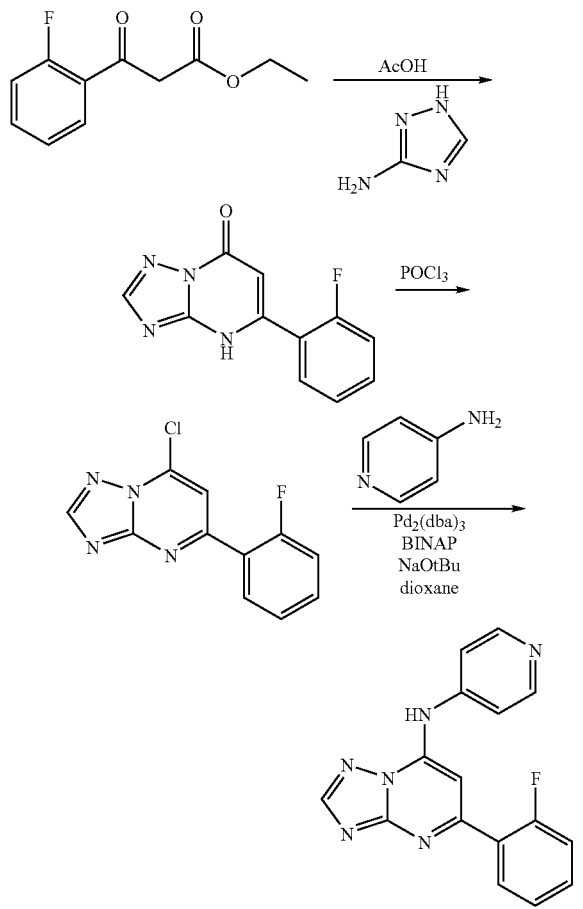

5-(2-Fluoro-phenyl)-4H-[1,2,4]triazolo[1,5-a]pyrimidin-7-one 3-amino-1,2,4-triazole (3.64 g, 43.25 mmole) and ethyl 2-fluorobenzoyl acetate (10 g, 47.57 mmole) were combined in acetic acid (45 ml) and heated to reflux overnight. Cooled reaction mixture and filtered product, washed with diethyl ether to give 3.47 g (yield: 35%).

7-Chloro-5-(2-fluoro-phenyl)-[1,2,4]triazolo[1,5-a] pyrimidine 5-(2-Fluoro-phenyl)-4H-[1,2,4]triazolo[1,5-a]pyrimidin-7-one (840 mg, 3.64 mmole) was suspended in phosphorous oxychloride (5 ml) and heated to reflux for 45 min. Removed excess phosphorous oxychloride under vacuum, the residue treated with ice, extracted product with chloroform, washed chloroform with 10% sodium bicarbonate, dried over sodium sulfate and removed solvent under vacuum to give 420 mg product (yield 46%).

[5-(2-Fluoro-phenyl)-[1,2,4]triazolo[1 5-a]pyrimidin-7-yl]-pyridin-4-yl-amine

7-Chloro-5-(2-fluoro-phenyl)-[1,2,4]triazolo[1,5-a]pyrimidine (124 mg, 0.5 mmole) was suspended in dioxane (5 ml), added 4-aminopyridine (56.4 mg, 0.6 mmole), sodium t-butoxide (67 mg, 0.7 mmole), BINAP (2.3 mg, 0.00375 mmole), Pd$_2$(dba)$_3$ (1.14 mg, 0.00125 mole) and heated to 90° C. overnight. Removed dioxane under vacuum, residue taken up in methanol, filtered and purified by reversed phase HPLC, lyophollized fractions to obtain product as trifluoroacetate salt.

Compound 81 was prepared using a procedure similar to the one described above, using ethyl 5-chloro-2-fluorobenzoyl acetate. Compound 83 was prepared using a procedure similar to the one described above, using 4-aminopyrimidine.

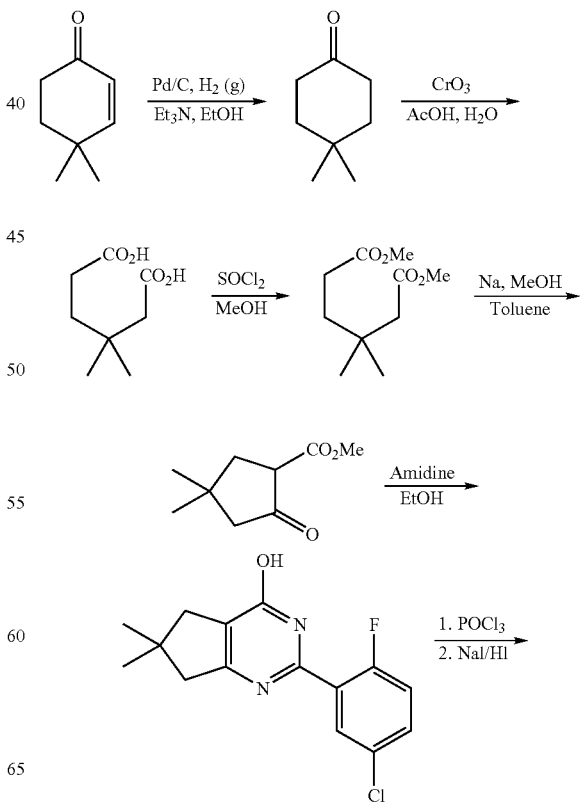

-continued

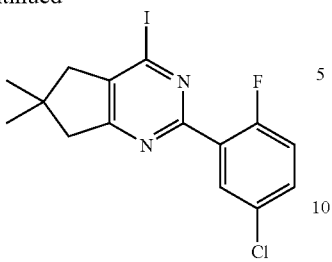

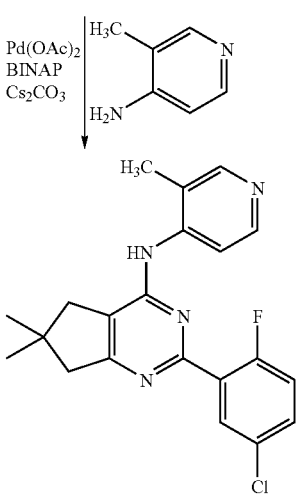

Preparation of 4,4-Dimethylcyclohexanone

Ref: *Tetrahedron Lett.*, 1992, 33(35), 5009.

A solution of 4,4-dimethylcyclohexen-2-one (10 g, 78.11 mmol) and triethylamine (10.89 mL, 78.11 mmol) in 100% ethanol (30 mL) was subjected to hydrogenation at 30 psi in a Parr apparatus, at r.t. overnight. Filtration of the contents through celite and evaporation of the filtrate gave clean product as a colorless oil (10.08 g, 99% yield).

Preparation of 3,3-Dimethylhexanedioic acid

Ref: *J. Med. Chem.* 1970, 13(3), 531.

To a solution of 4,4-dimethylcyclohexanone (2 g, 15.85 mmol) in glacial AcOH (100 mL) was added a solution of $CrO_3$ (4.75 g, 47.54 mmol) in glacial AcOH (20 mL) and water (20 mL). The mixture was stirred at 60° C. overnight then cooled and diluted with 40% aq. NaOH to pH14. The mixture was washed with diethyl ether (4×100 mL), and the aqueous layer re-acidified with conc. HCl (aq.) to pH1. The solution was extracted with diethyl ether (4×100 mL); the organic extracts dried (brine and $MgSO_4$) and evaporated to give crude diacid that was esterified directly.

Preparation of 3,3-Dimethylhexanedioic acid dimethyl ester

The crude 3,3-Dimethylhexanedioic acid was dissolved in methanol (50 mL) and thionyl chloride (1 mL) added and the solution heated at 60° C. for 6 h then cooled and evaporated to give the crude diester, which was purified by chromatography (1:1 hexane/ethyl acetate) to give the pure product as a colorless oil (2.90 g, 91% yield over 2 steps).

Preparation of 4,4-Dimethyl-2-oxo-cyclopentanecarboxylic acid methyl ester

Ref: *J. Chem. Soc. Perkin Trans.* 1, 1984, 799.

To a solution of 3,3-Dimethylhexanedioic acid dimethyl ester (2.90 g, 14.36 mmol) and methanol (100 µL) in dry toluene (10 mL) was added Sodium metal (0.66 g, 28.72 mmol). The mixture was heated to reflux overnight then cooled and evaporated. The residue was purified by chromatography (1:1 hexane/ethyl acetate) to give the desired cyclized product as a colorless oil (2.08 g, 85% yield).

Preparation of 2-(5-Chloro-2-fluoro-phenyl)-6,6-dimethyl-6,7-dihydro-5H-cyclopentapyrimidin-4-ol A solution of 4,4-Dimethyl-2-oxo-cyclopentanecarboxylic acid methyl ester (2.08 g, 12.21 mmol) and 5-Chloro-2-fluoro-benzamidine (2.32 g, 13.44 mmol) in 100% ethanol (40 mL) was heated to reflux overnight, then cooled and evaporated. The residue was dissolved in 1N (aq.) NaOH (50 mL) and washed with methylene chloride (2×50 mL). The aqueous layer was then acidified with glacial acetic acid to pH4 and extracted with methylene chloride (2×100 mL). The organic extracts were dried (brine and $MgSO_4$) and evaporated to give crude product, purified by chromatography ($CH_2Cl_2$, 0-10% MeOH) to give the desired product as a cream solid (2.10 g, 59% yield).

Preparation of 2-(5-Chloro-2-fluoro-phenyl)-4-iodo-6,6-dimethyl-6,7-dihydro-5H-cyclopentapyrimidine A suspension of 2-(5-Chloro-2-fluoro-phenyl)-6,6-dimethyl-6,7-dihydro-5H-cyclopentapyrimidin-4-ol (2.10 g, 7.16 mmol) in phosphorus oxychloride (40 mL) was heated to reflux for 2 h, then cooled and evaporated. The residue was dissolved in methylene chloride and the solution filtered through a short pad of silica gel. The filtrate was evaporated to give a residue that was suspended in hydriodic acid (10 mL) and heated at 90° C. with sodium iodide (5.37 g, 35.82 mmol) for 3 h. The mixture was cooled and diluted with water (50 mL). Aqueous sodium thiosulfate solution (50 mL) was added and the mixture shaken with methylene chloride (3×100 mL). The organic extracts were dried over $MgSO_4$ and evaporated to give crude product, purified by flash chromatography ($CH_2Cl_2$) to give the desired iodo product as a cream solid (1.75 g, 66% yield).

Preparation of [2-(5-Chloro-2-fluoro-phenyl)-6,6-dimethyl-6.7-dihydro-5H-cyclopentapyrimidin-4-yl]-(3-methyl-pyridin-4-yl)-amine To a solution of 2-(5-Chloro-2-fluoro-phenyl)-4-iodo-6,6-dimethyl-6,7-dihydro-5H-cyclopentapyrimidine (100 mg, 0.25 mmol), 3-Methyl-pyridin-4-ylamine (30 mg, 0.27 mmol), Pd(OAc)$_2$ (3 mg, 12.42 µmol) and Rac-BINAP (12 mg, 18.63 µmol) in dry dioxane (3 mL) was added $Cs_2CO_3$ (121 mg, 0.37 mmol). The mixture was heated for 48 h at 85° C., cooled and evaporated. HPLC purification gave, after lyophilization, the desired product 60 as the TFA salt, a white solid (6.4 mg).

The same procedure was used to prepare compound 61.

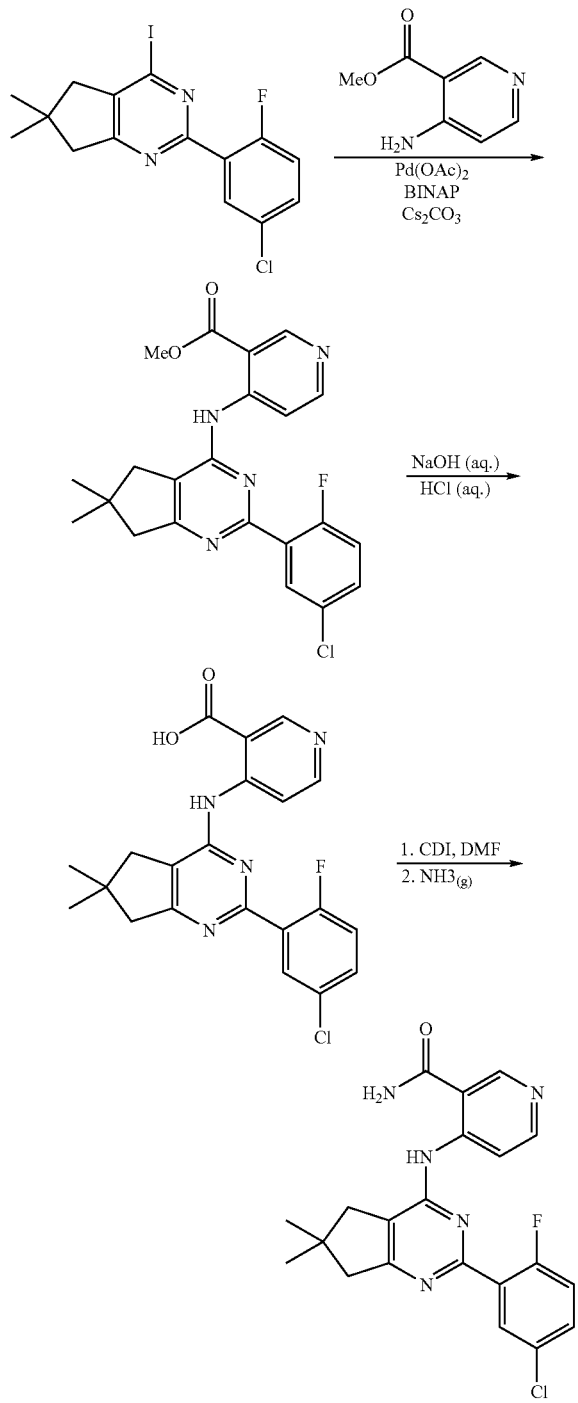

Preparation of 4-[2-(5-Chloro-2-fluoro-phenyl)-6,6-dimethyl-6,7-dihydro-5H-cyclopentapyrimidin-4-ylamino]-nicotinic acid methyl ester To a solution of 2-(5-Chloro-2-fluoro-phenyl)-4-iodo-6,6-dimethyl-6,7-dihydro-5H-cyclopentapyrimidine (500 mg, 1.24 mmol), 4-Amino-nicotinic acid methyl ester (208 mg, 1.37 mmol), Pd(OAc)$_2$ (14 mg, 62.09 µmol) and Rac-BINAP (60 mg, 93.14 µmol) in dry dioxane (10 mL) was added Cs$_2$CO$_3$ (607 mg, 1.86 mmol). The mixture was heated for 12 h at 85° C., cooled and evaporated. The residue was purified by chromatography (CH$_2$Cl$_2$, 0-10% MeOH) to give the desired product (178 mg, 34% yield).

Preparation of 4-[2-(5-Chloro-2-fluoro-phenyl)-6,6-dimethyl-6,7-dihydro-5H-cyclopentapyrimidin-4-ylamino]-nicotinic acid To a solution of 4-[2-(5-Chloro-2-fluoro-phenyl)-6,6-dimethyl-6,7-dihydro-5H-cyclopentapyrimidin-4-ylamino]-nicotinic acid methyl ester (178 mg, 0.42 mmol) in dioxane (10 mL) was added NaOH (aq.) (451 µL, 0.44 mmol, 0.97N solution). The mixture was heated at 60° C. for 1 h then cooled, and HCl (aq.) (425 µL, 0.44 mmol, 1.03N solution) was added. On addition, the acid precipitated from solution and was filtered and dried in vacuo, to give 137 mg of product.

Preparation of 4-[2-(5-Chloro-2-fluoro-phenyl)-6,6-dimethyl-6,7-dihydro-5H-cyclopentapyrimidin-4-ylamino]-nicotinamide A suspension of 4-[2-(5-Chloro-2-fluoro-phenyl)-6,6-dimethyl-6,7-dihydro-5H-cyclopentapyrimidin-4-ylamino]-nicotinic acid (25 mg, 60.56 µmol) and Carbonyldiimidazole (20 mg, 121.11 µmol) in dry DMF (3 mL) was heated at 70° C. for 1 h then cooled to r.t. A stream of NH$_3$ gas was passed through the solution for 30 min., giving clean conversion to the amide product. Evaporation of the solution, followed by HPLC purification gave, after lyophilization, the pure amide 62 as the TFA salt (20 mg).

Compounds 63 to 66 were prepared using the same procedure.

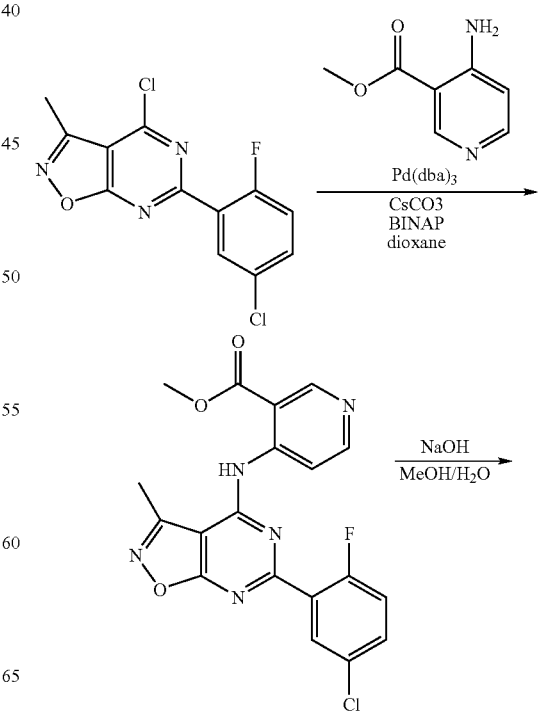

-continued

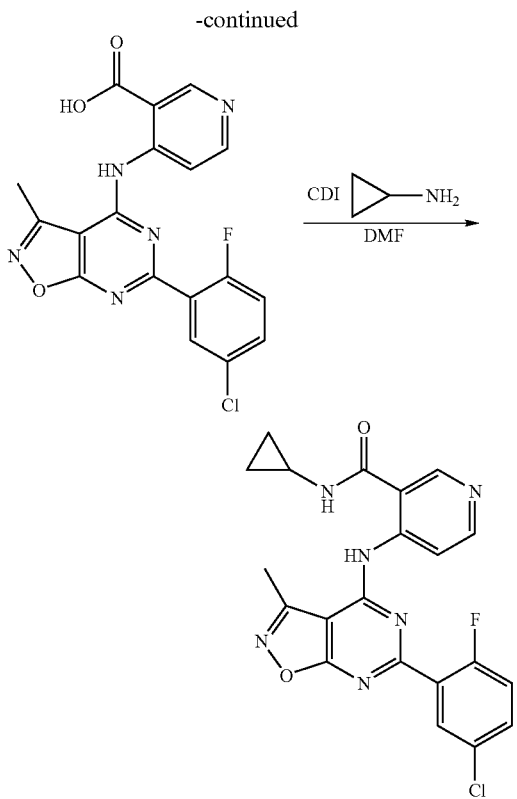

4-[6-(5-Chloro-2-fluoro-phenyl)-3-methyl-isoxazolo[5,4-d]pyrimidin-4-ylamino]-nicotinic acid methyl ester 4-Chloro-6-(5-chloro-2-fluoro-phenyl)-3-methyl-isoxazolo[5,4-d]pyrimidine (Prepared by method used for 0043) (298 mg, 1 mmole) was dissolved in dioxane (4 ml), added BINAP (4.67 mg, 0.0075), 4-Amino-nicotinic acid methyl ester (182 mg, 1.2 mmole), cesium carbonate (456 mg, 1.4 mmole), and Pd$_2$(dba)$_3$ (2.29 mg, 0.0025 mmole) to the mixture and heated to 90° C. overnight. Removed dioxane under vacuum and triturated residue with ethyl acetate (5 ml) and isolated product by filtration. Obtained 525 mg solid which also contained cesium carbonate as byproduct.

4-[6-(5-Chloro-2-fluoro-phenyl)-3-methyl-isoxazolo[5,4-d]pyrimidin-4-ylamino]-nicotinic acid 4-[6-(5-Chloro-2-fluoro-phenyl)-3-methyl-isoxazolo[5,4-d]pyrimidin-4-ylamino]-nicotinic acid methyl ester (525 mg) was suspended in methanol (4 ml) added 1M sodium hydroxide solution (4 ml) and heated to 70° C. for 30 min. Removed methanol under vacuum and acidified solution to pH 4 with 6M hydrochloric acid. Filtered solid, washed with water and oven dried to give 137 mg product.

4-[6-(5-Chloro-2-fluoro-phenyl)-3-methyl-isoxazolo[5,4-d]pyrimidin-4-ylamino]-N-cyclopropyl-nicotinamide 4-[6-(-Chloro-2-fluoro-phenyl)-3-methyl-isoxazolo[5,4-d]pyrimidin-4-ylamino]-nicotinic acid (130 mg, 0.325 mmole) was combined with carbonyl diimidazole (105 mg, 0.650 mmole) in 2 ml dimethylformamide and heated to 70° C. for 1 hour. Cooled mixture to room temperature and added cyclcopropylamine (74 mg, 1.3 mmole) and stirred for 1 hour at room temperature. Filtered solution and subjected filtrate to HPLC purification on reversed phase HPLC. Upon lyophillization of fractions containing pure product obtained 13.7 mg.

Compound 77 was prepared using a procedure described above, using methylamine.

Scheme R (Synthesis of Compound 33)

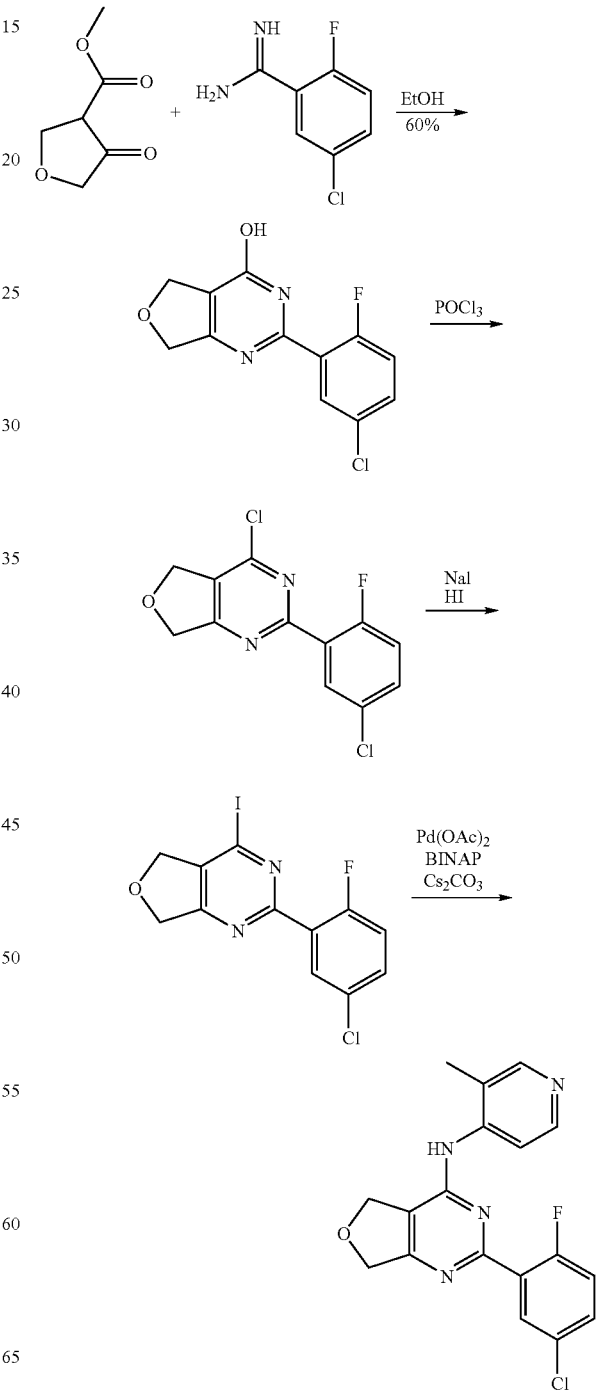

2-(5-Chloro-2-fluorophenyl)-5,7-dihydrofuro[3,4-d]pyrimidin-4-ol

To a suspension of 4-oxo-tetrahydrofuran-3-carboxylic acid methyl ester (prepared according to Dowd, P.; Choi, S-C. *Tetrahedron*, 1991, 47, 4847-4860; 800 mg, 5.55 mmol, 1 eq) in ethanol (20 ml) was added a solution of 2-fluoro-5-chlorobenzamidine (961 mg, 5.55 mmol, 1 eq) in EtOH (10 ml). The reaction mixture was heated to 80° C. overnight. The reaction mixture was cooled to rt and the white precipitate was filtered and washed with cold ethyl actetate (2×20 ml). The crude residue was partitioned between chloroform and water. The aqueous layer was acidified to pH 4 and the product was extracted with chloroform (3×50 ml). The organic layers were combined, washed with brine, dried over $MgSO_4$, filtered and concentrated in vacuo to give a crude solid which was purified by flash column chromatography (5% MeOH in EtOAc) to give a white solid 2-(5-Chloro-2-fluorophenyl)-5,7-dihydrofuro[3,4-d]pyrimidin-4-ol (440 mg, 30%).

4-Chloro-2-(5-chloro-2-fluorophenyl)-5,7-dihydrofuro[3,4-d]pyrimidine

A suspension of 2-(5-chloro-2-fluorophenyl)-5,7-dihydrofuro[3,4-d]pyrimidin-4-ol (100 mg, 0.36 mmol, 1 eq) in $POCl_3$ (5 ml) was stirred under reflux for 1 h. The solution was then cooled to room temperature and concentrated under reduced pressure to give a white solid which was dissolved in dry methylene chloride. The solution was cooled to 0° C. and ice was added followed by sat. $NaHCO_3$. The organic layer was separated, washed with brine, dried ($MgSO_4$), filtered and evaporated in vacuo to provide a crude white solid which was purified by flash column chromatography (1:9 EtOAc:Hexane) to give 4-Chloro-2-(5-chloro-2-fluorophenyl)-5,7-dihydrofuro[3,4-d]pyrimidine (78 mg, 73%) as a white solid.

2-(5-Chloro-2-fluorophenyl)-4-iodo-5,7-dihydrofuro[3,4-d]pyrimidine

To a suspension of 4-chloro-2-(5-chloro-2-fluorophenyl)-5,7-dihydrofuro[3,4-d]pyrimidine (78 mg, 0.275 mmol, 1 eq) in 57% $H_{(aq)}$ (2 ml) at rt was added NaI (206 mg, 1.37 mmol, 5 eq). The reaction mixture stirred at rt overnight and then was poured onto ice. The product was extracted with chloroform and the aqueous layer was neutralized with $NaHCO_3$ and extracted further with chloroform. The organic layers were combined washed with brine, dried ($MgSO_4$), filtered and evaporated in vacuo to provide a crude residue of 2-(5-Chloro-2-fluorophenyl)-4-iodo-5,7-dihydrofuro[3,4-d]pyrimidine which was not further purified.

[2-(5-Chloro-2-fluorophenyl)-5,7-dihydrofuro[3,4-d]pyrimidin-4-yl]-(3-methyl-pyridin-4-yl)-amine, 33

To a solution of 2-(5-chloro-2-fluorophenyl)-4-iodo-5,7-dihydrofuro[3,4-d]pyrimidine (80 mg, 0.21 mmol, 1 eq) in anhydrous dioxane (5 ml) was added $Pd(OAc)_2$ (2 mg, 0.01 mmol, 0.05 eq) followed by BINAP (10 mg, 0.02 mmol, 0.075 eq), 4-amino-3-picoline (25 mg, 0.23 mmol, 1.2 eq) and $Cs_2CO_3$ (100 mg, 0.32 mmol, 1.5 eq). The reaction mixture was heated to 80° C. for 15 h. The reaction mixture was cooled to rt and filtered through Celite® and the crude material was purified by flash column chromatography (9:1/ ethyl acetate:hexane) to afford [2-(5-Chloro-2-fluorophenyl)-5,7-dihydrofuro[3,4-d]pyrimidin-4-yl]-(3-methyl-pyridin-4-yl)-amine, 33 (20 mg, 26%) as a white solid.

Scheme S (Synthesis of compound 34)

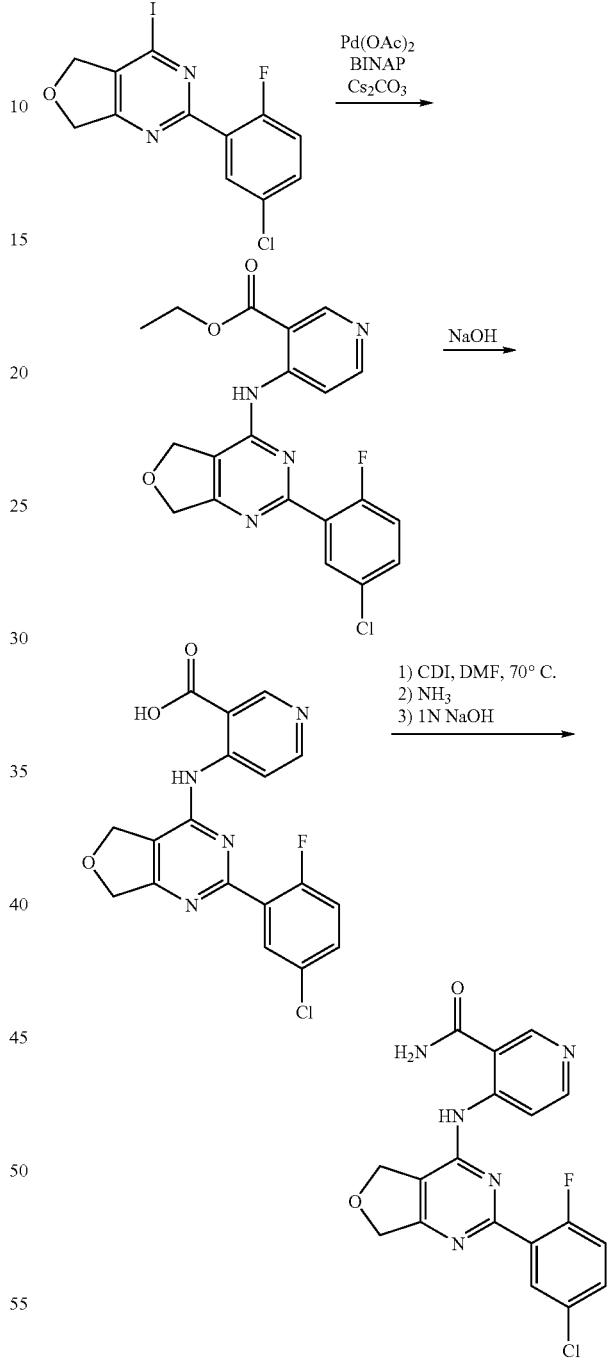

4-[2-(5-Chloro-2-fluoro-phenyl)-5,7-dihydro-furo[3,4-d]pyrimidin-4-ylamino]-nicotinic acid ethyl ester Following the general reaction procedure used for the synthesis of [2-(5-Chloro-2-fluorophenyl)-5,7-dihydrofuro[3,4-d]pyrimidin-4-yl]-(3-methyl-pyridin-4-yl)-amine 33, 4-[2-(5-chloro-2-fluoro-phenyl)-5,7-dihydro-furo[3,4-d]pyrimidin-4-ylamino]-nicotinic acid ethyl ester was isolated in 73% yield.

4-[2-(5-Chloro-2-fluoro-phenyl)-5,7-dihydro-furo[3,4-d]pyrimidin-4-ylamino]-nicotinic acid To a suspension of 4-[2-(5-chloro-2-fluoro-phenyl)-5,7-dihydro-furo[3,4-d]pyrimidin-4-ylamino]-nicotinic acid ethyl ester (60 mg, 0.14 mmol, 1 eq) in MeOH (5 ml) was added a 1N NaOH$_{(aq)}$ solution (300 µl, 0.30 mmol, 2 eq) and the reaction mixture was heated to reflux for 2 h. The solution was cooled to rt and concentrated in vacuo. Water (20 ml) was added to the crude material and the aqueous layer was acidified to pH 4. The solid was filtered, washed with water (2×5 ml) and dried overnight to afford 4-[2-(5-Chloro-2-fluoro-phenyl)-5,7-dihydro-furo[3,4-d]pyrimidin-4-ylamino]-nicotinic acid (50 mg, 90%).

4-[2-(5-Chloro-2-fluoro-phenyl)-5,7-dihydro-furo[3,4-d]pyrimidin-4-ylamino]-nicotinic amide, 34

To a suspension of 4-[2-(5-chloro-2-fluoro-phenyl)-5,7-dihydro-furo[3,4-d]pyrimidin-4-ylamino]-nicotinic acid (50 mg, 0.13 mmol, 1 eq) in DMF (2 ml) was added 1-1'-carbonyldiimidazole (50 mg, 0.31 mmol, 2.4 eq) and the reaction mixture was warmed to 70° C. for 2 h. The mixture was cooled to r.t. and NH$_{3(g)}$ was bubbled through for 10 min. The reaction mixture was stirred at rt for an additional 1 h. The reaction was concentrated in vacuo and the residue was triturated with water (2×5 ml). To the crude residue was added 1N NaOH (5 ml) and the suspension was heated to 100° C. for 2 h. The reaction mixture was cooled to room temperature and neutralized with 1N HCl and the solid was filtered to give 4-[2-(5-Chloro-2-fluoro-phenyl)-5,7-dihydro-furo[3,4-d]pyrimidin-4-ylamino]-nicotinic amide, 34 (25 mg, 50%) as a white solid.

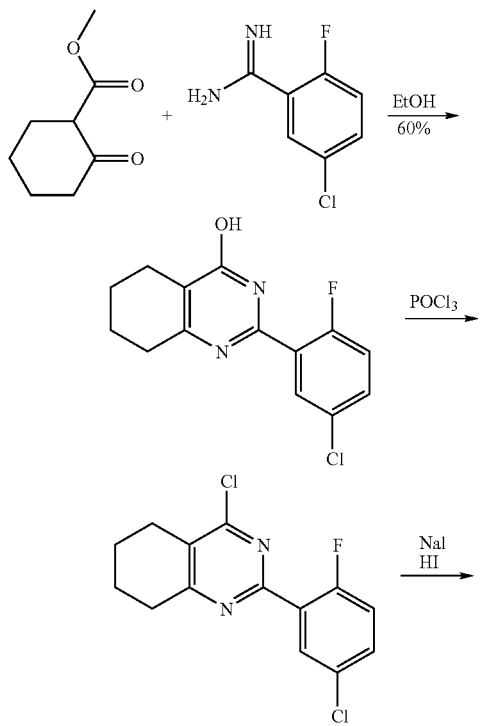

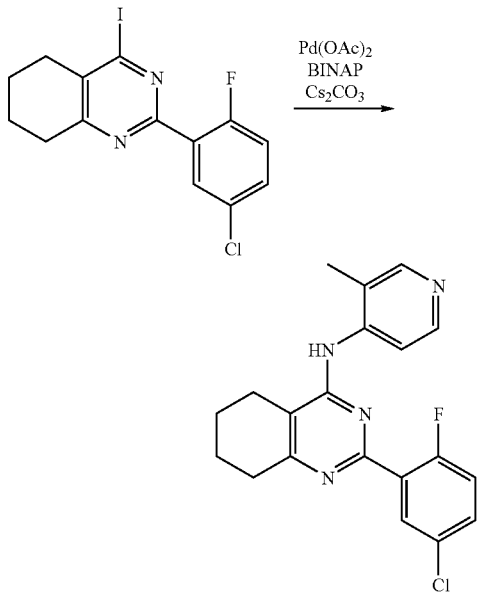

2-(5-Chloro-2-fluorophenyl)-5,6,7,8-tetrahydroquinazolin-4-ol

To a solution of methyl-2-oxocyclopentane carboxylate (2 g, 11.8 mmol, 1 eq), in dry ethanol (20 ml) was added a solution of 2-fluoro-5-chlorobenzamidine (2.04 g, 11.8 mmol, 1 eq) in ethanol (20 ml) and the reaction mixture was heated to 80° C. overnight. The reaction mixture was cooled to rt and the solvent was removed in vacuo to afford a crude residue which was purified by recrystallization from hot ethyl acetate to afford 2-(5-chloro-2-fluorophenyl)-5,6,7,8-tetrahydroquinazolin-4-ol (2.56 g, 78%) as a white solid.

4-Chloro-2-(5-chloro-2-fluorophenyl)-5,6,7,8-tetrahydroquinazoline

A suspension of 2-(5-chloro-2-fluorophenyl)-5,6,7,8-tetrahydroquinazolin-4-ol (500 mg, 1.89 mmol) in POCl$_3$ (6 ml) was stirred under reflux for 1 h. The solution was then cooled to room temperature and concentrated under reduced pressure to afford a white solid which was dissolved in methylene chloride. The solution was cooled to 0° C. and ice was added followed by sat. NaHCO$_3$. The organic layer was separated, washed with brine, dried (MgSO$_4$), filtered and evaporated in vacuo to provide a crude white solid 4-Chloro-2-(5-chloro-2-fluorophenyl)-5,6,7,8-tetrahydroquinazoline which was not further purified.

2-(5-Chloro-2-fluorophenyl)-4-iodo-5,6,7,8-tetrahydroquinazoline

To a suspension of 4-chloro-2-(5-chloro-2-fluorophenyl)-5,6,7,8-tetrahydroquinazoline (534 mg, 1.89 mmol, 1 eq) in a 57% HI solution in water (10 ml) at r.t. was added NaI (1.42 g, 9.47 mmol, 5 eq). The reaction mixture was stirred at r.t. overnight and then poured onto ice. The product was extracted with chloroform and the aqueous layer was neutralized with NaHCO$_3$ and extracted further with more chloroform. The organic layers were combined washed with brine, dried (MgSO$_4$), filtered and evaporated in vacuo to provide a crude white solid 2-(5-Chloro-2-fluorophenyl)-4-iodo-5,6,7,8-tetrahydroquinazoline which was not further purified.

[2-(5-Chloro-2-fluorophenyl)-5,6,7,8-tetrahydro-quinazolin-4-yl]-(3-methylpyridin-4-yl)-amine, 38

The crude 2-(5-chloro-2-fluorophenyl)-4-iodo-5,6,7,8-tetrahydroquinazoline (130 mg, 0.35 mmol, 1 eq) was dissolved in dioxane (5 ml) and to this was added Pd(OAc)$_2$ (4 mg, 0.02 mmol, 0.05 eq) followed by BINAP (16 mg, 0.03 mmol, 0.075 eq), 4-amino-3-picoline (49 mg, 0.45 mmol, 1.3 eq) and Cs$_2$CO$_3$ (170 mg, 0.52 mmol, 1.5 eq). The reaction mixture was heated to 80° C. for 15 h. The reaction mixture was cooled to r.t. and filtered through Celite® and the crude material was purified by flash column chromatography (1:1/ethyl acetate:hexane) to afford [2-(5-chloro-2-fluorophenyl)-5,6,7,8-tetrahydroquinazolin-4-yl]-(3-methylpyridin-4-yl)-amine, 38 (110 mg, 86%).

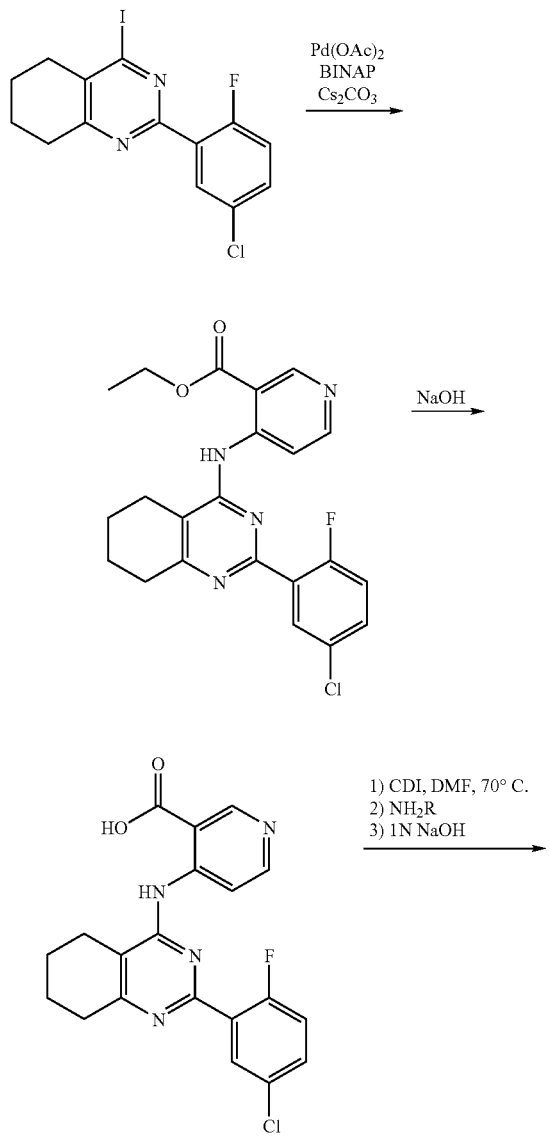

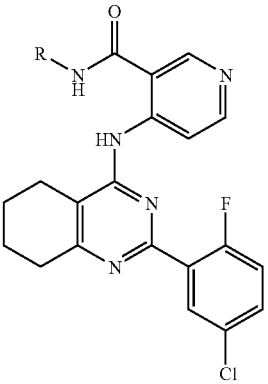

4-[2-(5-Chloro-2-fluorophenyl)-5,6,7,8-tetrahydro-quinazolin-4-ylamino]-nicotinic acid ethyl ester Following the general reaction procedure for the synthesis of [2-(5-chloro-2-fluorophenyl)-5,6,7,8-tetrahydroquinazolin-4-yl]-(3-methylpyridin-4-yl)-amine, 38, 4-[2-(5-Chloro-2-fluorophenyl)-5,6,7,8-tetrahydroquinazolin-4-ylamino]-nicotinic acid ethyl ester was isolated in 67% yield.

4-[2-(5-Chloro-2-fluorophenyl)-5,6,7,8-tetrahydro-quinazolin-4-ylamino]-nicotinic acid, 50

To a suspension of 4-[2-(5-chloro-2-fluorophenyl)-5,6,7,8-tetrahydroquinazolin-4-ylamino]-nicotinic acid ethyl ester (150 mg, 0.35 mmol, 1 eq) in MeOH (5 ml) was added a 1N NaOH$_{(aq)}$ solution (423 µl, 0.42 mmol, 1.2 eq) and the reaction mixture was refluxed for 1 h. The solution was cooled to rt and concentrated in vacuo. Water (20 ml) was added to the crude material and the aqueous layer was acidified to pH 4. The solid was filtered, washed with water (2×5 ml) and dried overnight to give 4-[2-(5-chloro-2-fluorophenyl)-5,6,7,8-tetrahydroquinazolin-4-ylamino]-nicotinic acid, 50 (132 mg, 94%) as a cream colored solid.

4-[2-(5-Chloro-2-fluorophenyl)-5,6,7,8-tetrahydro-quinazolin-4-ylamino]-N-cyclopropyl nicotinamide, 45

To a suspension of 4-[2-(5-chloro-2-fluorophenyl)-5,6,7,8-tetrahydroquinazolin-4-ylamino]-nicotinic acid (40 mg, 0.10 mmol, 1 eq) in dry DMF (1 ml) was added triethylamine (15 µl, 0.11 mmol, 1.1 eq) followed by cyclopropylamine (70µl, 0.10 mmol, 10 eq). To the suspension was added a solution of PyBrOP (56 mg, 0.21 mmol, 1.2 eq) in DMF (500 µl) dropwise. The reaction mixture was stirred at room temperature for 16 h. The reaction was concentrated in vacuo and the residue was triturated with ether (2×20 ml). The crude residue was purified by flash column chromatography (0-5% MeOH in CHCl$_3$) to give 4-[2-(5-Chloro-2-fluorophenyl)-5,6,7,8-tetrahydroquinazolin-4-ylamino]-N-cyclopropyl nicotinamide, 45 (15 mg, 34%) as a white solid.

Compound 40 was prepared by the method described for the synthesis of compound 45 employing methylamine in place of cyclopropylamine. Compound 57 was prepared by the method described for the synthesis of compound 45 employing 1-amino-propan-2-(S)-ol in place of cyclopropylamine. Compound 59 was prepared by the method described for the synthesis of compound 45 employing N,N-diethylethenediamine in place of cyclopropylamine

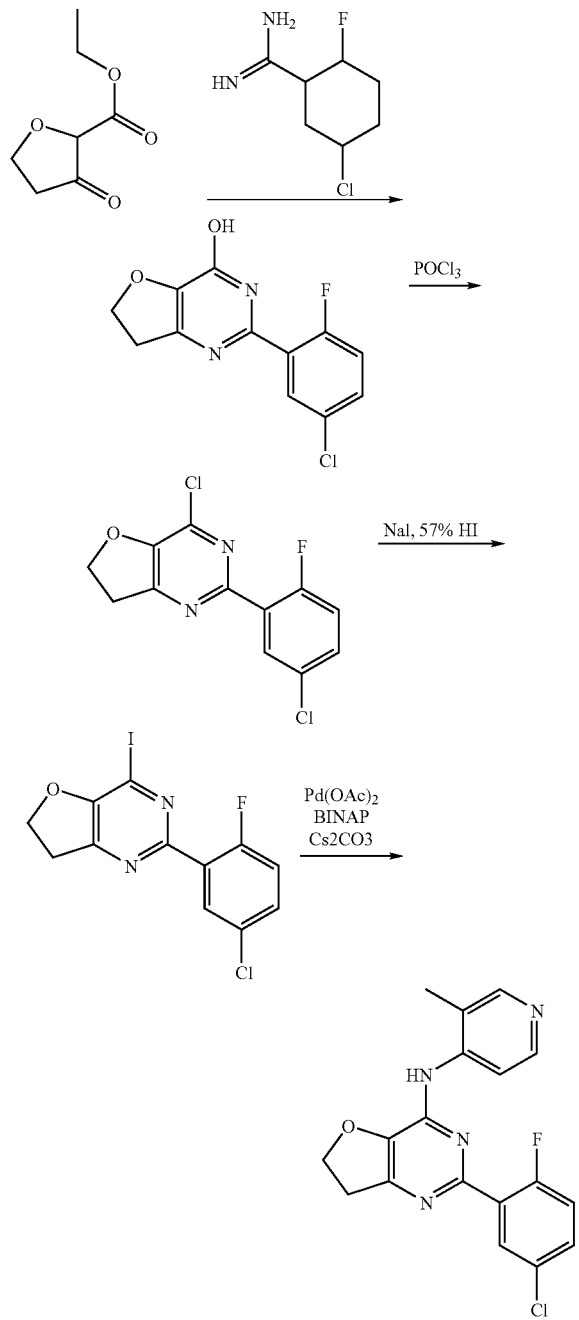

Scheme V (Synthesis of compound 39)

2-(5-Chloro-2-fluorophenyl)-6,7-dihydrofuro3,2-d]pyrimidin-4-ol

To a solution of 2-fluoro-5-chlorobenzamidine (1.05 g, 6.08 mmol, 1.2 eq) in EtOH (20 ml) was added 3-oxo-tetrahydrofuran-2-carboxylic acid ethyl ester (prepared according to Moyer, M. P; Feldman, P. L.; Rapoport, H. *J. Org. Chem*, 1985, 50, 5223-5230; 800 mg, 5.06 mmol, 1 eq) in ethanol (5 ml). The reaction mixture was heated to 80° C. overnight. The reaction mixture was cooled to rt and the crude residue was purified by flash column chromatography (5% MeOH in CHCl$_3$) to afford a white solid 2-(5-chloro-2-fluorophenyl)-6,7-dihydrofuro[3,2-d]pyrimidin-4-ol (650 mg, 53%).

4-Chloro-2-(5-chloro-2-fluorophenyl)-6,7-dihydro-furo[3,2-d]pyrimidine

A suspension of 2-(5-chloro-2-fluorophenyl)-6,7-dihydrofuro[3,2-d]pyrimidin-4-ol (100 mg, 0.36 mmol, 1 eq) in POCl$_3$ (5 ml) was stirred under reflux for 1 h. The solution cooled to rt and concentrated under reduced pressure to give a white solid which was dissolved in methylene chloride. The solution was cooled to 0° C. and ice was added followed by sat. NaHCO$_3$. The organic layer was separated, washed with brine, dried (MgSO$_4$), filtered and evaporated in vacuo to provide a crude white solid which was purified by flash column chromatography (1:9 EtOAc:Hexane) to afford 4-chloro-2-(5-chloro-2-fluorophenyl)-6,7-dihydrofuro[3,2-d]pyrimidine (78 mg, 73%) as a white solid.

2-(5-Chloro-2-fluorophenyl)-4-iodo-6,7-dihydrofuro [3,2-d]pyrimidine

To a suspension of 4-chloro-2-(5-chloro-2-fluorophenyl)-6,7-dihydrofuro[3,2-d]pyrimidine (80 mg, 0.28 mmol, 1 eq) in a 57% HI solution in water (2 ml) at rt. was added NaI (206 mg, 1.41 mmol, 5 eq). The reaction mixture was stirred at rt overnight and then poured onto ice. The product was extracted with chloroform and the aqueous layer was neutralized with NaHCO$_3$ and extracted further with more chloroform. The organic layers were combined washed with brine, dried (MgSO$_4$), filtered and evaporated in vacuo to provide a crude residue 2-(5-chloro-2-fluorophenyl)-4-iodo-6,7-dihydrofuro[3,2-d]pyrimidine that was not further purified.

[2-(5-Chloro-2-fluorophenyl)-6,7-dihydrofuro[3,2-d] pyrimidin-4-yl]-(3-methyl-pyridin-4-yl)-amine, 39

To a solution of 2-(5-chloro-2-fluorophenyl)-4-iodo-6,7-dihydrofuro[3,2-d]pyrimidine (106 mg, 0.28 mmol, 1 eq) in dioxane (5 ml) was added Pd(OAc)$_2$ (3 mg, 0.01 mmol, 0.05 eq) followed by BINAP (13 mg, 0.02 mmol, 0.075 eq), 4-amino-3-picoline (40 mg, 0.37 mmol, 1.3 eq) and Cs$_2$CO$_3$ (138 mg, 0.42 mmol, 1.5 eq). The reaction mixture was heated to 80° C. for 15 h. The reaction mixture was cooled to rt and filtered through Celite® and the crude material was purified by flash column chromatography (4:1/ethyl acetate: hexane-100% ethylacetate) to afford [2-(5-chloro-2-fluorophenyl)-6,7-dihydrofuro[3,2-d]pyrimidin-4-yl]-(3-methyl-pyridin-4-yl)-amine, 39 (30 mg, 30%) as a white solid.

Scheme W (Synthesis of compound 44)

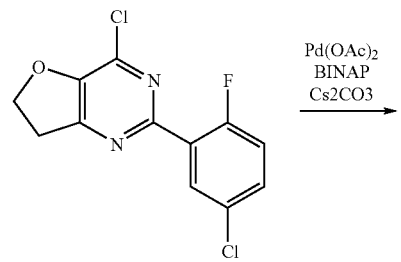

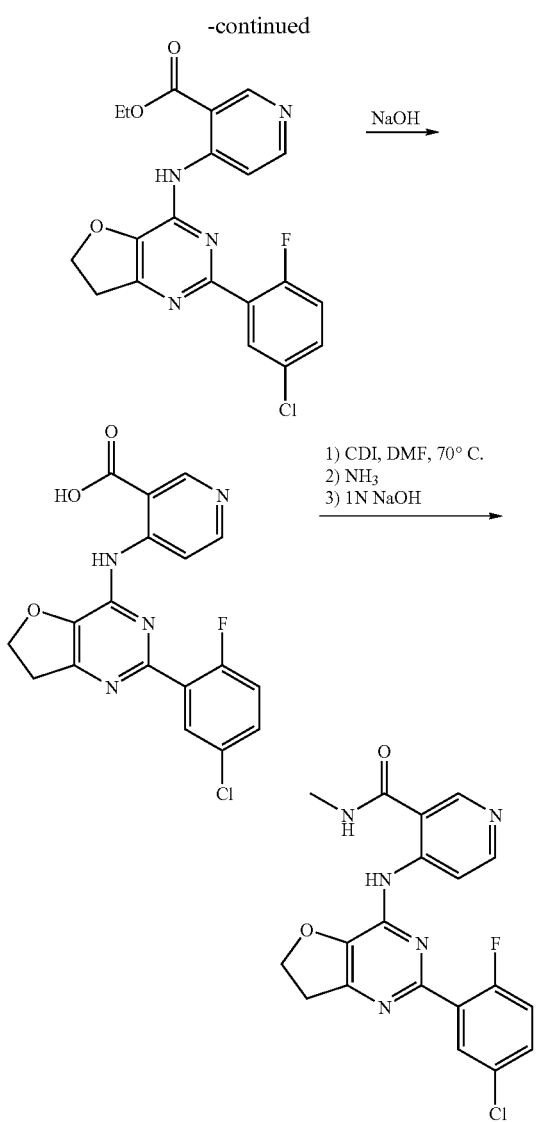

4-[2-(5-Chloro-2-fluorophenyl)-6,7-dihydrofuro[3,2-d]pyrimidin-4-ylamino]-nicotinic acid ethyl ester To a solution of 4-chloro-2-(5-chloro-2-fluorophenyl)-6,7-dihydrofuro[3,2-d]pyrimidine (320 mg, 1.13 mmol, 1 eq) in dioxane (5 ml) was added Pd(OAc)$_2$ (13 mg, 0.06 mmol, 0.05 eq) followed by BINAP (53 mg, 0.08 mmol, 0.075 eq), 4-aminonicotinic acid ethyl ester (206 mg, 1.24 mmol, 1.1 eq) and Cs$_2$CO$_3$ (478 mg, 1.46 mmol, 1.5 eq). The reaction mixture was heated to 80° C. for 15 h. The reaction mixture was cooled to rt and filtered through Celite® and the crude material was purified by flash column chromatography (0-5%MeOH in CHCl$_3$) to afford 4-[2-(5-chloro-2-fluorophenyl)-6,7-dihydrofuro[3,2-d]pyrimidin-4-ylamino]-nicotinic acid ethyl ester (100 mg, 21%) as a white solid.

4-[2-(5-Chloro-2-fluorophenyl)-6,7-dihydrofuro[3,2-d]pyrimidin-4-ylamino]-nicotinic acid To a suspension of 4-[2-(5-chloro-2-fluorophenyl)-6,7-dihydrofuro[3,2-d]pyrimidin-4-ylamino]-nicotinic acid ethyl ester (100 mg, 0.24 mmol, 1 eq) in MeOH (5 ml) was added a 1N NaOH$_{(aq)}$ solution (290 µl, 0.29 mmol, 1.2 eq) and the reaction mixture was refluxed for 5 h. The solution was cooled to rt and concentrated in vacuo. Water (20 ml) was added to the crude material and the aqueous layer was acidified to pH 4. The solid was filtered, washed with water (2×5 ml) and dried overnight to afford 4-[2-(5-chloro-2-fluorophenyl)-6,7-dihydrofuro[3,2-d]pyrimidin-4-ylamino]-nicotinic acid (88 mg, 94%) as a cream colored solid.

4-[2-(5-Chloro-2-fluorophenyl)-6,7-dihydrofuro[3,2-d]pyrimidin-4-ylamino]-N-methyl nicotinamide, 44

To a suspension of 4-[2-(5-chloro-2-fluorophenyl)-6,7-dihydrofuro[3,2-d]pyrimidin-4-ylamino]-nicotinic acid (75 mg, 0.19 mmol, 1 eq) in DMF (2 ml) was added triethylamine (30 µl, 0.21 mmol, 1.1 eq) followed by methylamine (1.17 ml, 3.89 mmol, 2M solution in THF, 20 eq). To the suspension was added a solution of PyBrOP (100 mg, 0.21 mmol, 1.2 eq) in DMF (1 ml) dropwise. The reaction mixture was stirred at room temperature for 16 h. The reaction was concentrated in vacuo and the residue was triturated with ether (2×20 ml). The crude residue was purified by flash column chromatography (5% MeOH in CHCl$_3$) to afford 4-[2-(5-chloro-2-fluorophenyl)-6,7-dihydrofuro[3,2-d]pyrimidin-4-ylamino]-N-methyl nicotinamide, 44 (20 mg, 26%) as a white solid.

Scheme X (Synthesis of compound 43)

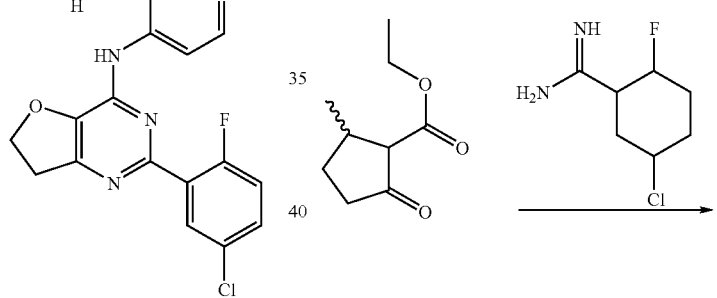

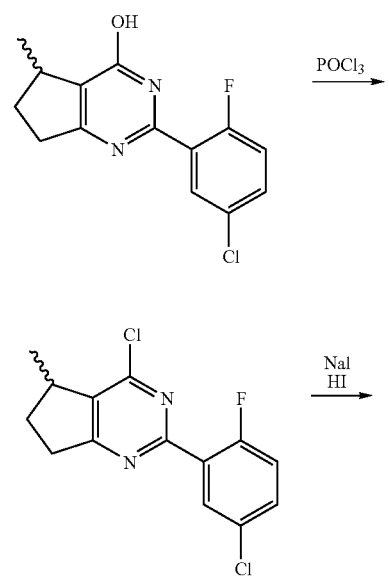

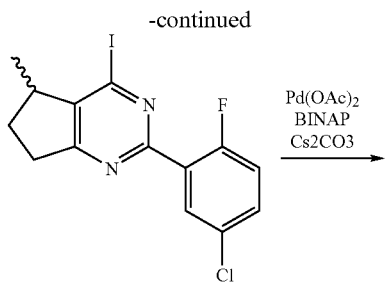

2-(5-Chloro-2-fluorophenyl)-5-methyl-6,7-dihydro-5H-cyclopentapyrimidin-4-ol

To a solution of 2-fluoro-5-chlorobenzamidine (1.95 g, 11.27 mmol, 1.1 eq) in EtOH (20 ml) was added a solution of 2-methyl-5-oxo cyclopentanecarboxylic acid ethyl ester (prepared according to Wang, C.; Gu, X.; Yu, M. S.; Curran, D. P.: *Tetrahedron*, 1998, 29, 8355-8370; 1.60 g, 10.26 mmol, 1 eq) in ethanol (5 ml). The reaction mixture was heated to 80° C. overnight. The reaction mixture was cooled to rt and the solvent was removed in vacuo to give a crude residue which was purified by recrystallization from hot ethyl acetate to give 2-(5-chloro-2-fluorophenyl)-5-methyl-6,7-dihydro-5H-cyclopentapyrimidin-4-ol (1.0 g, 35%) as a white crystalline solid and the filtrate was further purified by flash column chromatography to give another 850 mg of 2-(5-chloro-2-fluorophenyl)-5-methyl-6,7-dihydro-5H-cyclopentapyrimidin-4-ol.

2-(5-Chloro-2-fluorophenyl)-4-iodo-5-methyl-6,7-dihydro-5H-cyclopentapyrimidine A suspension of 2-(5-chloro-2-fluorophenyl)-5-methyl-6,7-dihydro-5H-cyclopentapyrimidin-4-ol (200 mg, 0.72 mmol, 1 eq) in $POCl_3$ (5 ml) was stirred under reflux for 1 h. The solution was then cooled to room temperature and concentrated under reduced pressure to give a white solid. The residual $POCl_3$ was removed by azeotrope with chloroform. To a suspension of the crude iminochloride in a 57% HI solution in water (5 ml) at rt was added NaI (540 mg, 3.60 mmol, 5 eq). The reaction mixture was stirred at rt overnight and then poured onto ice. The product was extracted with chloroform and the aqueous layer was neutralized with $NaHCO_3$ and extracted further with chloroform. The organic layers were combined washed with brine, dried ($MgSO_4$), filtered and evaporated in vacuo to provide a crude residue 2-(5-chloro-2-fluorophenyl)-4-iodo-5-methyl-6,7-dihydro-5H-cyclopentapyrimidine which was not further purified.

[2-(5-Chloro-2-fluorophenyl)-5-methyl-6,7-dihydro-5H-cyclopentapyrimidin-4-yl]-(3-methyl-pyridin-4-yl)-amine, 43

To a solution of 2-(5-chloro-2-fluorophenyl)-4-iodo-5-methyl-6,7-dihydro-5H-cyclopentapyrimidine (275 mg, 0.71 mmol, 1 eq) in dioxane (5 ml) was added $Pd(OAc)_2$ (8 mg, 0.04 mmol, 0.05 eq) followed by BINAP (33 mg, 0.05 mmol, 0.075 eq), 4-amino-3-picoline (84 mg, 0.78 mmol, 1.1 eq) and $Cs_2CO_3$ (347 mg, 1.06 mmol, 1.5 eq). The reaction mixture was heated to 80° C. for 15 h. The reaction mixture was cooled to rt and filtered through Celite® and the crude material was purified by flash column chromatography (1:1/ethyl acetate:hexane-100% ethyl acetate) to afford [2-(5-chloro-2-fluorophenyl)-5-methyl-6,7-dihydro-5H-cyclopentapyrimidin-4-yl]-(3-methyl-pyridin-4-yl)-amine, 43 (250 mg, 96%).

Scheme Y (Synthesis of compounds 48, 49, 47, 46)

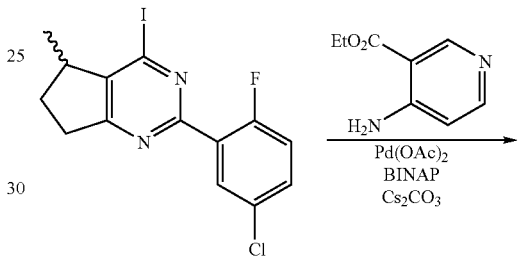

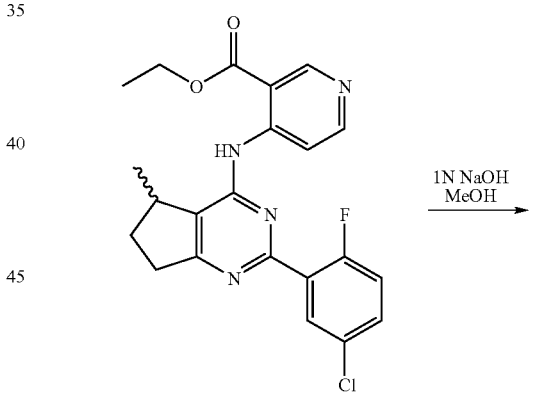

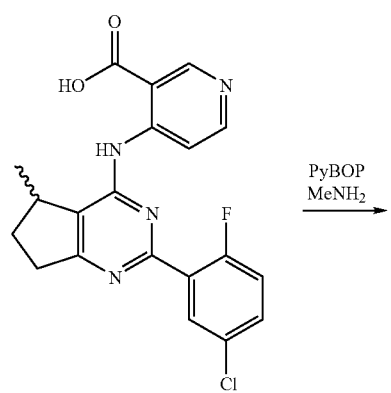

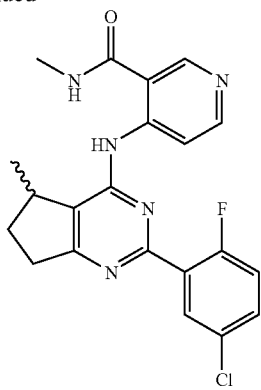

4-[2-(5-Chloro-2-fluoro-phenyl)-5-methyl-6,7-dihydro-5H-cyclopentapyrimidin-4-ylamino]-nicotinic acid ethyl ester. 48

Following the general reaction procedure for the synthesis of [2-(5-chloro-2-fluorophenyl)-5-methyl-6,7-dihydro -5H-cyclopentapyrimidin-4-yl]-(3-methyl-pyridin-4-yl)-amine 43,34-[2-(-chloro-2-fluoro-phenyl)-5-methyl-6,7-dihydro-5H-cyclopentapyrimidin-4-ylamino]-nicotinic acid ethyl ester, 48 was isolated in 68% yield.

4-[2-(5-Chloro-2-fluorophenyl)-5-methyl-6,7-dihydro-5H-cyclopentapyrimidin-4-ylamino]-nicotinic acid, 49

To a suspension of 4-[2-(5-chloro-2-fluoro-phenyl)-5-methyl-6,7-dihydro-5H-cyclopentapyrimidin-4-ylamino]-nicotinic acid ethyl ester (180 mg, 0.42 mmol, 1 eq) in MeOH (5 ml) was added a 1N NaOH$_{(aq)}$ solution (634 µl, 0.63 mmol, 1.5 eq) and the reaction mixture was heated to reflux for 1 h. The solution was cooled to rt and concentrated in vacuo. Water (20 ml) was added to the crude material and the aqueous layer was acidified to pH 4. The solid was filtered, washed with water (2×5 ml) and dried overnight to give 4-[2-(5-chloro-2-fluorophenyl)-5-methyl-6,7-dihydro-5H-cyclopentapyrimidin-4-ylamino]-nicotinic acid, 49 (160 mg, 95%) as a white solid.

4-[2-(5-Chloro-2-fluorophenyl)-5-methyl-6,7-dihydro-5H-cyclopentapyrimidin-4-ylamino]-N-methyl-nicotinamide, 47

To a suspension of 4-[2-(5-chloro-2-fluorophenyl)-5-methyl-6,7-dihydro-5H-cyclopentapyrimidin-4-ylamino]-nicotinic acid (20 mg, 0.05 mmol, 1 eq) in DMF (2 ml) was added triethylamine (8 µl, 0.05 mmol, 1.1 eq) followed by methylamine (250 µl, 3.89 mmol, 2M solution in THF, 10 eq). To the suspension was added a solution of PyBOP (40 mg, 0.08 mmol, 1.5 eq) in DMF (1 ml) dropwise. The reaction mixture was stirred at room temperature for 16 h. The reaction was concentrated in vacuo and the residue was triturated with ether (2×20 ml). The crude residue was purified by flash column chromatography (100% ethylacetate) to afford 4-[2-(5-chloro-2-fluorophenyl)-5-methyl-6,7-dihydro-5H-cyclopentapyrimidin-4-ylamino]-N-methyl-nicotinamide, 47 (12 mg, 58%) as a white solid.

Compound 46 was prepared by the method described for the synthesis of compound 47 employing ammonia in place of methylamine.

Administration and Use

The compounds of the invention are useful in treating conditions associated with fibroproliferation. Thus, the compounds of formula (1) or their pharmaceutically acceptable salts or prodrug forms are used in the manufacture of a medicament for prophylactic or therapeutic treatment of mammals, including humans, in respect of conditions characterized by excessive activity of TGFβ.

TGFβ inhibition activity is useful in treating fibroproliferative diseases, treating collagen vascular disorders, treating eye diseases associated with a fibroproliferative condition, venting excessive scarring, treating neurological conditions and other conditions that are targets for TGFβ inhibitors and in preventing excessive scarring that elicits and accompanies restenosis following coronary angioplasty, cardiac fibrosis occurring after infarction and progressive heart failure, and in hypertensive vasculopathy, and keloid formation or hypertrophic scars occurring during the healing of wounds including surgical wounds and traumatic lacerations.

Neurological conditions characterized by TGFβ production include CNS injury after traumatic and hypoxic insults, Alzheimer's disease, and Parkinson's disease.

Other conditions that are potential clinical targets for TGFβ inhibitors include myelofibrosis, tissue thickening resulting from radiation treatment, nasal polyposis, polyp surgery, liver cirrhosis, and osteoporosis.

Diseases benefited by TGFβ inhibition include cardiovascular diseases such as congestive heart failure, dilated cardiomyopathy, myocarditis, or vascular stenosis associated with atherosclerosis, angioplasty treatment, or surgical incisions or mechanical trauma; kidney diseases associated with fibrosis and/or sclerosis, including glomerulonephritis of all etiologies, diabetic nephropathy, and all causes of renal interstitial fibrosis, including hypertension, complications of drug exposure, such as cyclosporin, HIV-associated nephropathy, transplant nephropathy, chronic ureteral obstruction; hepatic diseases associated with excessive scarring and progressive sclerosis, including cirrhosis due to all etiologies, disorders of the biliary tree, and hepatic dysfunction attributable to infections such as hepatitis virus or parasites; syndromes associated with pulmonary fibrosis with consequential loss of gas exchange or ability to efficiently move air into and out of the lungs, including adult respiratory distress syndrome, idiopathic pulmonary fibrosis, or pulmonary fibrosis due to infectious or toxic agents such as smoke, chemicals, allergens, or autoimmune disease; all collagen vascular disorders of a chronic or persistent nature including progressive systemic sclerosis, polymyositis, scleroderma, dermatomyositis, fascists, or Raynaud's syndrome, or arthritic conditions such as rheumatoid arthritis; eye diseases associated with fibroproliferative states, including proliferative vitreoretinopathy of any etiology or fibrosis associated with ocular surgery such as retinal reattachment, cataract extraction, or drainage procedures of any kind; excessive or hypertrophic scar formation in the dermis occurring during wound healing resulting from trauma or surgical wounds; disorders of the gastrointestinal tract associated with chronic inflammation, such as Crohn's disease or ulcerative colitis or adhesion formation as a result of trauma or surgical wounds, polyposis or states post polyp surgery; chronic scarring of the peritoneum associated with endometriosis, ovarian disease, peritoneal dialysis, or surgical wounds; neurological conditions characterized by TGFβ production or enhanced sensitivity to TGFβ, including states post-traumatic or hypoxic injury, Alzheimer's disease, and Parkinson's disease; diseases of the joints involving scarring sufficient to impede mobility or produce pain, including states post-mechanical or surgical trauma, osteoarthritis and rheumatoid arthritis; and cancer including but not limited to colorectal carcinomas, pancreatic carcinomas, intramucosal carcinoma, primary invasive carcinoma without distant metastasis, primary invasive carcinoma with distant metastasis, and in distant metastasis.

The modulation of the immune and inflammation systems by TGFβ (Wahl, et al., *Immunol. Today* (1989) 10:258-261) includes stimulation of leukocyte recruitment, cytokine production, and lymphocyte effector function, and inhibition of T-cell subset proliferation, B-cell proliferation, antibody formation, and monocytic respiratory burst. TGFβ is a stimulator for the excess production of extracellular matrix proteins, including fibronectin and collagen. It also inhibits the production of enzymes that degrade these matrix proteins. The net effect is the accumulation of fibrous tissue which is the hallmark of fibroproliferative diseases.

TGFβ is active as a homodimer, but is synthesized and secreted from cells as an inactive latent complex of the mature homodimer and proregions, called latency associated protein (LAP). These proteins bind to each other through noncovalent interactions (Lyons and Moses, *Eur. J. Biochem.* (1990) 187:467). LAP is often disulfide-linked to separate gene products, called latent TGFβ binding proteins or LTBP's. These latent forms provide stability for the mature cytokine and a means for targeting it to the extracellular matrix and cell surfaces (Lawrence, *Eur. Cytokine Network* (1996) 7:363-374). Activation of the latent complex occurs after secretion from cells and is believed to result from the action of proteases, such as plasmin (Munger, et al., *Kidney Intl.* (1997) 51:1376-1382), on LAP, thrombospondin-1 binding (Crawford, et al., *Cell* (1998) 93:1159-1170), and binding to the integrin v6 (Munger, et al., *Cell* (1999) 319-328).

Other than v6 there is a variety of cell surface proteins/receptors that transduce the signals initiated by binding of the active TGFβ ligand to its receptors. These include types I, II, III, IV; and V. Type IV is present only in the pituitary gland while the others are ubiquitous. The binding affinities among the three isoforms for the type I and II receptors differ such that these two receptors bind TGFβ1 and TGFβ3 more tightly than TGFβ2 (Massague, *Cell* (1992) 69:1067-1070).

The type IV receptor or endoglin has a similar isoform binding profile in contrast to the type III receptor, betaglycan, which binds equally well to all three isoforms (Wang, et al., *Cell* (1991) 67:797-805; Lopez-Casillas, *Cell* (1991) 67:785-795). The type V receptor binds to IGFBP-3 and is thought to have an active kinase domain similar to the type I and II receptors. Cloning of the type I and type II receptors demonstrated the existence of cytoplasmic serine/threonine kinase domains (Wrana, et al., *Cell* (1992) 71:1003-1014; Lin, et al., *Cell* (1992) 68:775-785; *Ibid.* 71:1069; Massague, *Cell* (1992) 69:1067-1070). Initiation of the TGFβ signaling pathway results from the binding of the TGFβ ligand to the extracellular domain of the type II receptor (Massague, *Ann. Rev. Biochem.* (1998) 67:753-791). The bound receptor then recruits type I receptor into a multimeric membrane complex, whereupon the constitutively active type II receptor kinase phosphorylates and activates type I receptor kinase. The function of the type I receptor kinase is to phosphorylate a receptor-associated co-transcription factor, smad-2/3, thereby releasing it into the cytoplasm where it binds to smad-4. This smad complex translocates into the nucleus, associates with a DNA-binding cofactor, such as Fast-1, binds to enhancer regions of specific genes, and activates transcription. The expression of these genes leads to the synthesis of cell cycle regulators that control proliferative responses or extracellular matrix proteins that mediate outside-in cell signaling, cell adhesion, migration, and intercellular communication.

The manner of administration and formulation of the compounds useful in the invention and their related compounds will depend on the nature of the condition, the severity of the condition, the particular subject to be treated, and the judgment of the practitioner; formulation will depend on mode of administration. As the compounds of the invention are small molecules, they are conveniently administered by oral administration by compounding them with suitable pharmaceutical excipients so as to provide tablets, capsules, syrups, and the like. Suitable formulations for oral administration may also include minor components such as buffers, flavoring agents and the like. Typically, the amount of active ingredient in the formulations will be in the range of 5%-95% of the total formulation, but wide variation is permitted depending on the carrier. Suitable carriers include sucrose, pectin, magnesium stearate, lactose, peanut oil, olive oil, water, and the like.

The compounds useful in the invention may also be administered through suppositories or other transmucosal vehicles. Typically, such formulations will include excipients that facilitate the passage of the compound through the mucosa such as pharmaceutically acceptable detergents.

The compounds may also be administered topically, for topical conditions such as psoriasis, or in formulation intended to penetrate the skin. These include lotions, creams, ointments and the like which can be formulated by known methods.

The compounds may also be administered by injection, including intravenous, intramuscular, subcutaneous or intraperitoneal injection. Typical formulations for such use are liquid formulations in isotonic vehicles such as Hank's solution or Ringer's solution.

Alternative formulations include nasal sprays, liposomal formulations, slow-release formulations, and the like, as are known in the art.

Any suitable formulation may be used. A compendium of art-known formulations is found in *Remington's Pharmaceutical Sciences*, latest edition, Mack Publishing Company, Easton, Pa. Reference to this manual is routine in the art.

The dosages of the compounds of the invention will depend on a number of factors which will vary from patient to patient. However, it is believed that generally, the daily oral dosage will utilize 0.001-100 mg/kg total body weight, preferably from 0.01-50 mg/kg and more preferably about 0.01 mg/kg-10 mg/kg. The dose regimen will vary, however, depending on the conditions being treated and the judgment of the practitioner.

It should be noted that the compounds of formula (1) can be administered as individual active ingredients, or as mixtures of several embodiments of this formula. The compounds of the invention may be used as single therapeutic agents or in combination with other therapeutic agents. Drugs that could be usefully combined with these compounds include natural or synthetic corticosteroids, particularly prednisone and its derivatives, monoclonal antibodies targeting cells of the immune system, antibodies or soluble receptors or receptor fusion proteins targeting immune or non-immune cytokines, and small molecule inhibitors of cell division, protein synthesis, or mRNA transcription or translation, or inhibitors of immune cell differentiation or activation.

As indicated above, although the compounds of the invention may be used in humans, they are also available for veterinary use in treating animal subjects.

EXAMPLES

The invention will now be described in more detail by way of the following Examples, which are not to be construed as limiting the invention in any way.

Example 1

TGF-β Inhibition Assay

The ability of invention compounds to inhibit TGF can be evaluated in a TGF R1 kinase autophosphorylation protocol. This assay can be conducted as follows: Compound dilutions and reagents are prepared fresh daily. Compounds are diluted from DMSO stock solutions to 2 times the desired assay concentration, keeping final DMSO concentration in the assay less than or equal to 1%. TGF R1 kinase is diluted to 4 times the desired assay concentration in buffer and DTT. ATP is diluted into 4× reaction buffer, and gamma-$^{32}$P-ATP is added at 60 µCi/mL.

The assay is performed by adding 10 µl of the enzyme to 20 µl of the compound solution. The reaction is initiated by the addition of 10 µl of ATP mix. Final assay conditions include 10 µM ATP, 170 nM TGF R1 kinase, and 1M DTT in 20 mM MOPS, pH7. The reactions are then incubated at room temperature for 20 minutes, after which they are stopped by transferring 23 µl of reaction mixture onto a phosphocellulose 96-well filter plate, (pre-wetted with 15 µl of 0.25M $H_3PO_4$ per well). After 5 minutes, the wells are washed 4× with 75 mM $H_3PO_4$ and once with 95% ethanol. The plate is dried, scintillation cocktail is added to each well, and the wells are counted in a Packard TopCount microplate scintillation counter. The ability of a compound to inhibit the enzyme is determined by comparing the counts obtained in the presence of compound to those of the positive control (in the absence of compound) and the negative control (in the absence of enzyme).

Example 2

TGF-β Inhibition Assay

Invention compounds were tested for their abilities to inhibit the phosphorylation of the substrate casein. The assay was conducted as follows: Compound dilutions and reagents were prepared fresh daily. Compounds were diluted from DMSO stock solutions to 2 times the desired assay concentration, keeping final DMSO concentration in the assay less than or equal to 1%. TGF RI kinase was diluted to 4 times the desired assay concentration in buffer and DTT. ATP and casein were diluted into 4× reaction buffer, and gamma-$^{32}$P-ATP was added at 50 µCi/mL.

The assay was performed by adding 10 µl of the enzyme to 20 µl of the compound solution. The reaction was initiated by the addition of 10 µl of the casein/ATP mix. Final assay conditions included 2.5 µM ATP, 100 µM casein, 6.4 nM TGF R1 kinase, and 1M DTT in 20 mM Tris buffer, pH 7.5. The reactions were incubated at room temperature for 45 minutes. The reactions were then stopped by transferring 23 µl of reaction mixture onto a phosphocellulose 96-well filter plate, which had been pre-wetted with 15 µl of 0.25M $H_3PO_4$ per well. After 5 minutes, the wells were washed 4× with 75 mM $H_3PO_4$ and once with 95% ethanol. The plate was dried, scintillation cocktail was added to each well, and the wells were counted in a Packard TopCount microplate scintillation counter. The ability of a compound to inhibit the enzyme was determined by comparing the counts obtained in the presence of the compound to those of the positive control (in the absence of compound) and the negative control (in the absence of enzyme).

In both of the assays referenced above, $IC_{50}$ values can be determined with curve-fitting plots available with common software packages. Approximate $IC_{50}$ values can be calculated using formula:

$$IC_{50}\,(app) = A \times i/(1-A)$$

where A=fractional activity and i=total inhibitor concentration.

Example 3

Effect of Compound 35 on Bleomycin-Induced SMAD Phosphorylation

In TGF-beta signaling, the binding of a ligand-dimer leads to the formation of the receptor complex. The receptor type II auto-phosphorylates and phosphorylates the receptor type I which then is thought to phosphorylate and activate the receptor-regulated SMAD transcription factors.

SMADs are evolutionarily conserved proteins that mediate transcription TGF-beta and other cytokines. Upon activation these proteins directly translocate to the nucleus where they are thought to activate transcription. The SMAD family of proteins is thought to encompass 6 different forms. SMAD-4 has been shown to be mutated in human cancers. Because the TGF-beta family members are known to exert pleiotropic effects both negatively and positively controlling the cell fate, inhibition of TGF-beta activation of may provide a means to limit the impact of SMAD-4 mutations in human cancer cells.

The effect of TGF-beta inhibitors on bleomycin-induced SMAD phosphorylation was studied in male Sprague-Dawley rats purchased from Charles River. Rats were housed in groups of two in the animal facility and provided with filtered air at a constant temperature and humidity. The rats were allowed to acclimate to the new environment for one week before all treatments. A 12:12 hour light-dark cycle was maintained, and the animals had free access to food and water.

To induce SMAD activation, rats were intubated with 0.5 ml of saline or 0.5 ml of 1.0 unit/ml of bleomycin by intratracheal injection under anesthesia. The anesthetic solution used was a mixture of 0.4 ml of ketamine (100 mg/ml) and 0.25 ml of xylazine (20 mg/ml) at a dose of 1.3 ml/kg.

On days 1 to 5, treated rats were weighed and orally dosed with compound 35 two-times a day at 40 mg/kg.

On Day 5, after dosing, rats were sacrificed by an overdose of the ketamine/xylazine cocktail, and then the trachea, heart and lungs of the animals were removed en bloc. All lung lobes were collected, dissected and stored in −80° C. for phospo SMAD ELISA assays.

Determination of SMAD Activation

To evaluate the effect of SMAD activation (an indicia of fibrosis), a phospho SMAD 2/3 ELISA assay was performed using the lung tissue of the sacrificed animals. Compound 35 was shown to be able to significantly reduce bleomycin-induced phosphorylation of P-Smad 2/3 in the lung after oral delivery of the inhibitor.

In comparison to the control group of rats, compound 35 was shown to reduce bleomycin induced phosphorylation of P-Smad 2/3 in the lung after oral delivery at dose of 40 mg/kg, bid.

The examples set forth above are provided to give those of ordinary skill in the art with a complete disclosure and description of how to make and use the preferred embodiments of the compositions, and are not intended to limit the scope of what the inventors regard as their invention. Modifications of the above-described modes for carrying out the invention that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A compound of the formula

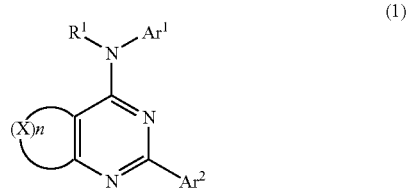

(1)

or a pharmaceutically acceptable salt thereof, wherein X is C and n is 2-5 so as to form a fused ring between positions 5 and 6 of ring A wherein said fused ring is optionally substituted, is saturated, unsaturated or aromatic with the proviso that if n is 4, the fused ring is not aromatic;

wherein $Ar^2$ is an optionally substituted aromatic or optionally substituted heteroaromatic moiety wherein said heteroaromatic moiety contains one or more O, S, and/or N;

$Ar^1$ is a six-membered optionally substituted aromatic or optionally substituted heteroaromatic moiety wherein said heteroaromatic moiety contains one or more O, S, and/or N; and $R^1$ is H or optionally substituted alkyl (1-10C), alkenyl (2-10C), or alkynyl (2-10C).

2. The compound of claim 1, wherein $Ar^1$ is monocyclic and contains 1-2N and $Ar^2$ is phenyl; or $R^1$ is H or unsubstituted lower alkyl (1-6C).

3. The compound of claim 1, wherein optional substituents on the aromatic or heteroaromatic moiety represented by $Ar^1$ or $Ar^2$ or on said fused ring comprise alkyl (1-10C), alkenyl (2-10C), alkynyl (2-10C), acyl (1-10C), aryl, alkylaryl, aroyl, O-aryl, O-alkylaryl, O-aroyl, NR-aryl, NR-alkylaryl, NR-aroyl, or the hetero forms of any of the foregoing, halo, OR, $NR_2$, SR, —SOR, —NRSOR, —NRSO$_2$R, —SO$_2$R, —OCOR, —NRCOR, —NRCONR$_2$, —NRCOOR, —OCONR$_2$, —COOR, —SO$_3$R, —CONR$_2$, —SO$_2$NR$_2$, —CN, —CF$_3$, and/or NO$_2$, wherein each R is independently H or alkyl (1-6C) wherein said alkyl, alkenyl, alkynyl, acyl, aryl, alkylaryl, aroyl, O-aryl, O-alkylaryl, O-aroyl, NR-aryl, NR-alkylaryl, or NR-aroyl substituents may be further substituted by halo, OR, $NR_2$, SR, —SOR, —NRSOR, —NRSO$_2$R, —SO$_2$R, —OCOR, —NRCOR, —NRCONR$_2$, —NRCOOR, —OCONR$_2$, —COOR, —SO$_3$R, —CONR$_2$, —SO$_2$NR$_2$, —CN, —CF$_3$, and/or NO$_2$.

4. The compound of claim 1, wherein the fused ring contains 5 or 6 members.

5. A pharmaceutical composition which comprises as active ingredient the compound of claim 1, along with a pharmaceutically acceptable excipient.

6. The pharmaceutical composition of claim 5, wherein the compound of claim 1 is 4-[2-(5-Chloro-2-fluoro-phenyl)-6,7-dihydro-5H-cyclopentapyrimidin-4-ylamino]-N-methyl-nicotinamide or a pharmaceutically acceptable salt thereof.

7. A method to treat rheumatoid arthritis ameliorated by inhibiting TGFβ which method comprises administering to a subject in need of such treatment an effective amount of the compound of claim 1 or a pharmaceutical composition thereof.

* * * * *